(12) United States Patent
Bolli et al.

(10) Patent No.: US 7,285,549 B2
(45) Date of Patent: *Oct. 23, 2007

(54) SULFAMIDES AND THEIR USE AS ENDOTHELIN RECEPTOR ANTAGONISTS

(75) Inventors: Martin Bolli, Allschwil (CH);
Christoph Boss, Allschwil (CH);
Walter Fischli, Allschwil (CH);
Martine Clozel, Saint-Louis (FR);
Thomas Weller, Binningen (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/400,697

(22) Filed: Apr. 7, 2006

(65) Prior Publication Data

US 2006/0178365 A1  Aug. 10, 2006

Related U.S. Application Data

(63) Continuation of application No. 10/433,041, filed as application No. PCT/EP01/14182 on Dec. 4, 2001, now Pat. No. 7,094,781.

(30) Foreign Application Priority Data

Dec. 18, 2000 (WO) .................... PCT/EP00/12890

(51) Int. Cl.
*C07D 401/04* (2006.01)
*C07D 239/47* (2006.01)

(52) U.S. Cl. .......................... 514/235.8; 514/255.05; 514/269; 544/123; 544/296; 544/319

(58) Field of Classification Search ............ 544/123, 544/296, 319; 514/235.8, 255.05, 269
See application file for complete search history.

(56) References Cited

U.S. PATENT DOCUMENTS 4,233,294 A    11/1980  Maurer et al.
7,094,781 B2 *  8/2006  Bolli et al. ............... 514/235.8

FOREIGN PATENT DOCUMENTS

| EP | 0 526 708 A1 | 2/1993 |
|---|---|---|
| EP | 0 633 259 A1 | 1/1995 |
| EP | 0 657 548 A1 | 6/1995 |
| EP | 0 743 307 A1 | 11/1996 |
| EP | 0 882 719 A1 | 12/1998 |
| EP | 0 959 072 A1 | 11/1999 |
| WO | WO 96/19459 | 6/1996 |
| WO | WO 96/16963 | 12/1996 |
| WO | WO 00/42035 | 7/2000 |
| WO | WO 01/17976 | 3/2001 |
| WO | WO 01/46156 | 6/2001 |
| WO | WO 01/81335 | 11/2001 |
| WO | WO 01/81338 | 11/2001 |

OTHER PUBLICATIONS

Neidhart, W., et el., Discovery of R048-5695: A Potent Mixed Endothelin Receptor Antagonist Optimized from Bosentan, Bioorganic & Medical Chemistry Letters,. 7(17):2223-2228, 1997.

Gohring, W. et al., Development of a Process to Prepare 2-Cyanopyrimidine on commercial Scale, Chimia, 50 Nov. 1996.

Nugent, A., et al, Pyrimidine Thioethers: A Novel Class of HIV' Reverse Transcriptase Inhibitors with Activiity Against BHAP-Resistant HIV, J. Med. Chem., 41: 3793-3803, 1998.

March, Jerry, Advanced Organic Chemistry, Fourth Ed p. 499 end references cited therein, 1992.

Kohara, Y., et al., Synthesis and Angiotensin II Receptor Antagonistic Activities at Benzimldazote Derivatives Bearing Acidic Heterocycles as Novel Tetrazole Bioisosteres, J. Mad. Chem., 39: 5228-5235, 1996.

Graf. R., Chem. Bar., 92:509-513, 1959.

Weiss. G., et al., Liebigs Ann. Chem., 729:40-51, 1969.

Kloek, J., et al., An Improved Synthesis of Sulfamoyl Chlorides, J. Org. Chem., 41 (25):4028-4029, 1976.

Dickinson. R,. et al. Thromboxane Modulating Agents. 3. 1H-Imidazol-1-ylalkyl-and 3-Pyridinylalkyl-Substituted 3-[2-[Arylsulfonyl)amino]ethyl]benzenepropanoic Acid Derivatives as Duel Thromboxane Synlhase Inhibitor/Thromboxane Receptor Antagonists, J. Med. Chem., 40:3442-3452 1997.

Cohen, E., et al., Sulfamoyl Chlohde, Sutfamides and Sulfimide, J. Am. Chem.Soc., 84:1994-2002, 1962.

Olson. A., et al., Orally Active Isoxazoline Glycoprotein IIb/IIIa Antagonists with Extended Duration of Action, J. Med. Chem., 42:1178-1192.1999.

Crosby, D., et al., n-Buty 5-Chloro-2-pyrimidoxyacetate-A Plant Growth Regulator Analog. J. Org. Chem., 25:1916-1919, Nov. 1960.

Morgan, Ed., Synthesis of p-Alkylphenylacetic Acids, Tetrahedron, 23:1735-1738, 1967.

Tozer, M., et al., 4-Chlorobenzyl Sulfonamide and Sulfamide Derivatives of Histamine Homologues: The Design of Potent Histamine H3 Receptor Antagonists Bioorganic & Medicinal Chemistry Letters 9:3103-3108, 1999.

Dewynter, et al., Tetrahedron, 49(1):65-76, 1993.

Bennett. J. Claude, et al., Textbook at Medicine, vol. 1, 20th Edition 1004-1010, 1996.

(Continued)

*Primary Examiner*—Deepak Rao
(74) *Attorney, Agent, or Firm*—Hoxie & Associates LLC

(57) ABSTRACT

The invention relates to novel sulfamides and their use as active ingredients in the preparation of pharmaceutical compositions. The invention also concerns related aspects including processes for the preparation of the compounds, pharmaceutical compositions containing one or more of those compounds and especially their use as endothelin receptor antagonists.

5 Claims, No Drawings

OTHER PUBLICATIONS

Rubanyi, G.M.. et al. Endothelins: Molecular Biology, Biochemistry, Pharmacology, Physiology and Pathophysiology, Pharm. Reviews, 46(3), 1994.

Arai, et al., Cloning and expression of a cDNA encoding an endothelin Recetor Nature, 348:730-732, 1990.

Breu. V. et al., In vitro characterization at R0 46-2005, a novel synthetic non-peptide endothelin antagonist of ETA and ETB receptors, FEBS 13244, 334(2):210-214, Nov. 1993.

Neidhart, W., et al, The Discovery of Nonpeptide Endothelin Receptor Antagonists. Progression towards Bosentan, Chemia, 50:519-524, Nov. 1996.

McMillen, M.. el al., Endothelins: Polyfunctional Cytokines. J. Amer. College of Surgeons, 180:621-640, 1995.

Ogawa. V. et al., Molecular Cloning of a Non-Isopeptide-Selective Human Endothehin Receptor, Biochem. Biophy. Research Comm., 178(1):248-255 Jul. 1991.

Ohlstein, E., et el., Endothelin-I Modulates Vascular Smooth Muscle Structure and Vasomotion: Implications in Cardiovascular Pathology, Drug Development Research, 29:108-128, 1993.

Sakural, et al., Cloning of a cDNA encoding a non-isopeptide-selective subtype at the endothelin receptor, Nature. 348:732-735, Dec. 1990.

Sumner, M., et al., Endothelin ETA and ETB receptors mediate vascular smooth muscle contraction, Br. J. Pharmacol., 107:858-860, 1992.

Yanaglsawa, M., et al., A novel potent vasoconstrictor peptide produced by vascular endothelial cells, Nature, 332:411-415, Mar. 1988.

* cited by examiner

SULFAMIDES AND THEIR USE AS ENDOTHELIN RECEPTOR ANTAGONISTS

CROSS-REFERENCE TO RELATED APPLICATION

This application is a Continuation of U.S. patent application Ser. No. 10/433,041 filed May 27, 2003 now U.S. Pat. No. 7,094,781 which is a 371 of PCT/EP01/14182 filed Dec. 4, 2001.

The present invention relates to novel pyrimidine-sulfamides of the general formula I and their use as active ingredients in the preparation of pharmaceutical compositions. The invention also concerns related aspects including processes for the preparation of the compounds, pharmaceutical compositions containing one or more compounds of the general formula I and especially their use as endothelin receptor antagonists.

Endothelins (ET-1, ET-2, and ET-3) are 21-amino acid peptides produced and active in almost all tissues (Yanagisawa M et al.: Nature (1988) 332:411). Endothelins are potent vasoconstrictors and important mediators of cardiac, renal, endocrine and immune functions (McMillen M A et al: J Am Coll Surg (1995) 180:621). They participate in bronchoconstriction and regulate neurotransmitter release, activation of inflammatory cells, fibrosis, cell proliferation and cell differentiation (Rubanyi G M et al. Pharmacol Rev (1994) 46:328).

Two endothelin receptors have been cloned and characterized in mammals ($ET_A$, $ET_B$) (Arai H et al.: Nature (1990) 348:730; Sakurai T et al.: Nature (1990) 348:732). The $ET_A$ receptor is characterized by higher affinity for ET-1 and ET-2 than for ET-3. It is predominant in vascular smooth cells and mediates vasoconstricting and proliferative responses (Ohlstein E H et al.: Drug Dev Res (1993) 29:108). In contrast, the $ET_B$ receptor has equivalent affinity for the three endothelin isopeptides and binds the linear form of endothelin, tetra-ala-endothelin, and sarafotoxin S6C (Ogawa Y et al.: BBRC (1991) 178:248). This receptor is located in the vascular endothelium and smooth muscles, and is also particularly abundant in lung and brain. The $ET_B$ receptor from endothelial cells mediates transient vasodilator responses to ET-1 and ET-3 through the release of nitric oxide and/or prostacyclin whereas the $ET_B$ receptor from smooth muscle cells exerts vasocontricting actions (Sumner M J et al.: Brit J Pharmacol (1992) 107:858). $ET_A$ and $ET_B$ receptors are highly similar in structure and belong to the superfamily of G-protein coupled receptors.

A pathophysiological role has been suggested for ET-1 in view of its increased plasma and tissue levels in several disease states such as hypertension, pulmonary hypertension, sepsis, atherosclerosis, acute myocardial infarction, congestive heart failure, renal failure, migraine and asthma. As a consequence, endothelin receptor antagonists have been studied extensively as potential therapeutic agents. Endothelin receptor antagonists have demonstrated preclinical and/or clinical efficacy in various diseases such as cerebral vasospasm following subarachnoid hemorrhage, heart failure, pulmonary and systemic hypertension, neurogenic inflammation, renal failure and myocardial infarction.

Today, only one endothelin receptor antagonist (Tracleer™) is marketed and several are in clinical trials. However, some of these molecules possess a number of weaknesses such as complex synthesis, low solubility, high molecular weight, poor pharmacokinetics, or safety problems (e.g. liver enzyme increases). Furthermore, the contribution of differing $ET_A$/$ET_B$ receptor blockade to the clinical outcome is not known. Thus, tailoring of the physicochemical and pharmacokinetic properties and the selectivity profile of each antagonist for a given clinical indication is mandatory. So far, no endothelin receptor antagonists with a pyrimidine core structure containing a sulfamide unit, have been reported [2, 3, 5, 6, 8]. We have discovered a new class of substituted pyrimidines of the structure below and found that they allow the specific tailoring described above and in addition compounds exhibiting mixed as well as $ET_A$-selective binding profiles have been identified.

The inhibitory activity of the compounds of general formula I on endothelin receptors can be demonstrated using the test procedures described hereinafter:

For the evaluation of the potency and efficacy of the compounds of the general formula I the following tests were used:

1) Inhibition of endothelin binding to membranes from CHO cells carrying human ET receptors:

For competition binding studies, membranes of CHO cells expressing human recombinant $ET_A$ or $ET_B$ receptors were used. Microsomal membranes from recombinant CHO cells were prepared and the binding assay made as previously described (Breu V., et al, FEBS Lett 1993; 334:210).

The assay was performed in 200 uL 50 mM Tris/HCl buffer, pH 7.4, including 25 mM $MnCl_2$, 1 mM EDTA and 0.5% (w/v) BSA in polypropylene microliter plates. Membranes containing 0.5 ug protein were incubated for 2 h at 20° C. with 8 pM [$^{125}$I]ET-1 (4000 cpm) and increasing concentrations of unlabelled antagonists. Maximum and minimum binding were estimated in samples without and with 100 nM ET-1, respectively. After 2 h, the membranes were filtered on filterplates containing GF/C filters (Unifilterplates from Canberra Packard S.A. Zürich, Switzerland). To each well, 50 uL of scintillation cocktail was added (MicroScint 20, Canberra Packard S.A. Zürich, Switzerland) and the filter plates counted in a microplate counter (TopCount, Canberra Packard S.A. Zürich, Switzerland).

All the test compounds were dissolved, diluted and added in DMSO. The assay was run in the presence of 2.5% DMSO which was found not to interfere significantly with the binding. $IC_{50}$ was calculated as the concentration of antagonist inhibiting 50% of the specific binding of ET-1. For reference compounds, the following $IC_{50}$ values were found: $ET_A$ cells: 0.075 nM (n=8) for ET-1 and 118 nM (n=8) for ET-3; $ET_B$ cells: 0.067 nM (n=8) for ET-1 and 0.092 nM (n=3) for ET-3.

The $IC_{50}$ values obtained with compounds of general formula I are given in Table 1.

TABLE 1

| Compound of Example | $IC_{50}$ [nM] ||
| --- | --- | --- |
|  | $ET_A$ | $ET_B$ |
| Example 1 | 721 | 8429 |
| Example 2 | 2190 | 8743 |
| Example 3 | 1384 | 744 |
| Example 4 | 96 | 680 |
| Example 5 | 28 | 1280 |
| Example 6 | 286 | 7240 |
| Example 7 | 1237 | 9467 |
| Example 8 | 1160 | >10000 |
| Example 9 | 3629 | >10000 |
| Example 10 | 2866 | 193 |
| Example 12 | 59 | >10000 |
| Example 14 | 5.6 | 1033 |
| Example 15 | 18.5 | 2161 |

TABLE 1-continued

| Compound of Example | IC$_{50}$ [nM] ET$_A$ | IC$_{50}$ [nM] ET$_B$ |
| --- | --- | --- |
| Example 16 | 45 | 8452 |
| Example 18 | 8.5 | 3333 |
| Example 19 | 25 | 3414 |
| Example 20 | 4.9 | 1723 |
| Example 21 | 7 | 1001 |
| Example 22 | 12 | 434 |
| Example 23 | 3.6 | 1585 |
| Example 24 | 2.2 | 2496 |
| Example 26 | 54 | >10000 |
| Example 29 | 13.5 | 4230 |
| Example 32 | 3.5 | 864 |
| Example 33 | 3.7 | 609 |
| Example 34 | 23 | 3267 |
| Example 37 | 16 | 822 |
| Example 38 | 14.5 | 290 |
| Example 39 | 32.7 | 524 |
| Example 41 | 3.2 | 41.6 |
| Example 42 | 3.5 | 146 |
| Example 43 | 6.8 | 214 |
| Example 48 | 1.46 | 46.6 |
| Example 49 | 0.82 | 25.4 |
| Example 50 | 0.87 | 7.5 |
| Example 51 | 13.4 | 306 |
| Example 55 | 5.2 | 80 |
| Example 56 | 6.9 | 164 |
| Example 57 | 4.9 | 35.8 |
| Example 59 | 5.6 | 124 |
| Example 60 | 3.4 | 232 |
| Example 61 | 1.6 | 200 |
| Example 66 | 11 | 487 |
| Example 71 | 23.6 | 635 |
| Example 73 | 1.9 | 567 |
| Example 74 | 1.8 | 164 |
| Example 75 | 14 | 895 |
| Example 80 | 10 | >1000 |
| Example 81 | 3.6 | 274 |
| Example 84 | 37 | 574 |
| Example 88 | 16 | 1251 |
| Example 89 | 19 | 621 |
| Example 90 | 7.4 | 433 |
| Example 91 | 2.5 | 79 |
| Example 96 | 6.3 | 585 |
| Example 97 | 1.55 | 92 |
| Example 98 | 2.1 | 159 |
| Example 100 | 0.76 | 283 |
| Example 101 | 1.24 | 335 |
| Example 102 | 0.46 | 65 |
| Example 104 | 0.88 | 601 |
| Example 105 | 0.69 | 203 |
| Example 107 | 0.25 | 96 |
| Example 108 | 0.28 | 56 |
| Example 109 | 1.94 | >1000 |
| Example 110 | 2.3 | >1000 |
| Example 111 | 12.3 | 3750 |
| Example 112 | 0.52 | 257 |
| Example 113 | 4.26 | 581 |
| Example 114 | 8.3 | >1000 |
| Example 115 | 2.2 | >1000 |
| Example 116 | 1.3 | 567 |
| Example 117 | 0.45 | 518 |
| Example 118 | 0.34 | 611 |
| Example 119 | 4.2 | >1000 |
| Example 123 | 2.9 | 124 |
| Example 124 | 7.3 | 102 |
| Example 127 | 7.3 | 87 |
| Example 130 | 3.7 | 347 |
| Example 131 | 3.2 | 233 |
| Example 133 | 1.7 | 212 |
| Example 134 | 2.4 | 187 |
| Example 137 | 2.7 | 173 |
| Example 138 | 0.9 | 40 |
| Example 142 | 2.6 | 108 |
| Example 143 | 3.1 | 35 |
| Example 145 | 1.64 | >1000 |
| Example 146 | 5 | 514 |
| Example 147 | 1.2 | 408 |
| Example 149 | 15 | 1315 |
| Example 151 | 0.77 | 57 |
| Example 152 | 1.1 | 79 |
| Example 155 | 5.8 | 173 |
| Example 156 | 18 | 409 |
| Example 157 | 42.2 | 954 |
| Example 158 | 10 | 80 |
| Example 160 | 11 | 3221 |
| Example 161 | 6.2 | >1000 |
| Example 163 | 0.44 | 80 |
| Example 164 | 1 | 81 |
| Example 166 | 1 | 3 |
| Example 167 | 5.2 | 6.4 |
| Example 168 | 2.7 | 1.6 |
| Example 170 | 1.7 | 42 |
| Example 171 | 11 | 61 |
| Example 172 | 3 | 16 |
| Example 174 | 3.7 | 93 |
| Example 175 | 22 | 62 |
| Example 176 | 2.5 | 22 |
| Example 181 | 14.3 | 224 |
| Example 182 | 29 | 1867 |
| Example 184 | 29.5 | 3777 |
| Example 187 | 9.8 | 532 |
| Example 188 | 11 | 290 |
| Example 193 | 3.6 | >1000 |
| Example 194 | 9.5 | >1000 |
| Example 196 | 4.4 | >1000 |
| Example 197 | 1.16 | 418 |
| Example 198 | 38.4 | 667 |
| Example 199 | 12 | 205 |
| Example 200 | 23 | 310 |
| Example 201 | 133 | 682 |
| Example 202 | 9.6 | 351 |
| Example 204 | 390 | 1047 |
| Example 205 | 135 | 623 |
| Example 206 | 1.03 | 209 |
| Example 207 | 17 | >1000 |
| Example 208 | 17 | 342 |
| Example 209 | 733 | >1000 |
| Example 210 | 23 | 936 |
| Example 211 | 290 | 722 |
| Example 212 | 3.1 | >1000 |
| Example 213 | 1.32 | 347 |
| Example 214 | 0.76 | 241 |

2) Inhibition of endothelin-induced contractions on isolated rat aortic rings (ET$_A$ receptors) and rat tracheal rings (ET$_B$ receptors):

The functional inhibitory potency of the endothelin antagonists was assessed by their inhibition of the contraction induced by endothelin-1 on rat aortic rings (ET$_A$ receptors) and of the contraction induced by sarafotoxin S6c on rat tracheal rings (ET$_B$ receptors). Adult Wistar rats were anesthetized and exsanguinated. The thoracic aorta or trachea were excised, dissected and cut in 3-5 mm rings. The endothelium/epithelium was removed by gentle rubbing of the intimal surface. Each ring was suspended in a 10 ml isolated organ bath filled with Krebs-Henseleit solution (in mM; NaCl 115, KCl 4.7, MgSO$_4$ 1.2, KH$_2$PO$_4$ 1.5, NaHCO$_3$ 25, CaCl$_2$ 2.5, glucose 10) kept at 37° C. and gassed with 95% O$_2$ and 5% CO$_2$. The rings were connected to force transducers and isometric tension was recorded (EMKA Technologies SA, Paris, France). The rings were stretched to a resting tension of 3 g (aorta) or 2 g (trachea). Cumulative doses of ET-1 (aorta) or sarafotoxin S6c (trachea) were added after a 10 min incubation with the test compound or its vehicle. The functional inhibitory potency of the test compound was assessed by calculating the concentration ratio, i.e. the shift to the right of the $EC_{50}$ induced by different concentrations of test compound. $EC_{50}$ is the concentration of endothelin needed to get a half-maximal contraction, $pA_2$ is the negative logarithm of the antagonist concentration which induces a two-fold shift in the $EC_{50}$ value.

The $pA_2$ values obtained with compounds of formula I are given in Table 2.

TABLE 2

| Compound of Example | pA₂ value | |
|---|---|---|
| | $ET_A$ | $ET_B$ |
| Example 5 | 6.65 | |
| Example 14 | 8.4 | 5.63 |
| Example 18 | 8.15 | <5 |
| Example 20 | 7.21 | |
| Example 32 | 8.75 | |
| Example 37 | 7.83 | |
| Example 41 | 8.37 | |
| Example 51 | 6.55 | |
| Example 100 | 8.44 | |
| Example 102 | 8.40 | 6.76 |
| Example 119 | 7.38 | |
| Example 133 | 7.72 | |
| Example 161 | 6.29 | |
| Example 203 | 7.69 | 5.84 |

Because of their ability to inhibit the endothelin binding, the described compounds can be used for treatment of diseases, which are associated with an increase in vasoconstriction, proliferation or inflammation due to endothelin. Examples of such diseases are hypertension, pulmonary hypertension, coronary diseases, cardiac insufficiency, renal and myocardial ischemia, renal failure, cerebral ischemia, dementia, migraine, subarachnoidal hemorrhage, Raynaud's syndrome and portal hypertension. They can also be used in the treatment or prevention of atherosclerosis, restenosis after balloon or stent angioplasty, inflammation, stomach and duodenal ulcer, cancer, prostatic hypertrophy, erectile dysfunction, hearing loss, amaurosis, chronic bronchitis, asthma, gram negative septicemia, shock, sickle cell anemia, glomerulonephritis, renal colic, glaucoma, therapy and prophylaxis of diabetic complications, complications of vascular or cardiac surgery or after organ transplantation, complications of cyclosporin treatment, pain, hyperlipidemia as well as other diseases, presently known to be related to endothelin.

The compounds can be administered orally, rectally, parenterally, e.g. by intravenous, intramuscular, subcutaneous, intrathecal or transdermal administration or sublingually or as ophthalmic preparation or administered as aerosol. Examples of applications are capsules, tablets, orally administered suspensions or solutions, suppositories, injections, eye-drops, ointments or aerosols/nebulizers.

Preferred applications are intravenous, intra-muscular, or oral administrations as well as eye drops. The dosage used depends upon the type of the specific active ingredient, the age and the requirements of the patient and the kind of application. Generally, dosages of 0.1-50 mg/kg body weight per day are considered. The preparations with compounds can contain inert or as well pharmacodynamically active excipients. Tablets or granules, for example, could contain a number of binding agents, filling excipients, carrier substances or diluents.

The present invention relates to pyrimidine-sulfamides of the general formula I,

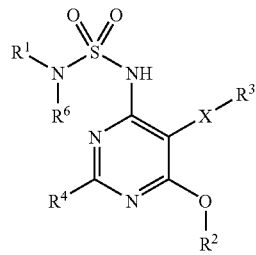

General Formula I wherein $R^1$ represents aryl; aryl-lower alkyl; heteroaryl; heteroaryl-lower alkyl; cycloalkyl; cycloalkyl-lower alkyl; heterocyclyl; heterocyclyl-lower alkyl; lower alkyl; hydrogen or may form a heterocyclyl- or cycloalkyl-ring together with $R^6$;

$R^2$ represents —$CH_3$; —$(CH_2)_n$—Y—$R^a$; —$(CH_2)_m$—C≡C—$(CH_2)_p$-Z-$R^a$; —$(CH_2)_k$—C($R^b$)=C$R^c R^d$; —$CH_2$-tetrahydrofuran-2-yl;

$R^3$ represents aryl; heteroaryl;

$R^4$ represents hydrogen; trifluoromethyl; lower alkyl; lower alkyl-amino; lower alkyloxy; lower alkyloxy-lower alkyloxy; hydroxy-lower alkoxy; lower alkyl-sulfinyl; lower alkylthio; lower alkylthio-lower alkyl; hydroxy-lower alkyl; lower alkyl-oxy-lower alkyl; hydroxy-lower alkyloxy-lower alkyl; hydroxy-lower alkyl-amino; lower alkyl-amino-lower alkyl; amino; di-lower alkyl-amino; [N-(hydroxy-lower alkyl)-N-(lower alkyl)]-amino; aryl; aryl-amino; aryl-lower alkyl-amino; aryl-thio; aryl-lower alkyl-thio; aryloxy; aryl-lower alkyl-oxy; aryl-lower alkyl; aryl-sulfinyl; heteroaryl; heteroaryl-oxy; heteroaryl-lower alkyl-oxy; heteroaryl-amino; heteroaryl-lower alkyl-amino; heteroaryl-thio; heteroaryl-lower alkyl-thio; heteroaryl-lower alkyl; heteroaryl-sulfinyl; heterocyclyl; heterocyclyl-lower alkyl-oxy; heterocyclyl-oxy; heterocyclyl-amino; heterocyclyl-lower alkyl-amino; heterocyclyl-thio; heterocyclyl-lower alkyl-thio; heterocyclyl-lower alkyl; heterocyclyl-sulfinyl; cycloalkyl; cycloalkyl-oxy; cycloalkyl-lower alkyl-oxy; cycloalkyl-amino; cycloalkyl-lower alkyl-amino; cycloalkyl-thio; cycloalkyl-lower alkyl-thio; cycloalkyl-lower alkyl; cycloalkyl-sulfinyl;

$R^6$ represents hydrogen; lower alkyl; or may form a heterocyclyl- or cycloalkyl-ring together with $R^1$;

X represents oxygen; sulfur; —$CH_2$— or a bond;

Y represents a bond, —O—; —NH—; —NH—$SO_2$—; —NH—$SO_2$—NH—; O—CO—; —CO—O—; —O—CO—NH—; —NH—CO—O—; —NH—CO—NH—

Z represents oxygen or a bond;

k represents the whole numbers 1, 2, 3, 4, 5 or 6;

n represents the whole numbers 2, 3, 4, 5 or 6;

m represents the whole numbers 1, 2, 3, 4 or 5;

p represents the whole numbers 0 (zero), 1, 2 or 3 and if p represents the whole number 0 (zero), Z cannot represent oxygen;

$R^a$ represents aryl; heteroaryl; lower alkyl; cycloalkyl; hydrogen;

$R^b$ and $R^c$ independently represent hydrogen or lower alkyl;

$R^d$ represents represents hydrogen; lower alkyl; aryl; heteroaryl;

and optically pure enantiomers, mixtures of enantiomers such as for example racemates, optically pure diastereomers, mixtures of diastereomers, diastereomeric racemates, mixtures of diastereomeric racemates and the meso-forms and pharmaceutically acceptable salts thereof.

In the definitions of the general formula I—if not otherwise stated—the expression lower means straight and branched chain groups with one to seven carbon atoms, preferably 1 to 4 carbon atoms. Examples of lower alkyl and lower alkoxy groups are methyl, ethyl, n-propyl, isopropyl, n-butyl, isobutyl, sec.-butyl, tert.-butyl, pentyl, hexyl, heptyl, methoxy, ethoxy, propoxy, butoxy, iso-butoxy, sec.-butoxy and tert.-butoxy. Lower alkylendioxy-groups are preferably methylen-dioxy and ethylen-dioxy groups. Examples of lower alkanoyl-groups are acetyl, propanoyl and butanoyl. Lower alkenylen means e.g. vinylen, propenylen and butenylen. Lower alkenyl and lower alkynyl means groups like ethenyl, propenyl, butenyl, 2-methylpropenyl, and ethinyl, propinyl, butinyl, pentinyl, 2-methylpentinyl. Lower alkenyloxy means allyloxy, vinyloxy and propenyloxy. The expression cycloalkyl means a saturated cyclic hydrocarbon ring with 3 to 7 carbon atoms, e.g. cyclopropyl, cyclobutyl, cyclopentyl, cyclohexyl and cycloheptyl, which may be substituted with lower alkyl, hydroxy-lower alkyl, amino-lower alkyl, and lower alkoxy-lower alkyl groups. The expression heterocyclyl means saturated or unsaturated (but not aromatic), four, five-, six- or seven-membered rings containing one or two nitrogen, oxygen or sulfur atoms which may be the same or different and which rings may be adequately substituted with lower alkyl, lower alkoxy, e.g. piperidinyl, morpholinyl, thiomorpholinyl, piperazinyl, tetrahydropyranyl, dihydropyranyl, 1,4-dioxanyl, pyrrolidinyl, tetrahydrofuranyl, dihydropyrrolyl, dihydroimidazolyl, dihydropyrazolyl, pyrazolidinyl and substituted derivatives of such rings with substituents as outlined above. The expression heteroaryl means six-membered aromatic rings containing one to four nitrogen atoms, benzo-fused six-membered aromatic rings containing one to three nitrogen atoms, five-membered aromatic rings containing one oxygen or one nitrogen or one sulfur atom, benzo-fused five-membered aromatic rings containing one oxygen or one nitrogen or one sulfur atom, five membered aromatic rings containig an oxygen and nitrogen atom and benzo fused derivatives thereof, five membred aromatic rings containing a sulfur and a nitrogen atom and benzo fused derivatives thereof, five-membered aromatic rings containing two nitrogen atoms and benzo fused derivatives thereof, five membered aromatic rings containing three nitrogen atoms and benzo fused derivatives thereof or the tetrazolyl ring; e.g. furanyl, thienyl, pyrrolyl, pyridinyl, pyrimidinyl, indolyl, quinolinyl, isoquinolinyl, imidazolyl, triazinyl, thiazinyl, thiazolyl, isothiazolyl, pyridazinyl, oxazolyl, isoxazolyl, 5-oxo-1,2,4-oxadiazolyl, 5-oxo-1,2,4-thiadiazolyl, 5-thioxo-1,2,4-oxadiazolyl, 2-oxo-1,2,3,5-oxathiadiazolyl, whereby such rings may be substituted with lower alkyl, lower alkenyl, amino, amino-lower alkyl, halogen, hydroxy, lower alkoxy, trifluoromethoxy, trifluoromethyl, carboxyl, carboxamidyl, thioamidyl, amidinyl, lower alkoxy-carbonyl, cyano, hydroxy-lower alkyl, lower alkyl-oxy-lower alkyl or another heteroaryl- or heterocyclyl-ring. The expression aryl represents unsubstituted as well as mono-, di- or tri-substituted aromatic rings with 6 to 10 carbon atoms like phenyl or naphthyl rings which may be substituted with aryl, halogen, hydroxy, lower alkyl, lower alkenyl, lower alkynyl, lower alkoxy, lower alkenyloxy, lower alkynyl-lower alkyl-oxy, lower alkenylen, lower alkylenoxy or lower alkylendioxy forming with the phenyl ring a five- or six-membered ring, hydroxy-lower alkyl, hydroxy-lower alkenyl, hydroxy-lower alkyl-lower alkynyl, lower alkyloxy-lower alkyl, lower alkyloxy-lower alkyloxy, trifluoromethyl, trifluoromethoxy, cycloalkyl, hydroxy-cycloalkyl, heterocyclyl, heteroaryl.

The expression pharmaceutically acceptable salts encompasses either salts with inorganic acids or organic acids like hydrohalogenic acids, e.g. hydrochloric or hydrobromic acid; sulfuric acid, phosphoric acid, nitric acid, citric acid, formic acid, acetic acid, maleic acid, tartaric acid, methylsulfonic acid, p-toluolsulfonic acid and the like or in case the compound of formula I is acidic in nature with an inorganic base like an alkali or earth alkali base, e.g. sodium hydroxide, potassium hydroxide, calcium hydroxide and the like.

The compounds of the general formula I might have one or more asymmetric carbon atoms and may be prepared in form of optically pure enantiomers or diastereomers, mixtures of enantiomers or diastereomers, diastereomeric racemates, mixtures of diastereomeric racemates and also in the meso-form. The present invention encompasses all these forms. Mixtures may be separated in a manner known per se, i.e. by column chromatography, thin layer chromatography, HPLC or crystallization.

Because of their ability to inhibit the endothelin binding, the described compounds of the general formula I and their pharmaceutically acceptable salts may be used for treatment of diseases which are associated with an increase in vasoconstriction, proliferation or inflammation due to endothelin. Examples of such diseases are hypertension, coronary diseases, cardiac insufficiency, renal and myocardial ischemia, renal failure, cerebral ischemia, dementia, migraine, subarachnoidal hemorrhage, Raynaud's syndrome, portal hypertension and pulmonary hypertension. They can also be used for the treatment or prevention of atherosclerosis, restenosis after balloon or stent angioplasty, inflammation, stomach and duodenal ulcer, cancer, prostatic hypertrophy, erectile dysfunction, hearing loss, amaurosis, chronic bronchitis, asthma, gram negative septicemia, shock, sickle cell anemia, glomerulonephritis, renal colic, glaucoma, therapy and prophylaxis of diabetic complications, complications of vascular or cardiac surgery or after organ transplantation, complications of cyclosporin treatment, pain, hyperlipidemia as well as other diseases presently known to be related to endothelin.

These compositions may be administered in enteral or oral form e.g. as tablets, dragees, gelatine capsules, emulsions, solutions or suspensions, in nasal form like sprays or rectally in form of suppositories. These compounds may also be administered intramuscularly, parenterally or intravenously, e.g. in form of injectable solutions.

These pharmaceutical compositions may contain the compounds of formula I as well as their pharmaceutically acceptable salts in combination with inorganic and/or organic excipients which are usual in the pharmaceutical industry like lactose, maize or derivatives thereof, talcum, stearinic acid or salts of these materials.

For gelatine capsules vegetable oils, waxes, fats, liquid or half-liquid polyols may be used. For the preparation of solutions and sirups e.g. water, polyols, saccharose, glucose can be used. Injectables can be prepared by using e.g. water, polyols, alcohols, glycerin, vegetable oils, lecithin or liposomes. Suppositories may be prepared by using natural or hydrogenated oils, waxes, fatty acids (fats), liquid or half-liquid polyols.

The compositions may contain in addition preservatives, stability improving substances, viscosity improving or regulating substances, solubility improving substances, sweeteners, dyes, taste improving compounds, salts to change the osmotic pressure, buffer or anti-oxidants.

The compounds of general formula I may also be used in combination with one or more other therapeutically useful substances e.g. α- and β-blockers like phentolamine, phenoxybenzamine, atenolol, propranolol, timolol, metoprolol, carteolol and the like; vasodilators like hydralazine, minoxidil, diazoxide or flosequinan; calcium-antagonists like diltiazem, nicardipine, nimodipine, verapamil or nifedipine; ACE-inhibitors like cilazapril, captopril, enalapril, lisinopril and the like; potassium activators like pinacidil; angiotensin II receptor antagonists like losartan, valsartan, irbesartan and the like; diuretics like hydrochlorothiazide, chlorothiazide, acetolamide, bumetanide, furosemide, metolazone or chlortalidone; sympatholitics like methyldopa, clonidine, gutanabenz or reserpine and other therapeutics which serve to treat high blood pressure or any cardiac disorders.

The dosage may vary within wide limits but should be adapted to the specific situation. In general the dosage given daily in oral form should be between about 3 mg and about 3 g, preferably between about 10 mg and about 1 g, especially preferred between 5 mg and 300 mg, per adult with a body weight of about 70 kg. The dosage should be administered preferably in 1 to 3 doses per day which are of equal weight. As usual children should receive lower doses which are adapted to body weight and age.

Preferred compounds are compounds of general formula I wherein $R^3$ represents phenyl or mono-substituted phenyl substituted with lower alkyloxy, especially methoxy and X represents oxygen and optically pure enantiomers or diastereomers, mixtures of enantiomers or diastereomers, diastereomeric racemates, mixtures of diastereomeric racemates and the meso-forms and pharmaceutically acceptable salts thereof.

A second group of preferred compounds of general formula I are those wherein $R^3$ represents phenyl or mono-substituted phenyl substituted with lower alkoxy, especially methoxy, X represents oxygen and $R^2$ represents —CH$^2$)$_n$—Y—R$^a$ and optically pure enantiomers or diastereomers, mixtures of enantiomers or diastereomers, diastereomeric racemates, mixtures of diastereomeric racemates and the meso-forms and pharmaceutically acceptable salts thereof.

A third group of preferred compounds of general formula I are those wherein $R^3$ represents phenyl or mono-substituted phenyl substituted with lower alkoxy, especially methoxy, X represents oxygen and $R^2$ represents —CH$_2$)$_2$—O—$R^a$, with $R^a$ being heteroaryl and optically pure enantiomers or diastereomers, mixtures of enantiomers or diastereomers, diastereomeric racemates, mixtures of diastereomeric racemates and the meso-forms and pharmaceutically acceptable salts thereof.

Another group of preferred compounds are compounds of formula II

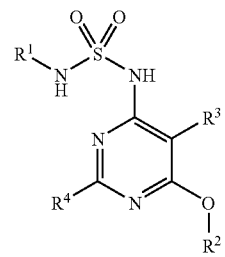

Formula II wherein $R^1$, $R^2$, $R^3$ and $R^4$ are as defined in general formula I above and optically pure enantiomers or diastereomers, mixtures of enantiomers or diastereomers, diastereomeric racemates, mixtures of diastereomeric racemates and the meso-forms and pharmaceutically acceptable salts of compounds of formula II.

Also preferred are compounds of formula III

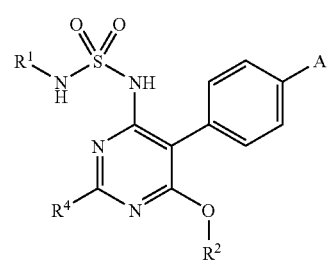

Formula III wherein $R^1$, $R^2$ and $R^4$ are as defined in general formula I above and A represents hydrogen, methyl, ethyl, chlorine, bromine, fluorine, trifluoromethyl or methoxy and optically pure enantiomers or diastereomers, mixtures of enantiomers or diastereomers, diastereomeric racemates, mixtures of diastereomeric racemates and the meso-forms and pharmaceutically acceptable salts of compounds of formula III.

Also preferred are compounds of formula IV

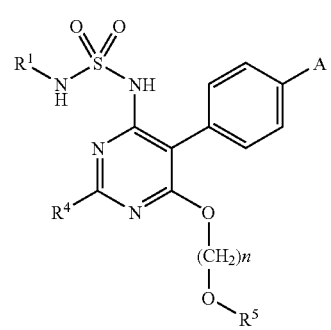

Formula IV wherein $R^1$, $R^4$ and n are as defined in general formula I above and A is as defined in formula III above and $R^5$ represents hydrogen, lower alkyl, aryl, heteroaryl and cycloalkyl, and optically pure enantiomers or diastereomers, mixtures of enantiomers or diastereomers, diastereomeric racemates, mixtures of diastereomeric racemates and the meso-forms and pharmaceutically acceptable salts of compounds of formula IV.

Another especially preferred group of compounds are compounds of formula V

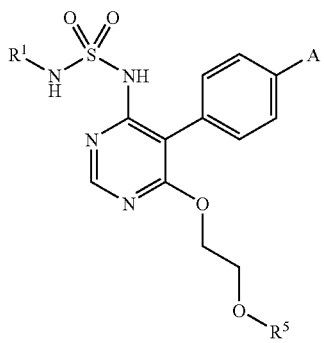

Formula V wherein $R^1$ is as defined in general formula I above, A is as defined in formula III above and $R^5$ represents hydrogen, lower alkyl, aryl, heteroaryl and cycloalkyl, and optically pure enantiomers or diastereomers, mixtures of enantiomers or diastereomers, diastereomeric racemates, mixtures of diastereomeric racemates and the meso-forms and pharmaceutically acceptable salts of compounds of formula IV.

Especially preferred compounds among the group of compounds of formula V are those wherein $R^5$ represents heteroaryl and optically pure enantiomers or diastereomers, mixtures of enantiomers or diastereomers, diastereomeric racemates, mixtures of diastereomeric racemates and the meso-forms and pharmaceutically acceptable salts thereof.

Preferred compounds are:

Pyridin-2-yl-carbamic acid 2-[5-(2-methoxy-phenoxy)-6-(benzylsulfamic acid amido)[2,2]bipyrimidinyl-4-yloxy]-ethyl ester;

Pyridin-2-yl-carbamic acid 2-[5-(2-methoxy-phenoxy)-6-(4-methoxy-benzylsulfamic acid amido)[2,2]bipyrimidinyl-4-yloxy]-ethyl ester;

Benzylsulfamic acid [6-[2-(5-bromo-pyrimidin-2-yloxy)-ethoxy]-5-(2-methoxy-phenoxy)[2,2]bipyrimidinyl-4-yl]-amide;

Cyclopropylmethylsulfamic acid [6-[2-(5-bromo-pyrimidin-2-yloxy)-ethoxy]-5-(2-methoxy-phenoxy)[2,2']bipyrimidinyl-4-yl]-amide;

Furan-2-yl-methylsulfamic acid [6-[2-(5-bromo-pyrimidin-2-yloxy)-ethoxy]-5-(2-methoxy-phenoxy)-[2,2]bipyrimidinyl-4-yl]-amide;

Cyclopropylsulfamic acid [6-[2-(5-bromo-pyrimidin-2-yloxy)-ethoxy]-5-(2-methoxy-phenoxy)[2,2]bipyrimidinyl-4-yl]-amide;

Benzylsulfamic acid-[6-[2-(5-bromo-pyrimidin-2-yloxy)-ethoxy]-5-(2-methoxy-phenoxy)-pyrimidin-4-yl]-amide;

Benzylsulfamic acid-[5-(2-chloro-5-methoxy-phenoxy)-6-[2-(5-methylsulfanyl-pyrimidin-2-yloxy)-ethoxy]-pyrimidin-4-yl]-amide;

Furan-2-yl-methylsulfamic acid [6-[2-(5-Bromo-pyrimidin-2-yloxy)-ethoxy]-5-(4-chloro-phenyl)-pyrimidin-4-yl]-amide;

Cyclopropylmethylsulfamic acid [5-(4-chloro-phenyl)-6-[2-(5-methoxy-pyrimidin-2-yloxy)-ethoxy]-pyrimidin-4-yl]-amide;

Cyclopropylmethylsulfamic acid [6-[2-(5-bromo-pyrimidin-2-yloxy)-ethoxy]-5-(4-chloro-phenyl)-pyrimidin-4-yl]-amide;

Cyclopropylmethylsulfamic acid [6-[2-(5-bromo-pyrimidin-2-yloxy)-ethoxy]-5-p-tolyl-pyrimidin-4-yl]-amide;

Benzylsulfamic acid [6-[2-(5-bromo-pyrimidin-2-yloxy)-ethoxy]-2-pyridin-4-yl-5-p-tolyl-pyrimidin-4-yl]-amide;

Benzylsulfamic acid [6-[2-(5-bromo-pyrimidin-2-yloxy)-ethoxy]-5-(4-chloro-phenyl)-2-pyridin-4-yl-pyrimidin-4-yl]-amide;

Ethylsulfamic acid [5-(4-chloro-phenyl)-6-[2-(5-methylsulfanyl-pyrimidin-2-yloxy)-ethoxy]-pyrimidin-4-yl]-amide;

Ethylsulfamic acid [5-(4-bromo-phenyl)-6-[2-(5-bromo-pyrimidin-2-yloxy)-ethoxy]-pyrimidin-4-yl]-amide;

Ethylsulfamic acid [5-(4-bromo-phenyl)-6-[2-(5-methylsulfanyl-pyrimidin-2-yloxy)-ethoxy]-pyrimidin-4-yl]-amide;

More preferred compounds are:

Benzylsulfamic acid [6-[2-(5-bromo-pyrimidin-2-yloxy)-ethoxy]-5-(4-chloro-phenyl)pyrimidin-4-yl]-amide;

Benzylsulfamic acid [6-[2-(5-bromo-pyrimidin-2-yloxy)-ethoxy]-5-(4-bromo-phenyl)-pyrimidin-4-yl]-amide;

2-Pyridylmethylsulfamic acid [6-[2-(5-bromo-pyrimidin-2-yloxy)-ethoxy]-5-(4-chloro-phenyl)pyrimidin-4-yl]-amide;

2-Thienylmethylsulfamic acid [6-[2-(5-bromo-pyrimidin-2-yloxy)-ethoxy]-5-(4-chloro-phenyl)pyrimidin-4-yl]-amide;

Benzylsulfamic acid [5-(2-chloro-5-methoxy-phenoxy)-6-[2-(5-bromo-pyrimidin-2-yloxy)-ethoxy]-pyrimidin-4-yl]-amide;

Most preferred compounds are:

Benzylsulfamic acid [6-[2-(5-methylsulfanyl-pyrimidin-2-yloxy)-ethoxy]-5-(4-bromo-phenyl)-pyrimidin-4-yl]-amide;

Ethylsulfamic acid [5-(4-chloro-phenyl)-6-[2-(5-bromo-pyrimidin-2-yloxy)-ethoxy]-pyrimidin-4-yl]-amide;

and pharmaceutically acceptable salts thereof.

Another group of preferred compounds is depicted below:

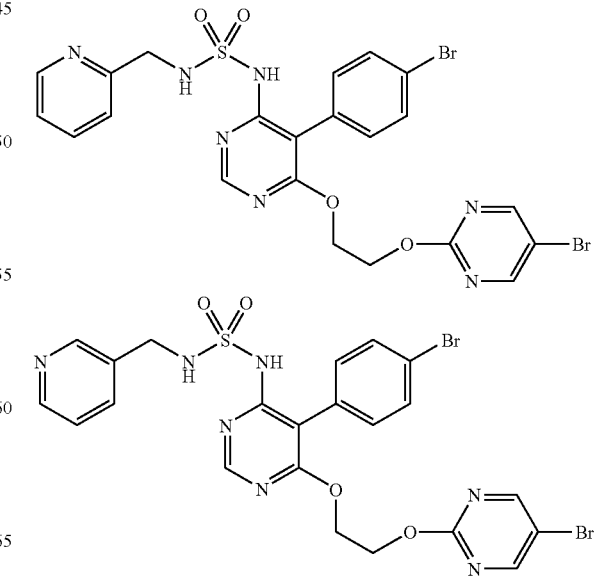

-continued
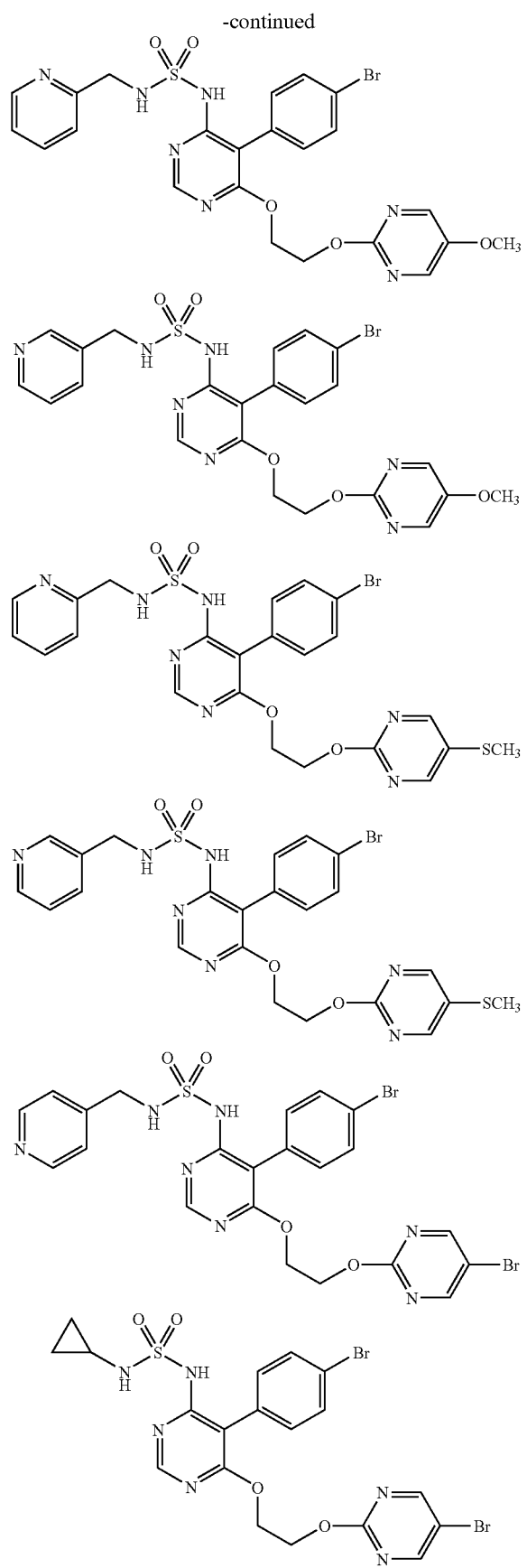
-continued
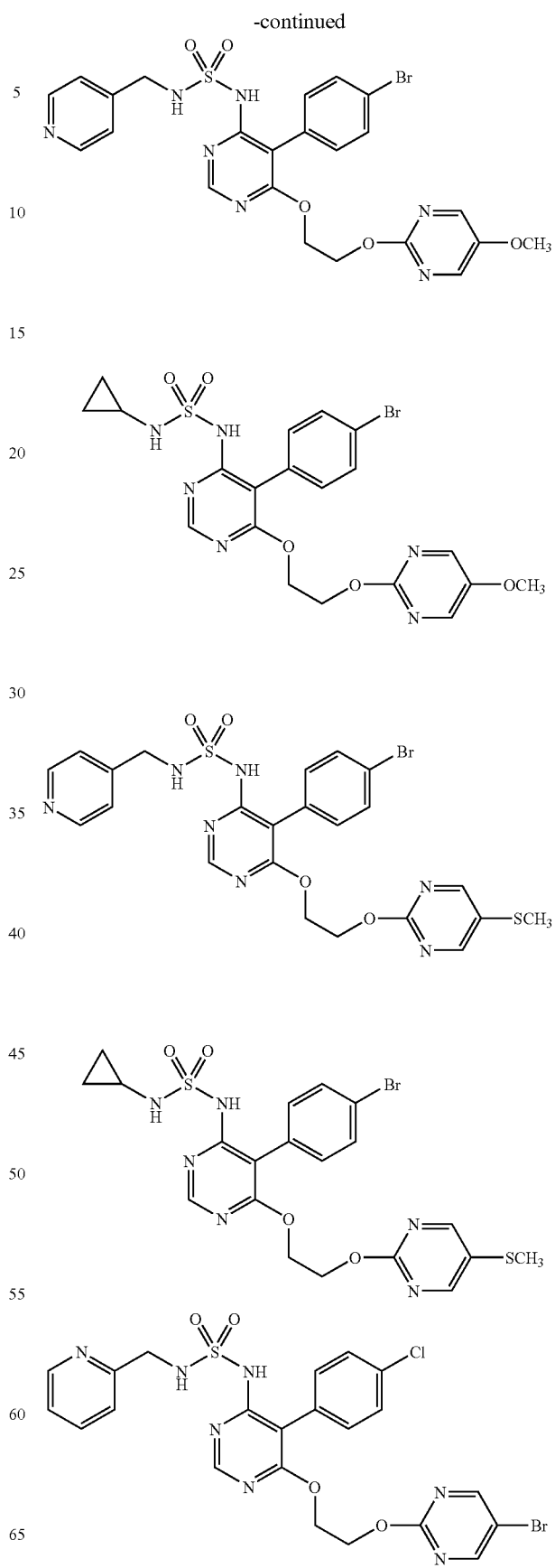

-continued
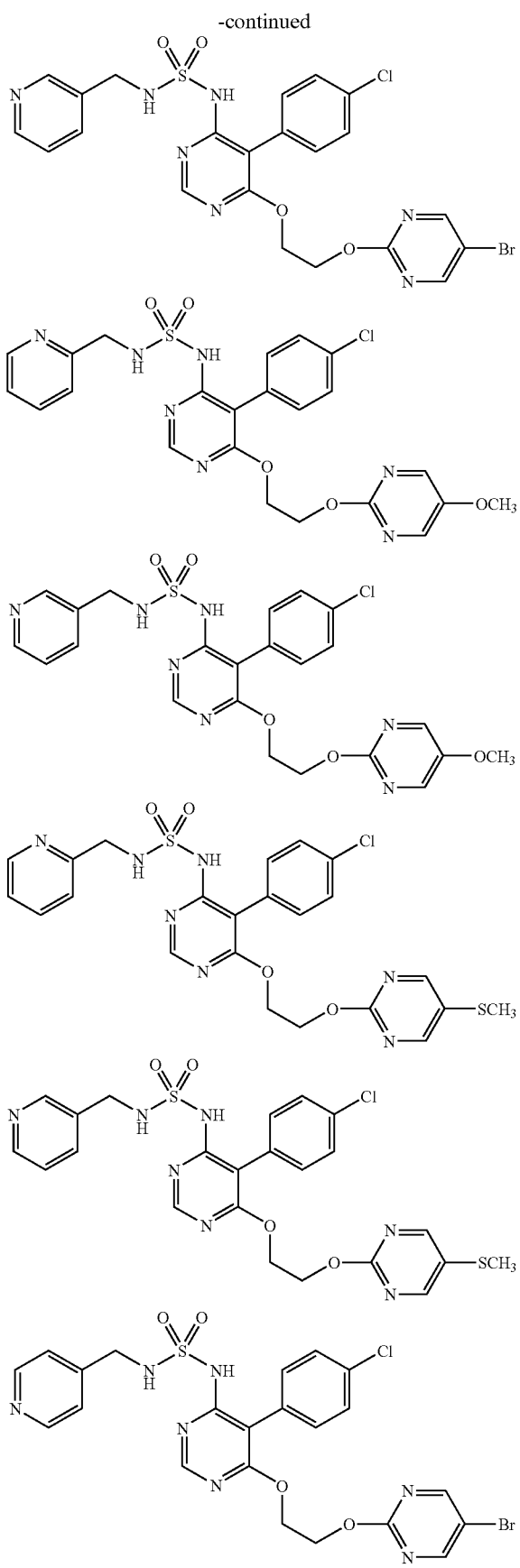
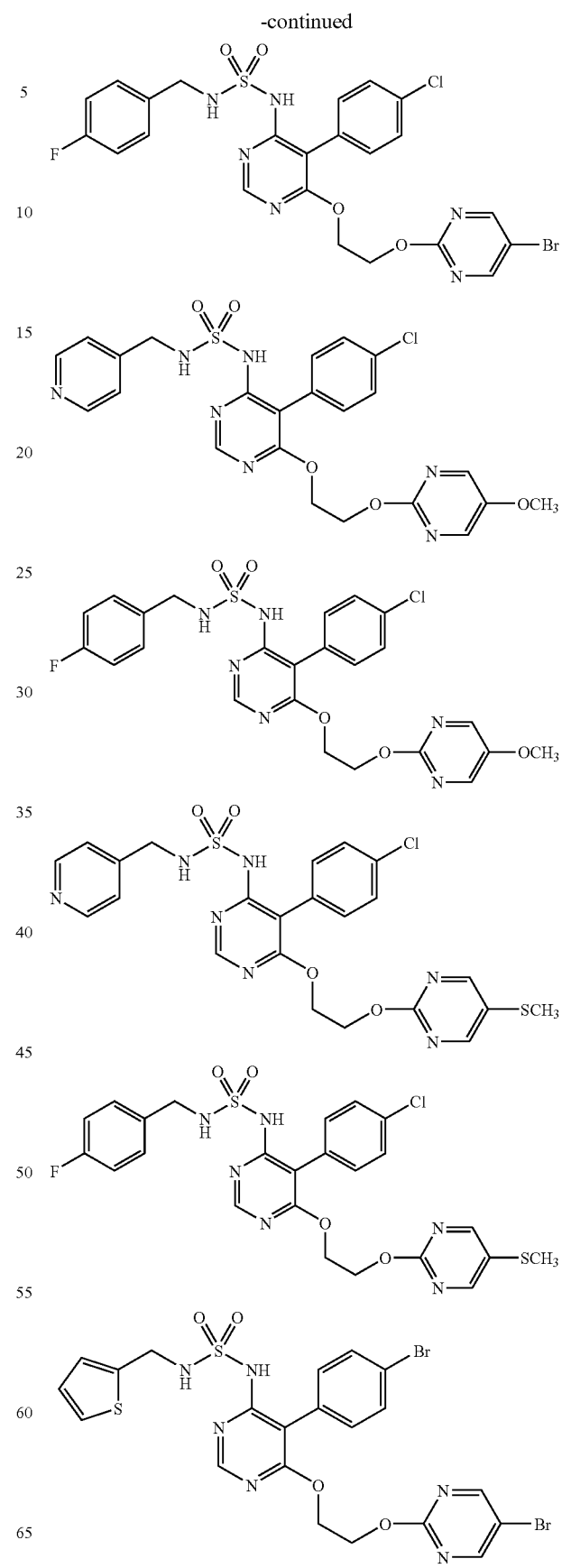

-continued
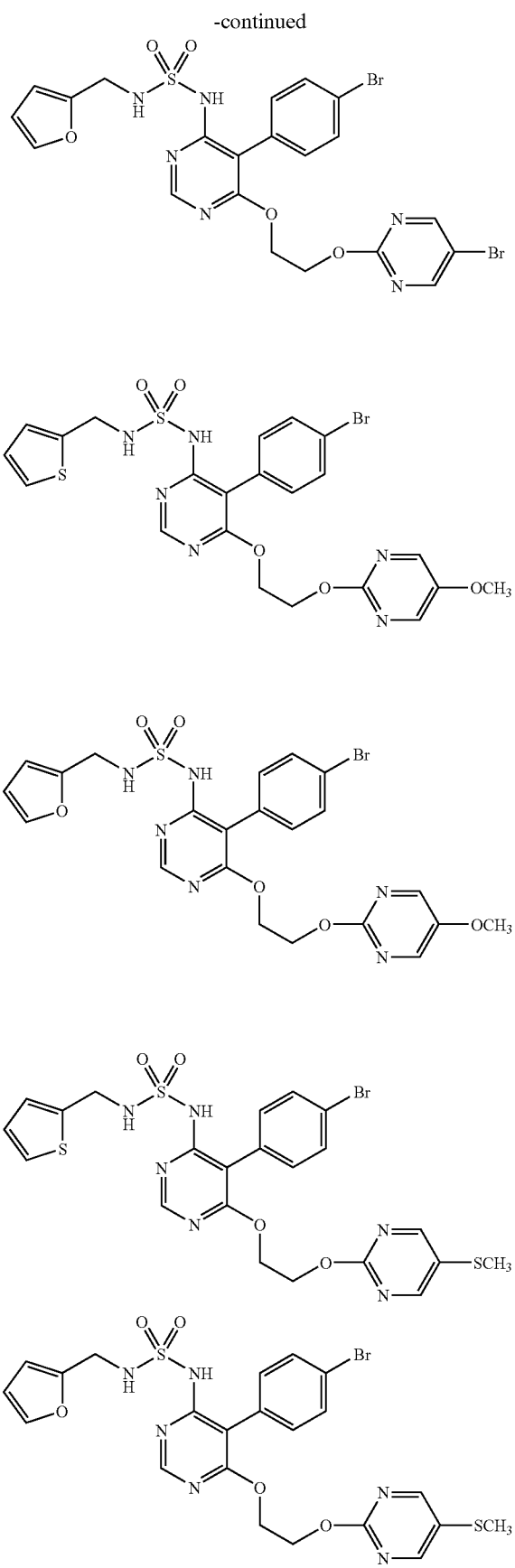
-continued
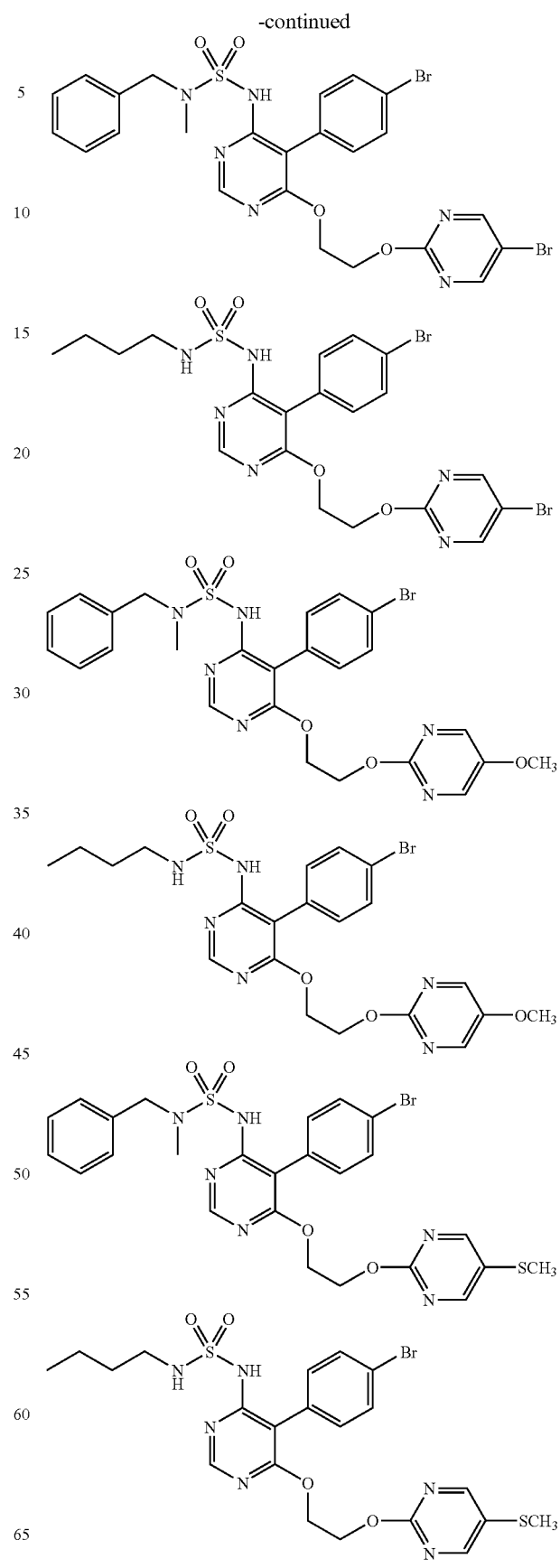

-continued
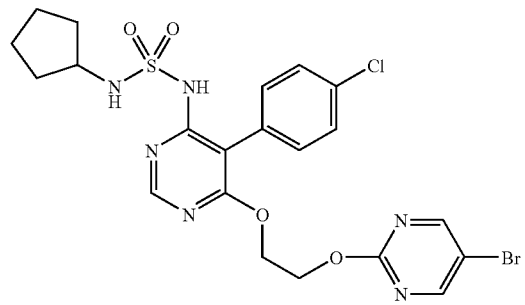
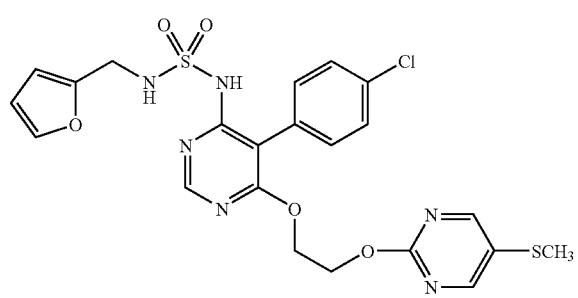
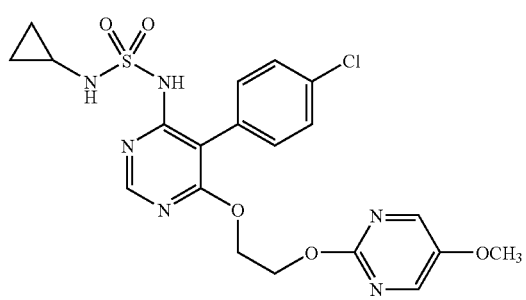
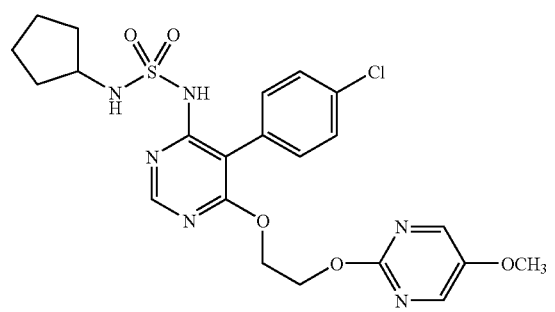
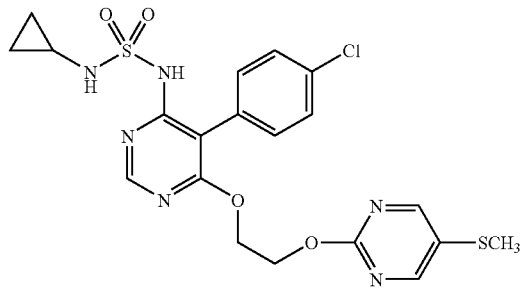
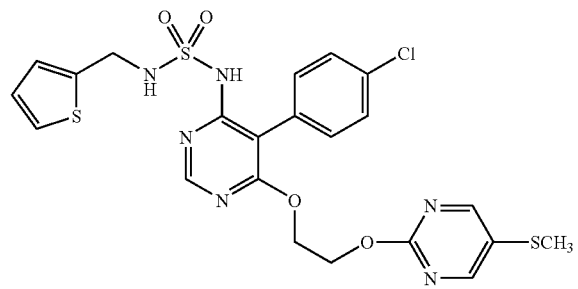
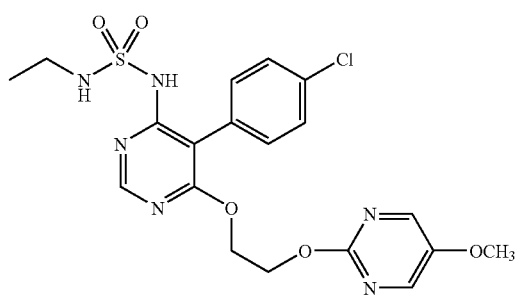
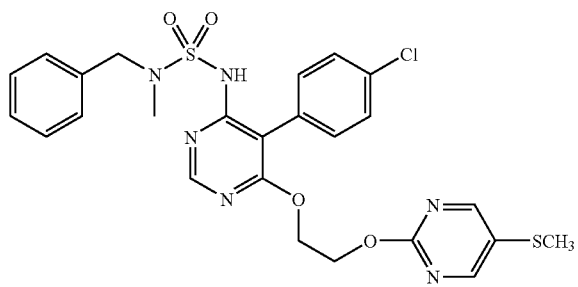
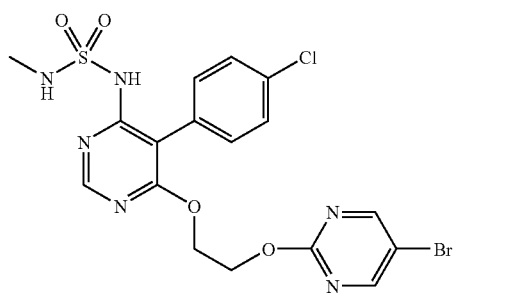

21
-continued
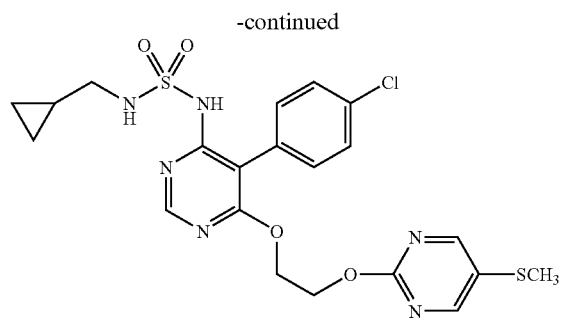
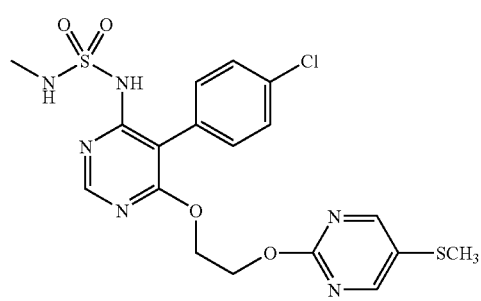
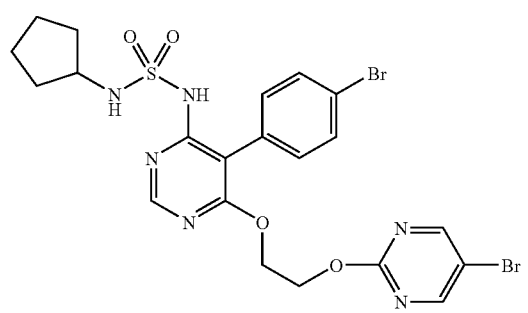
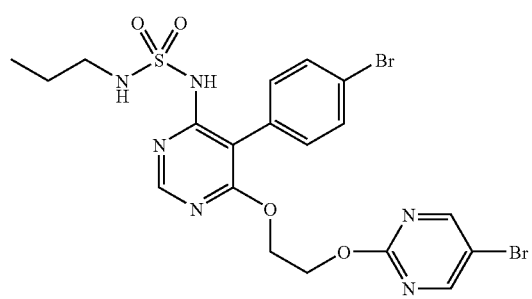
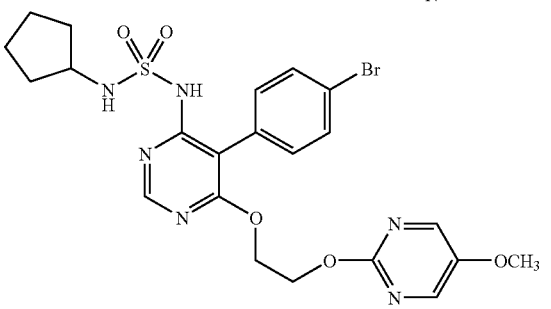
22
-continued
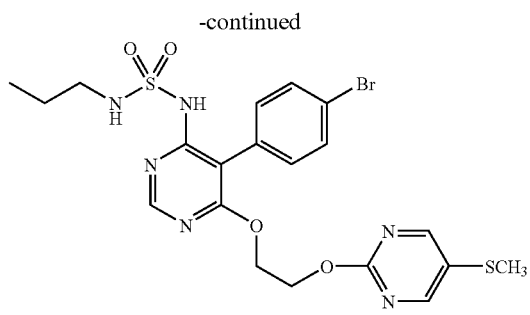
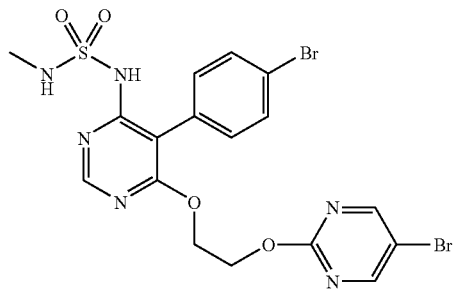
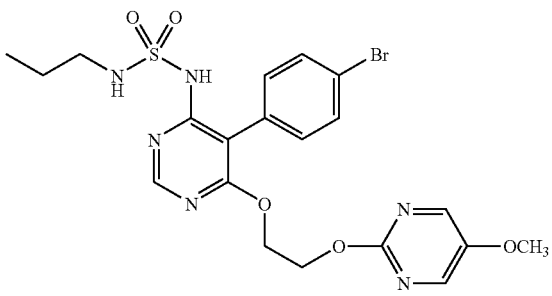
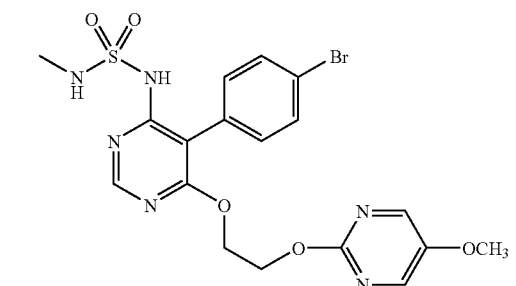
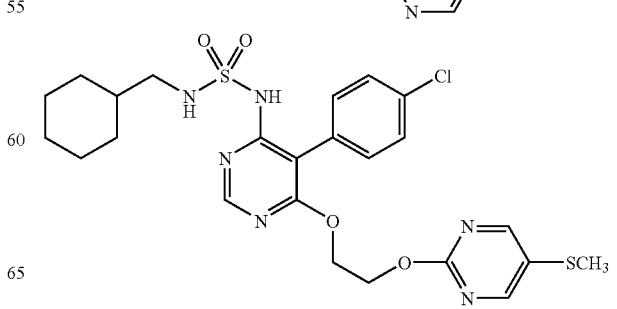

-continued

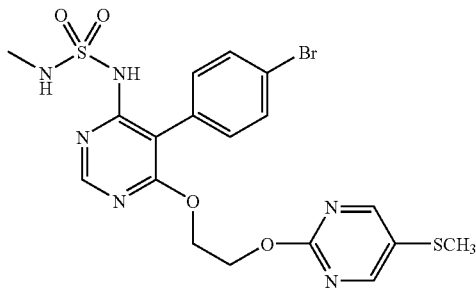

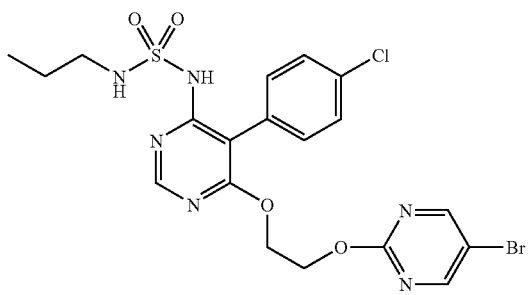

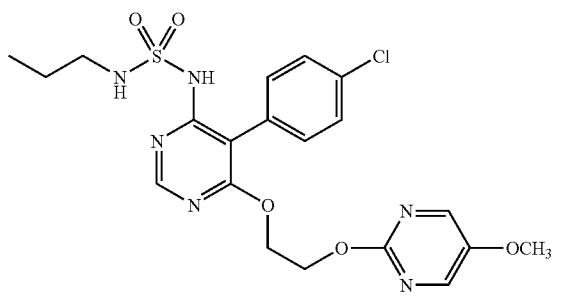

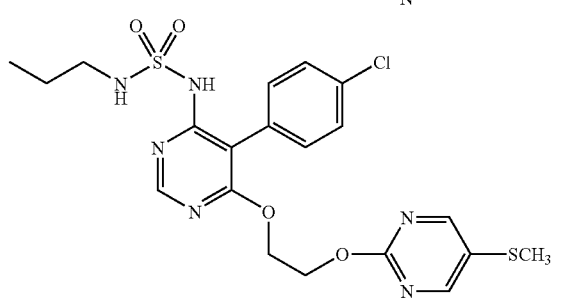

Compounds of the general formula I of the present invention can be prepared according to the general sequence of reactions outlined below. For simplicity and clarity reasons sometimes only parts of the synthetic possibilities which lead to compounds of general formula I are described. The literature references given in brackets [ ] are set forth at the end of this paragraph.

Possibility A:

The desired compounds of general formula I can be prepared by reacting a compound of the formula 1:

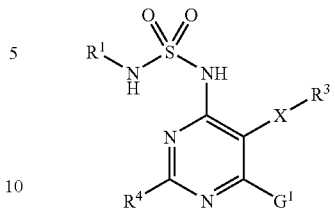

Formula 1 wherein $G^1$ is a reactive residue, preferentially a chloro atom, and the other symbols are as defined in general formula I above, with a compound of the formula 2:

$R^2$—OH      Formula 2 wherein the symbols are the same as defined in general formula I above, or a salt thereof.

Possibility B:

The compounds of general formula I may also be prepared by reacting a compound of formula 3:

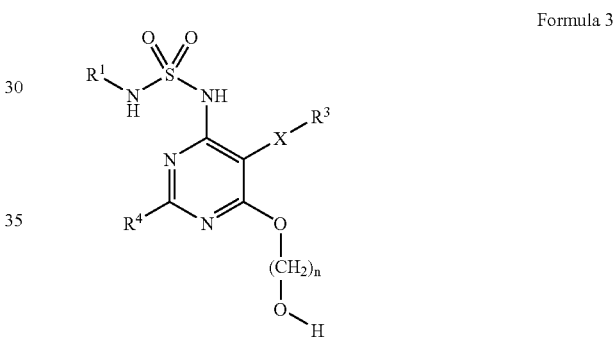

Formula 3 wherein the symbols are the same as defined in general formula I above, or a salt thereof, with a compound of the formula 4:

$G^2$-$R^5$      Formula 4 wherein $G^2$ is a reactive residue, preferentially a halogen atom, and $R^5$ is the same as defined in formula IV above.

Possibility C:

The compounds of general formula I may also be prepared by reacting a compound of the formula 5:

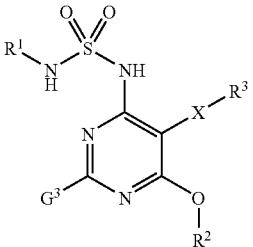

Formula 5

Wherein $G^3$ is a lower alkylsulfonyl group or a phenylsulfonyl group or a halogen atom, and the other symbols are the same as described in general formula I above, or a salt thereof, with a compound of the formula 6:
R[4']—H   Formula 6
wherein $R^{4'}$ represents:
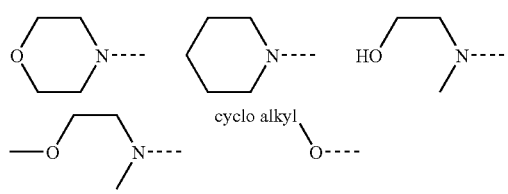
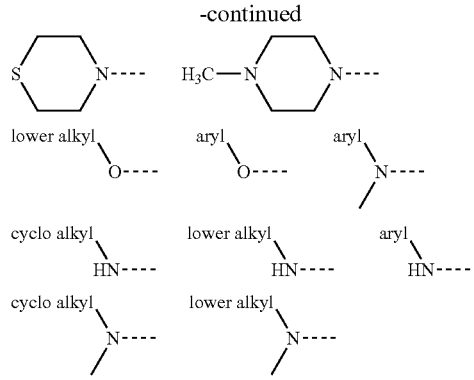
For possibilities A to C see also [5]
Scheme 1: Schematically exemplified synthesis of Example 3 and Example 5:
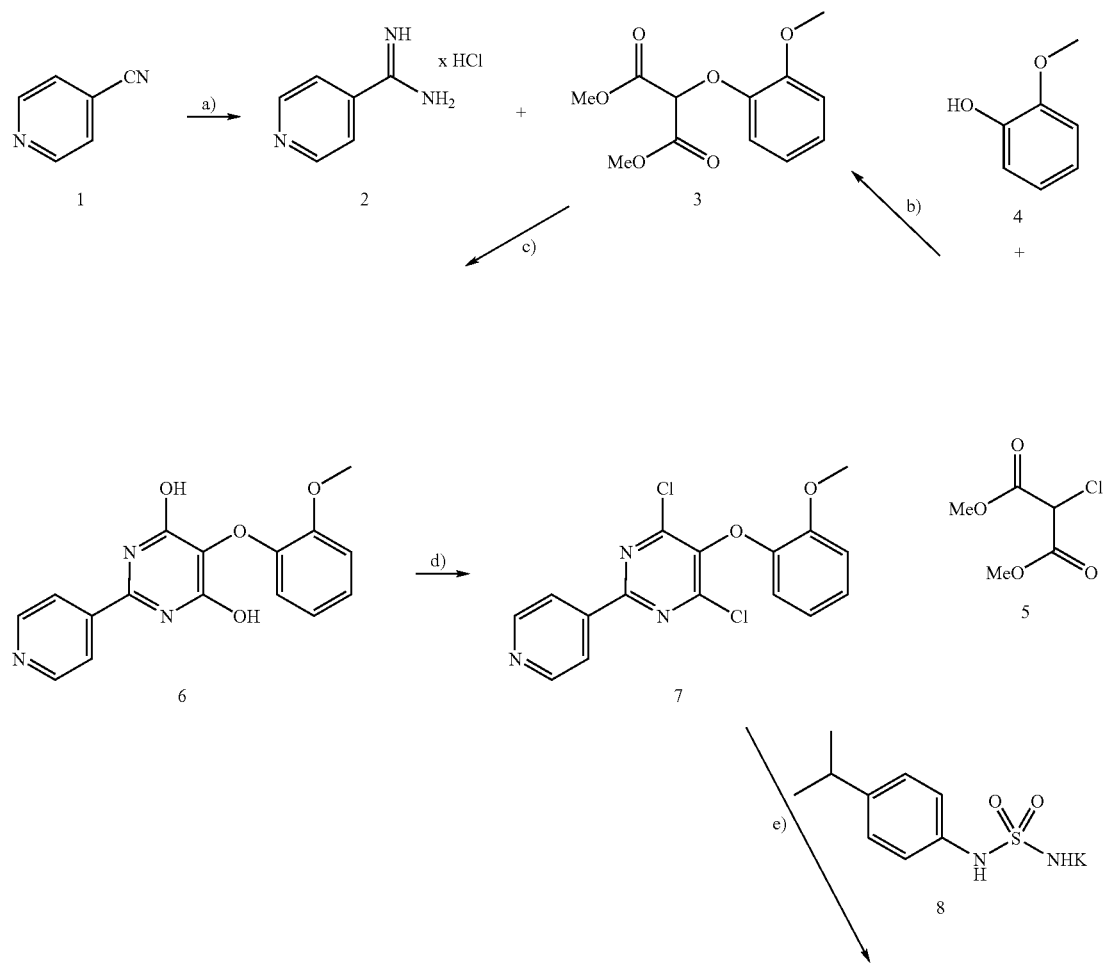

-continued

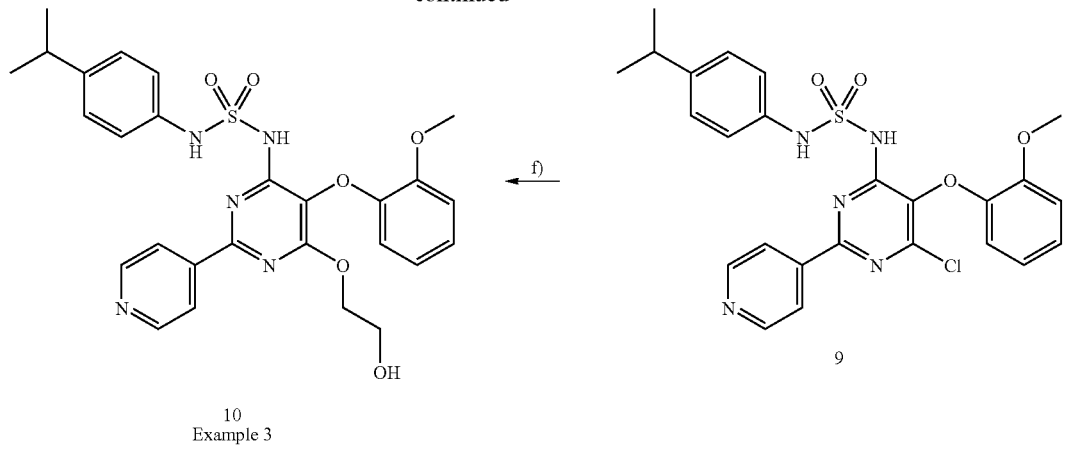

10
Example 3

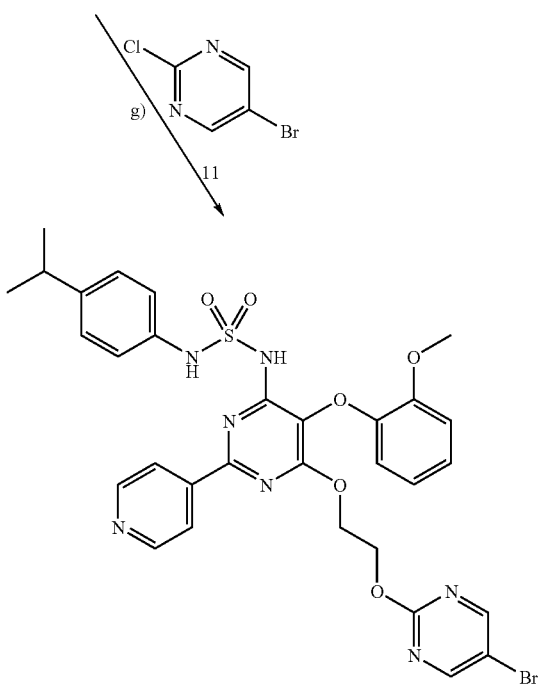

12
Example 5 a) NaOMe, MeOH then NH₄Cl; b) K₂CO₃, acetone, rflx; c) NaOMe, MeOH; d) POCl₃, N,N-dimethylaniline, 70-130° C.; e) 8, DMSO; f) Na, ethyleneglycol; 80-100° C.; g) 11, THF, NaH, rt - 70° C.

In Scheme 1 the synthetic procedure to prepare compounds of the general formula I is depicted by the description of the synthesis of Example 3 and Example 5. The other examples given in this document can be prepared via the same synthetic pathway, adapting the substituents and reaction conditions. The literature references given in [ ] are set forth at the end of this paragraph. The amidines 2 were synthesized applying standard methodology [1] by reaction of the appropriate nitrile 1 with sodium methylate in methanol followed by addition of ammonium chloride. The 2-substituted malonic esters 3 were prepared according to published procedures [2] by reacting dimethylchloromalonate (5) with the appropriate alcohol 4 in acetone and potassium carbonate as base. The compounds 3 were dissolved in methanol, sodium methylate was added, and stirring was continued for about 30 min followed by the addition of an amidine derivative 2. Stirring at ambient temperature was continued for another 8 h. After acidic work up the 4,6-dihydroxypyrimidines 6 could be isolated in yields of 70 to 90% [2]. Compounds 6 or the tautomeric form thereof were transformed into the dichloro derivatives 7 with phosphorus oxychloride in the presence of N,N-dimethylaniline at elevated temperatures (60-120° C.) in yields of 40 to 75% [3]. The dichlorides 7 were reacted with an excess of the appropriate sulfamide potassium salt 8 (prepared as described in Scheme 3) in DMSO at r.t. or 40 to 60° C. to give the monochloro-pyrimidines 9 in yields of 70 to 90% either after recrystallization from ethyl acetate/diethylether or chromatography through silica gel with ethyl acetate/heptane. The pyrimidine derivatives 9 are then reacted with ethylene glycol (or another 1-ω-diol, or a mono alcohol) in the presence of a base like potassium tert.-butylate, sodium hydride or sodium at 80-110° C. for 4 to 16 h to give compounds 10 as the first claimed compounds in yields of 50 to 70%, which can be further transformed to compounds 12 by reaction with 2-chloro-5-bromopyrimidine (11) (or another suitable pyrimidine or pyridine derivative) in THF/DMF ~5/1 at either r.t. or at 50-70° C. in yields of 50-80%.

Scheme 2: Schematically exemplified synthesis of Examples 47, 48, 50, 51, 53:

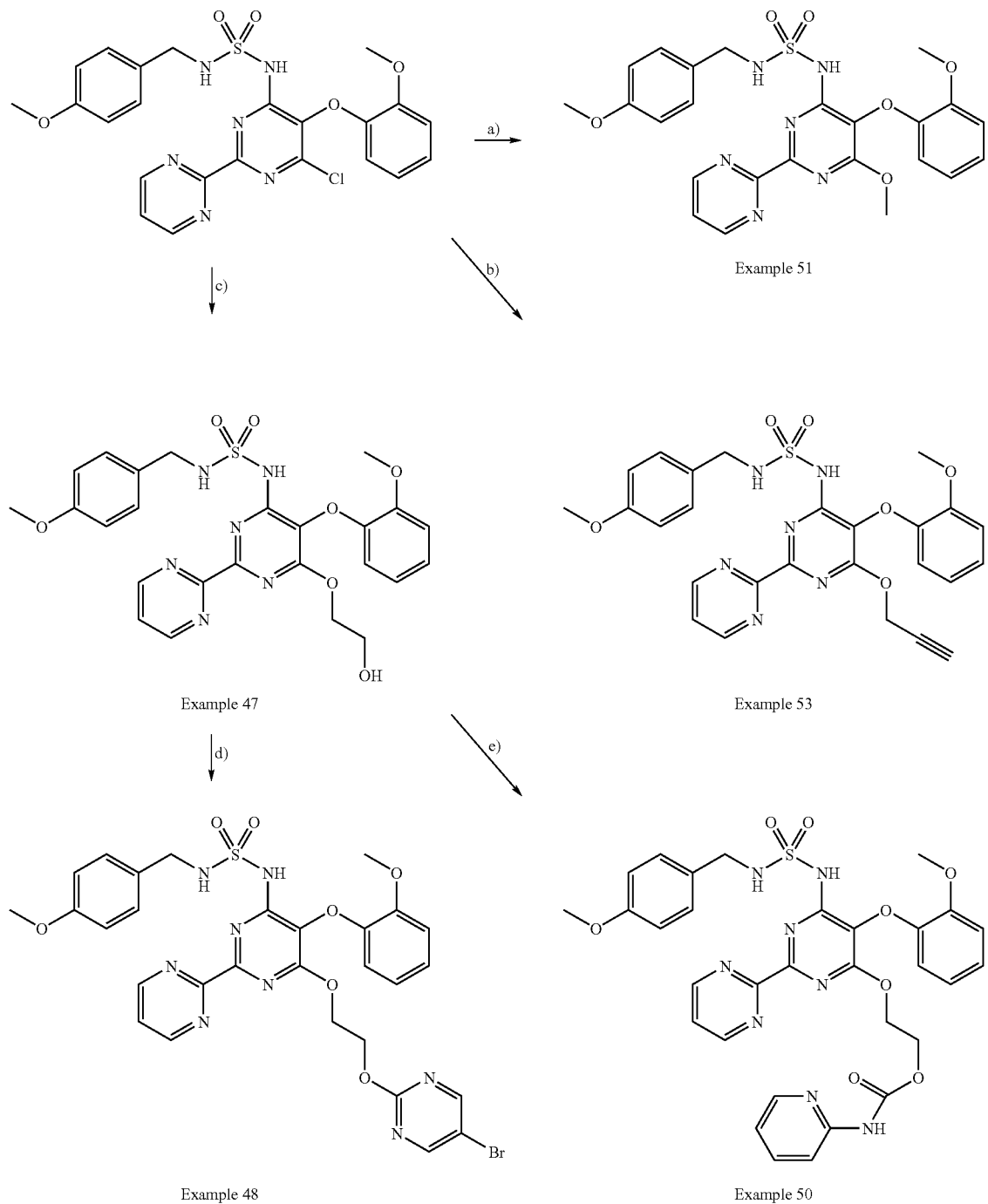

Example 51

Example 47

Example 53

Example 48

Example 50 a) NaOMe, MeOH, rflx; b) Propargylic alcohol, NaH, THF, rflx; c) Ethylene glycol, KOtBu, 110° C.; d) NaH, THF then 5-bromo-2-chloropyrimidine, 70° C.;
e) Pyridine-2-carbonyl azide, CHCl3, 70° C., 2 h then Example 47, 70° C., 16 h.

For further experimental descriptions see [1], [2], [3], [5], [6] and [9].
Scheme 3: Preparation of the sulfamide-moieties [10], [11], [12], [13], [14], [15] and [19] and preparation of substituted pyrimidines [16], [17]:
a)
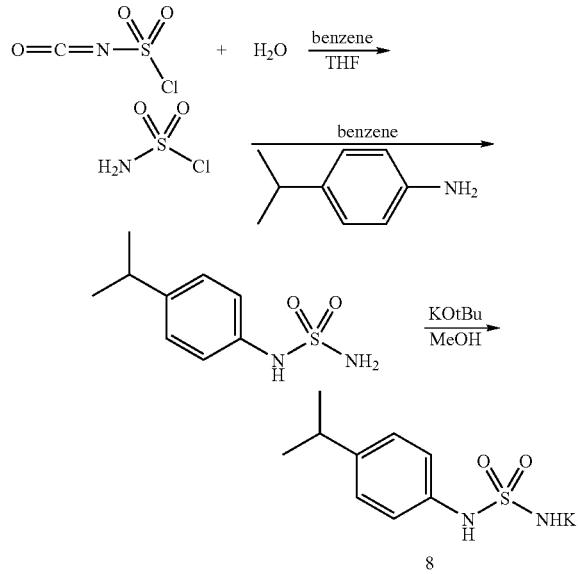
b)
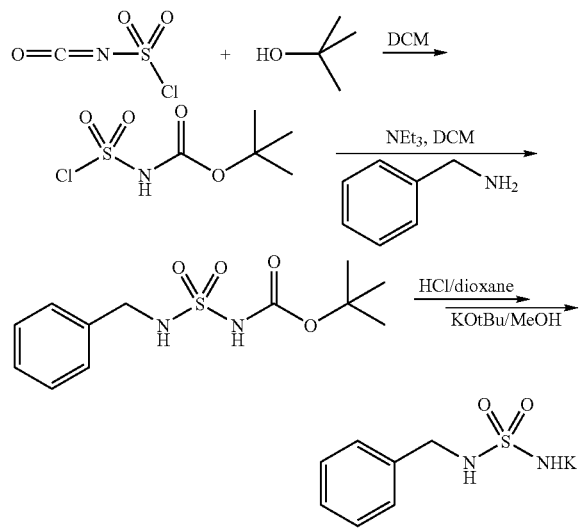
[19]
c)
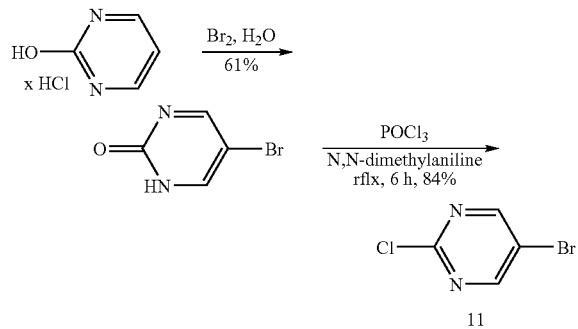
d)
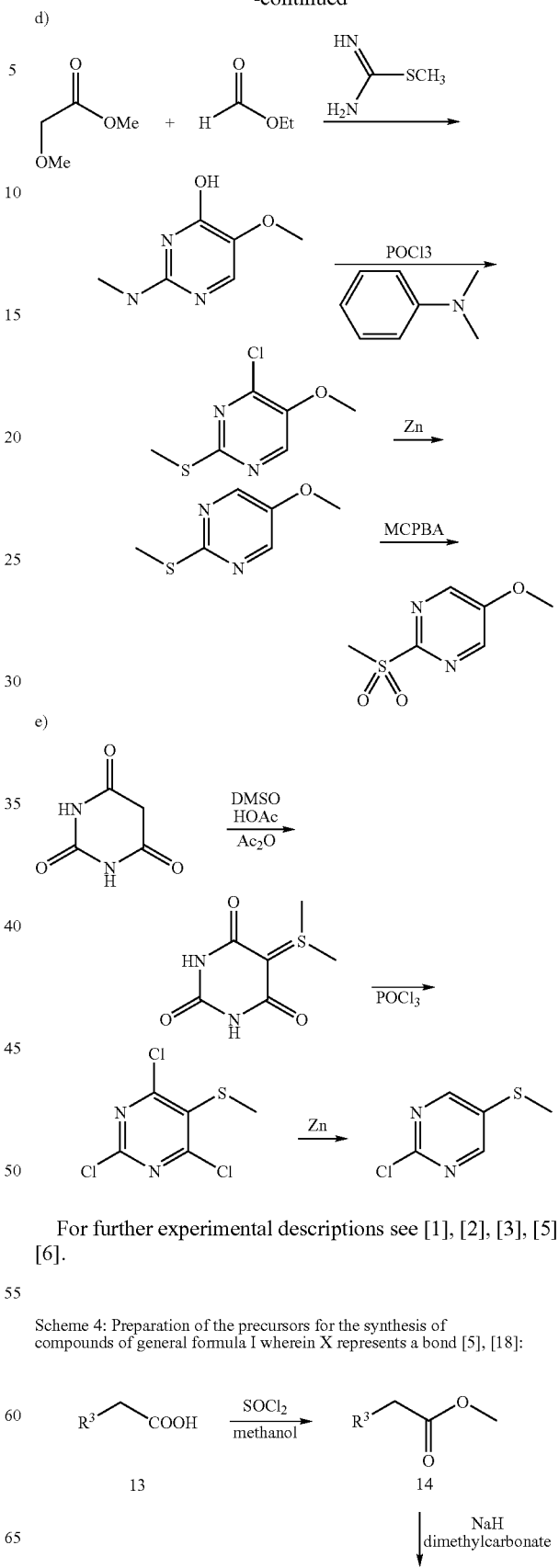
e)
For further experimental descriptions see [1], [2], [3], [5], [6].
Scheme 4: Preparation of the precursors for the synthesis of compounds of general formula I wherein X represents a bond [5], [18]:
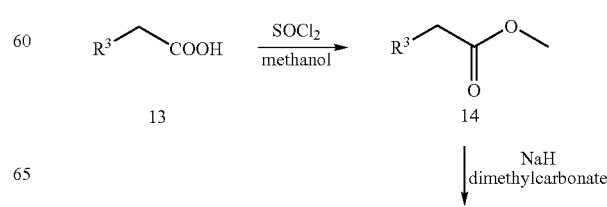

-continued

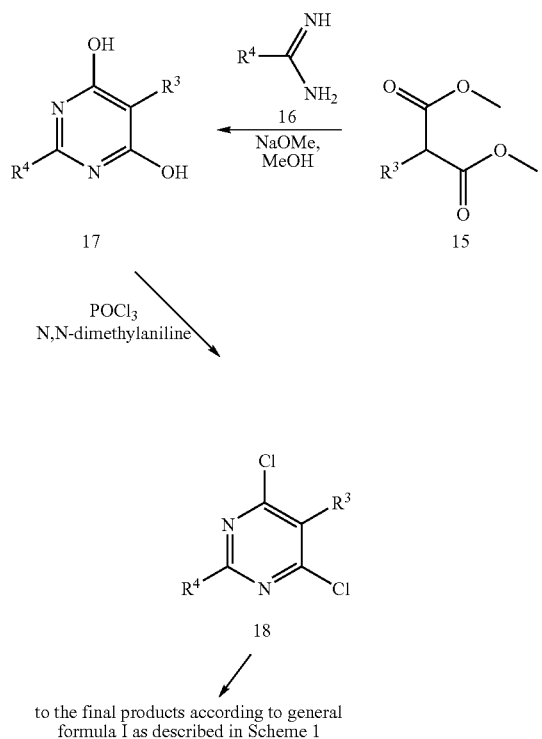

In Scheme 4 the symbols represent the same as defined in general formula I above.

[1] W. Göhring, J. Schildknecht, M. Federspiel; *Chimia*, 1996, 50, 538-543.
[2] W. Neidhart, V. Breu, D. Bur, K. Burri, M. Clozel, G. Hirth, M. Müller, H. P. Wessel, H. Ramuz; *Chimia*, 1996, 50, 519-524 and references cited there.
[3] W. Neidhart, V. Breu, K. Burri, M. Clozel, G. Hirth, U. Klinkhammer, T. Giller, H. Ramuz; *Bioorg. Med. Chem. Lett.*, 1997, 7, 2223-2228. R. A. Nugent, S. T. Schlachter, M. J. Murphy, G. J. Cleek, T. J. Poel, D. G. Whishka, D. R. Graber, Y. Yagi, B. J. Keiser, R. A. Olmsted, L. A. Kopta, S. M. Swaney, S. M. Poppe, J. Morris, W. G. Tarpley, R. C. Thomas; *J. Med. Chem.*, 1998, 41, 3793-3803.
[4] J. March; *Advanced Organic Chemistry*, 4th Ed., 1994, p. 499 and references cited there.
[5] EP 0 743 307 A1; EP 0 658 548 B1; EP 0 959 072 A1 (Tanabe Seiyaku)
[6] EP 0 633 259 B1; EP 0 526 708 A1; WO 96/19459 (F. Hoffmann-LaRoche)
[7] for the Synthesis of 5-membered heterocycles see: Y. Kohara et al; *J. Med. Chem.*, 1996, 39, 5228-5235 and references cited there.
[8] EP 0 882 719 A1 (Yamanouchi Pharmaceutical Co., Ltd)
[9] a) R. Graf; *Chem. Ber.*, 1959, 92, 509-513. b) G. Weiss, G. Schulze; *Liebigs Ann. Chem.*, 1969, 729, 40-51. c) J. A. Kloek, K. L. Leschinsky, *J. Org. Chem.*, 1976, 41, 4028-4029. d) R. P. Dickinson, K. N. Dack, C. J. Long, J. Steele; *J. Med. Chem.*, 1997, 40, 3442-3452. e) E. Cohen, B. Klarberg; *J. Am. Chem. Soc*, 1962, 84, 1994-2002.
[10] E. Cohen, B. Klarberg; *J. Am. Chem. Soc.*, 1962, 84, 1994.
[11] G. Weiss, G. Schulze, *Liebigs Ann. Chem.*, 1969, 729, 40.
[12] R. Graf, *Chem. Ber.*, 1959, 92, 509.
[13] J. A. Kloek, K. L. Leschinsky, *J. Org. Chem.*, 1976, 41, 4028.
[14] R. E. Olson, T. M. Sielecki, et al; *J. Med. Chem.*, 1999; 42, 1178.
[15] R. P. Dickinson, K. N. Dack, et al; *J. Med. Chem.*, 1997; 40, 3442.
[16] D. G. Crosby, R. V. Berthold; *J. Org. Chem.*, 1960; 25; 1916.
[17] Bayer AG (Maurer, F.; Hammann, I.; Behrenz, W.); U.S. Pat. No. 4,233,294 1980.
[18] E. D. Morgan; *Tetrahedron*, 1967, 23, 1735.
[19] M. J. Tozer, I. M. Buck et al.; *Bioorg. Med. Chem. Lett.*, 1999, 9, 3103. G. Dewynter et al.; *Tetrahedron*, 1993, 49, 65.

EXAMPLES

The following examples illustrate the invention. All temperatures are stated in ° C.

List of Abbreviations:

EtOAc ethyl acetate

CyHex cyclohexane

Hex hexane

DMSO dimethylsulfoxide

THF tetrahydrofuran

MCPBA m-chloroperbenzoic-acid

DMF dimethylformamide

DCM dichloromethane

HV high vacuum conditions rt room temperature $t_R$ retention time min minutes

DBU 1,8-diazabicyclo[5.4.0]undec-7-en(1,5-5)

DMAP 4-dimethylaminopyridine rflx reflux

The following compounds were prepared according to the procedure described above and shown in Schemes 1 to 4. All compounds were characterized by 1H-NMR (300 MHz) and occasionally by 13C-NMR (75 MHz) (Varian Oxford, 300 MHz; chemical shifts are given in ppm relative to the solvent used; multiplicities: s=singlet, d=doublet, t=triplet; m=multiplet), by LC-MS (Waters Micromass; ZMD-platform with ESI-probe with Alliance 2790 HT; Column: 2×30 mm, Gromsil ODS4, 3 μm, 120 A; Gradient: 0-100% acetonitril in water, 6 min, with 0.05% formic acid, flow: 0.45 ml/min; $t_R$ is given in min.), by TLC (TLC-plates from Merck, Silica gel 60 $F_{254}$) and occasionally by melting point.

REFERENTIAL EXAMPLES (SYNTHESIS OF THE PRECURSORS)

Referential Example 1

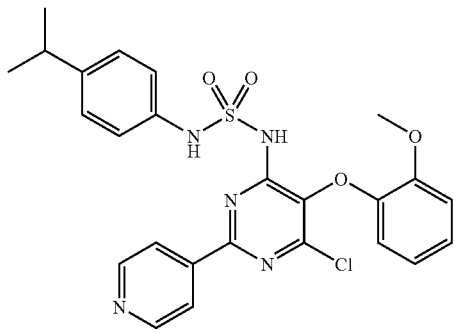

a) To a solution of sodium (0.23 g) in methanol (40 ml) was added 4-cyanopyridine (10.62 g) at r.t. Stirring was continued for 6 h followed by the addition of ammonium-chloride (5.9 g) and stirring was continued for another 10 h. Then, diethylether (120 ml) was added and the precipitate was filtered off after 30 min and washed with diethylether (20 ml). The product was dried under high vacuum. 4-Amidino-pyridine hydrochloride (14.95 g) was obtained as a white powder.

b) 2-Methoxy-phenol (guaiacol) (48 ml) was slowly added to a stirred suspension of potassium carbonate (70.8 g) in acetone (480 ml) followed by heating to 45° C. Then, dimethylchloromalonate (63.2 ml) in acetone (50 ml) was added within 20 min. The reaction mixture was heated to reflux for 16 h. The solvent was evaporated under reduced pressure, the residue taken into water and extracted with DCM. The combined organic layers were dried over sodium sulfate and evaporated. The oily product was crystallized from tert.-butyl-methyl-ether. Dimethyl-(o-methoxyphenoxy)malonate (86 g) was obtained.

c) To a stirred solution of sodium methylate (9.7 g) in methanol (100 ml) a solution of dimethyl-(o-methoxyphenoxy)malonate (21.7 g) in methanol (50 ml) was added within 15 min and stirring was continued for 30 min followed by the addition of 4-amidino-pyridine hydrochloride (15.0 g) and stirring at r.t. for 20 h. The reaction mixture was concentrated in vacuo. The solid residue was stirred with ether. The obtained powder was filtered off and dissolved in water (300 ml). Acetic acid was added to pH=4. The precipitated product was filtered off, washed with water and dried in vacuo at 50° C. 5-(o-Methoxyphenoxy)-4,6-dihydroxy-2-(4-pyridyl)-pyrimidine (20.1 g) (is possibly also present as the tautomeric 5-(o-methoxyphenoxy)-2-(4-pyridyl)-tetrahydropyrimidine-4,6-dion) was obtained as a white powder.

d) 5-(o-Methoxyphenoxy)-4,6-dihydroxy-2-(4-pyridyl)-pyrimidine (10 g), N-diisopropylethylamine (11.2 g), tetraethylammoniumchloride (11 g) and phosphorus pentachloride (13.8 g) were dissolved in phosphorus oxychloride (25 ml) and heated to reflux for 3 h. The mixture was evaporated in vacuo, toluene was added and the mixture was again evaporated. The residue was taken into DCM and poured onto ice/water. The layers were separated, the organic layer was washed with water, dried over sodium sulfate and evaporated. After recrystallization from acetone, 4,6-dichloro-5-(o-methoxyphenoxy)-2-(4-pyridyl)-pyrimidine (6.52 g) was obtained.

e) To a solution of 4-i-propyl-phenyl sulfamic acid amide (642 mg; Referential Example 17) in DMF (9 ml) was added sodium hydride (250 mg). The mixture was warmed to 45° C. for 30 min. Then, 4,6-dichloro-5-(o-methoxyphenoxy)-2-(4-pyridyl)-pyrimidine (1.044 g) was added and the reaction mixture was stirred for 60 h at r.t. After acidic work up and chromatography over silicagel with Hex/EtOAc=2/5, 4-i-propyl-phenyl sulfamic acid-[6-chloro-5-(o-methoxyphenoxy)-2-(4-pyridyl)-4-pyrimidinyl]-amide (0.42 g) can be isolated.

Referential Example 2

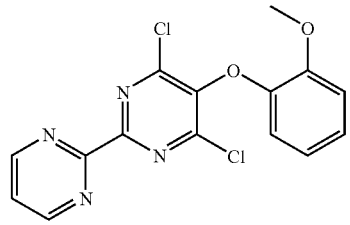

a) 4,6-Dihydroxy-5-(o-methoxyphenoxy)-2-(2-pyrimidinyl)-pyrimidine [or its tautomer 5-(o-methoxyphenoxy)-2-(2-pyrimidinyl)tetrahydropyrimidine-4,6-dion] was prepared as disclosed in EP 0 526 708 A1 from 2-amidino-pyrimidine and dimethyl-(o-methoxyphenoxy)malonate.

b) 4,6-Dichloro-5-(o-methoxyphenoxy)-2-(2-pyrimidinyl)-pyrimidine was prepared as disclosed in EP 0 526 708 A1 from 4,6-dihydroxy-5-(o-methoxyphenoxy)-2-(2-pyrimidinyl)-pyrimidine (which may also be present in the tautomeric form 5-(o-methoxyphenoxy)-2-(2-pyrimidinyl)-tetrahydro-pyrimidine-4,6-dione).

Referential Example 3

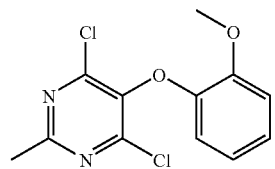

a) A solution of dimethyl-(o-methoxyphenoxy)malonate (10 g) in dry methanol (80 ml) was cooled to 0° C. Sodium methylate (6.71 g) was added portionwise. To the suspension was added of acetamidine hydrochloride (2.84 g) and the mixture was stirred overnight at r.t. The solvent was removed under reduced pressure and the residue was suspended in diethyl ether (100 ml). The solid was filtered off, washed with another portion of diethyl ether (100 ml) and dissolved in water (50 ml). The pH was adjusted to 4 by adding glacial acetic acid (25 ml). The white precipitate that formed was filtered off, washed with water and dried to yield 5-(o-methoxyphenoxy)-4,6-dihydroxy-2-methyl-pyrimidine (5.17 g) (or a tautomer) as a white powder.

b) A solution of 5-(o-methoxyphenoxy)-4,6-dihydroxy-2-methyl-pyrimidine (10.9 g) (or a tautomer) in POCl₃ (150 ml) was stirred at 50° C. for 72 h. The excess of POCl₃ was evaporated, toluene was added to coevaporate traces of POCl₃. Eventually, an ice/water mixture was carefully added to the residue and the pH was adjusted to 8 using 3 N sodium hydroxide solution. The mixture was further diluted with water (300 ml) and extracted with DCM (500 ml). The organic layer was separated, washed with water (300 ml), dried over Na₂SO₄ and evaporated. The residue was dissolved again in DCM and filtered through a pad of silica gel eluting with DCM. The solvent was removed in vacuo. The resulting residue was dried to furnish 4,6-dichloro-5-(o-methoxyphenoxy)-2-methyl-pyrimidine (8.7 g) as a beige powder.

Referential Example 4

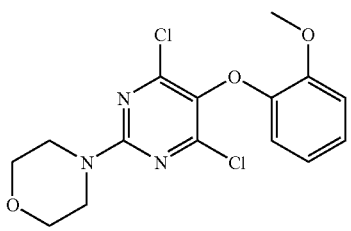

a) A solution of dimethyl-(o-methoxyphenoxy)malonate (32.75 g) in methanol (250 ml) was cooled to 0° C. Sodium methylate (20.0 g) was added portionwise and upon completion of the addition the mixture was stirred at r.t. for 6 h. Then morpholinoformamidine hydrobromide (25.0 g) was added and stirring was continued for 72 h. The solvent of the beige suspension was evaporated and the residue was washed twice with diethyl ether (150 ml). The remaining powder was dissolved in water (200 ml). Upon adjusting the pH to 4 with acetic acid (50 ml) a precipitate formed. The precipitate was collected, washed with water and dried under high vacuum to yield 5-(o-methoxyphenoxy)-4,6-dihydroxy-2-(N-morpholino)-pyrimidine (17.01 g) (or a tautomer) as a slightly beige powder.

b) At 0° C. POCl₃ (50 ml) was carefully added to Hünig's base (27.5 ml). To this mixture 5-(o-methoxyphenoxy)-4,6-dihydroxy-2-(N-morpholino)-pyrimidine (17 g) was added portionwise. The resulting mixture was stirred over night at 130° C. The excess of reagents was evaporated and traces of POCl₃ were removed by coevaporation with toluene. The black residue was treated with DCM (50 ml) and a water/ice mixture (50 ml). After stirring for 15 min, the mixture was diluted with water (400 ml) and DCM (400 ml). The organic layer was separated and washed with water (300 ml). The aqueous layer was extracted with DCM (400 ml). The combined DCM layers were dried over Na₂SO₄ and the solvent was removed to a volume of about 100 ml. The remaining solution was filtered over silica gel (50 g) eluting with DCM. The filtrate was evaporated. The resulting residue was suspended in diethyl ether (50 ml). The solid was filtered off and dried to give 4,6-dichloro-5-(o-methoxyphenoxy)-2-(N-morpholino)-pyrimidine (13.85 g) as a white crystalline powder.

Referential Example 5

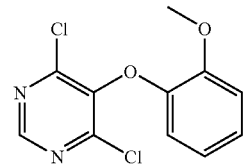

a) At 5° C. sodium methylate (12.7 g) was added portionwise to a solution of dimethyl-(o-methoxyphenoxy)malonate (18.9 g) in methanol (450 ml). Upon completion of the addition stirring was continued at r.t. for 30 min followed by the addition of formamidine hydrochloride (6 g). The mixture was stirred at r.t. for 72 h. Eventually, the solvent was removed under reduced pressure and the remaining residue was suspended in diethyl ether. The solid material was filtered off and dissolved in water (100 ml). The solution was acidified with conc. hydrochloric acid. A white precipitate formed. The precipitate was collected, washed with water and dried to give 5-(o-methoxyphenoxy)-4,6-dihydroxy-pyrimidine (15.1 g) (or a tautomer) as a white powder.

b) To a solution of 5-(o-methoxyphenoxy)-4,6-dihydroxy-pyrimidine (7.5 g) in POCl₃ (90 ml) N,N-dimethylaniline (24 ml) was added. The mixture was heated to 160° C. and stirred for 2.5 h. Excess of POCl₃ was distilled off under reduced pressure. Traces of POCl₃ were coevaporated with toluene. The remaining oil was treated with a water:ice mixture. The mixture was acidified with 1 N hydrochloric acid and extracted twice with diethyl ether. The combined organic layers were washed twice with dilute aqueous hydrochloric acid, dried over MgSO₄ and evaporated. The remaining solid was washed with methanol and dried. This gave 4,6-dichloro-5-(o-methoxyphenoxy)-pyrimidine (4.75 g) as a pale yellow powder.

Referential Example 6

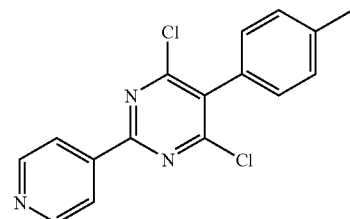

a) A solution of sodium methylate (6.8 g) in methanol (200 ml) was cooled to 0° C. A solution of diethyl 2-(p-tolyl)-malonate. (10.3 g) in methanol (50 ml) was slowly added. Upon completion of the addition the solution was allowed to warm to r.t. and 4-amidino-pyridine hydrochloride (7.57 g) was added. The mixture was stirred at r.t. for 16 h. Eventually, the solvent was removed under reduced pressure and the remaining residue was dissolved in 2 M hydrochloric acid. The solution was extracted with diethyl ether, then adjusted to pH 5 with 10 M sodium hydroxide solution. A precipitate formed. The precipitate was collected, washed with cold water and dried at 60° C. under high vacuum. This gave 4,6-dihydroxy-2-(4-pyridyl)-5-(p-tolyl)-pyrimidine (8.77 g) (or a tautomer) as orange crystals.

b) To a mixture of 4,6-dihydroxy-2-(4-pyridyl)-5-(p-tolyl)-pyrimidine (8.0 g) and POCl₃ (100 ml) diethylamine (25 ml) was added at r.t. The mixture was stirred for 16 h at 60° C. The excess of POCl₃ was distilled off under reduced pressure. The remaining oil was dissolved in DCM (300 ml) and treated with water (300 ml). The aqueous layer was separated and extracted three times with DCM. The combined organic layers were washed with water and brine, dried over MgSO₄ and evaporated. The resulting residue was suspended in isopropanol. The solid material was collected, washed with isopropanol and diethyl ether and dried to give 4,6-dichloro-2-(4-pyridyl)-5-(p-tolyl)-pyrimidine (7.2 g) as a white crystalline powder.

Referential Example 7

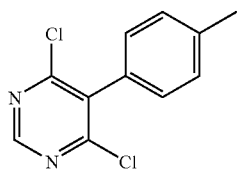

a) At 0° C. a solution of diethyl 2-(p-tolyl)-malonate (14.2 g) in methanol (50 ml) was slowly added to a solution of sodium methylate (9.4 g) in methanol (300 ml). Upon completion of the addition the reaction mixture was allowed to warm up and formamidine hydrochloride (5.4 g) was added. The mixture was stirred at r.t. for 16 h. The solvent was removed under reduced pressure and the remaining residue was treated with 2 N hydrochloric acid (150 ml). The suspension was stirred for 0.5 h. At 0-5° C., the pH was carefully adjusted to 4 using 10 N sodium hydroxide solution. The precipitate was collected, washed with cold water, isopropanol, and diethyl ether and dried under high vacuum at 65° C. to give 4,6-dihydroxy-5-(p-tolyl)-pyrimidine (11.2 g) (or a tautomer) as a white powder.

b) At r.t. N,N-dimethylaniline (10 ml) was added to a mixture of 4,6-dihydroxy-5-(p-tolyl)-pyrimidine (5.1 g) and POCl₃ (75 ml). The reaction mixture was stirred at 70° C. for 16 h. The excess of POCl₃ was distilled off and the remaining oil was treated with an ice:water mixture and extracted three times with diethyl ether. The combined organic layers were washed with 1N aqueous hydrochloric acid followed by brine, dried over MgSO₄ and evaporated. The remaining brown oil was crystallised from isopropanol. The pale yellow crystals were collected, washed with cold isopropanol and dried under high vacuum to furnish 4,6-dichloro-5-(p-tolyl)-pyrimidine (4.1 g).

Referential Example 8

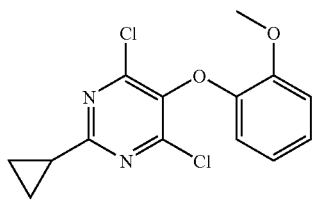

a) To a solution of sodium (5.17 g) in methanol (200 ml) dimethyl-(2-methoxyphenoxy)malonate (21.1 g) was added and the mixture was stirred at r.t. for 30 min. To the slurry, cyclopropylamidine hydrochloride (12.0 g) was added. The mixture was stirred at r.t. for 22 h. Eventually, the solvent was removed in vacuo. The remaining residue was suspended in diethyl ether (250 ml). The diethyl ether was decanted and the remaining solid was dissolved in water (250 ml). The solution was acidified with 25% aqueous hydrochloric acid. The precipitate that formed was collected, washed with water and dried at 60° C. under high vacuum to give 5-(2-methoxyphenoxy)-4,6-dihydroxy-2-cyclopropyl-pyrimidine (19.26 g) as a colourless powder. LC-MS: $t_R$=2.74 min, [M+1]⁺=275.24, [M−1]⁻=273.29.

b) To a suspension of 5-(2-methoxyphenoxy)-4,6-dihydroxy-2-cyclopropyl-pyrimidine (8.22 g) in POCl₃ (87 ml), N,N-dimethylaniline (12 ml) was added. The mixture became clear and was stirred at 130° C. for 3.5 h. Excess POCl₃ was removed in vacuo, remaining traces of POCl₃ were coevaporated with toluene. The remaining sirup was poured on an ice-water mixture and the resulting solution was extracted three times with diethyl ether. The organic layers were combined, washed once with 1 N aqueous hydrochloric acid and twice with water, treated with activated charcoal, dried over MgSO₄ and evaporated. The residue was crystallised from a diethyl ether/hexane to give 4,6-dichloro-2-cyclopropyl-5-(2-methoxyphenoxy)-pyrimidine (6.64 g) as a beige powder. LC-MS: $t_R$=5.36 min, [M+1]⁺=311.19.

Referential Example 9

According to procedures described in Referential Examples 1 to 8 and in the literature [2], [3], [5], [6] and [8], the following 4,6-dichloropyrimidine precursors were prepared.

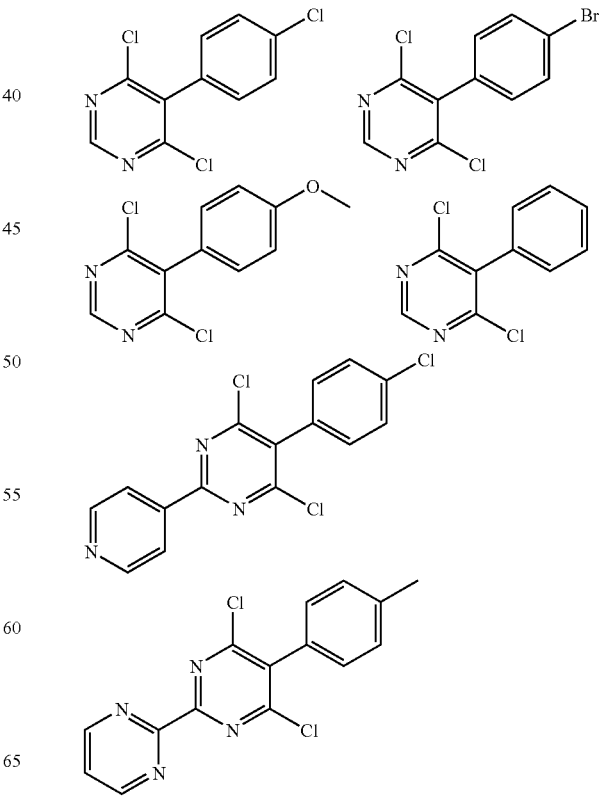

-continued

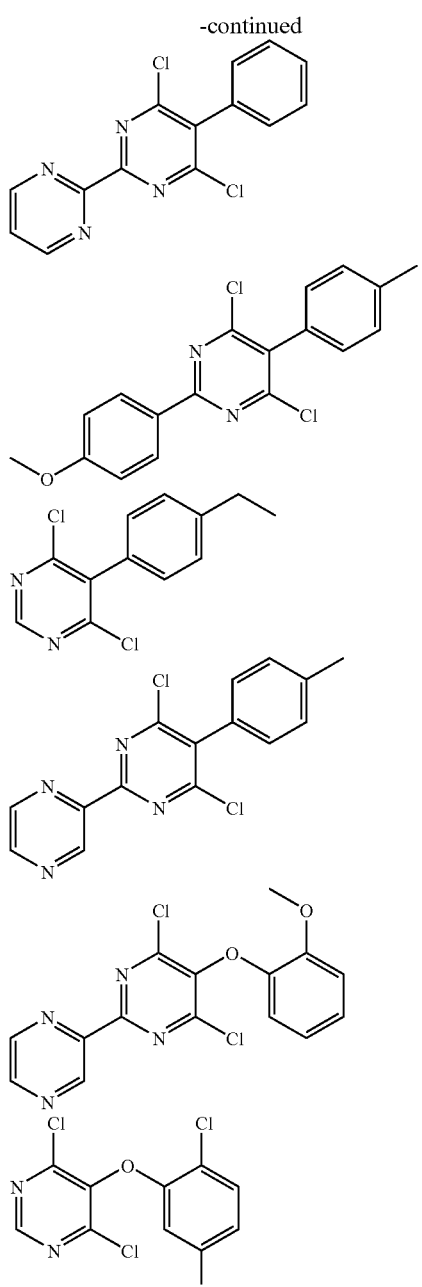

Referential Example 10

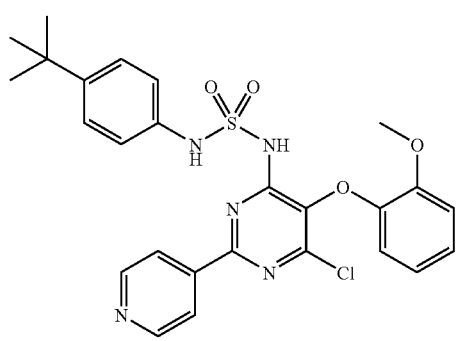

To a solution of 4-t-butyl-phenyl sulfamic acid amide (228 mg, Referential Example 18) in DMF (3 ml) was added sodium hydride (42 mg). Then, 4,6-dichloro-5-(o-methoxyphenoxy)-2-(4-pyridyl)-pyrimidine (305 mg) and Hünig base (0.17 ml) was added and the reaction mixture was stirred for 5 h at 60° C. After acidic work up and crystallization, 4-t-butyl-phenyl sulfamic acid-[6-chloro-5-(o-methoxyphenoxy)-2-(4-pyridyl)-4-pyrimidinyl]-amide (0.15 g) could be isolated. $t_R$=5.54 min (LC); [M+H]$^+$=540.44 (ES+);

Referential Example 11

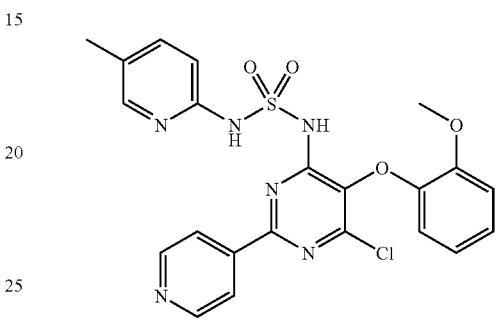

According to the procedure described in referential Example 1e), 5-methyl-pyridine-2-sulfamic acid amide (252 mg, Referential Example 20) was reacted with 4,6-dichloro-5-(o-methoxyphenoxy)-2-(4-pyridyl)-pyrimidine (410 mg, Referential Example 1d)) to give 5-methyl-pyridine-2-sulfamic acid-[6-chloro-5-(o-methoxyphenoxy)-2-(4-pyridyl)-4-pyrimidinyl]-amide (100 mg). $t_R$=4.02 min (LC); [M+H]$^+$=499.33 (ES+);

Referential Example 12

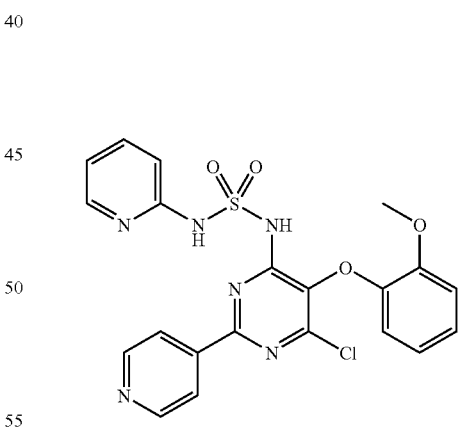

According to the procedure described in referential Example 1e), pyridine-2-sulfamic acid amide (60 mg, Referential Example 21) was reacted with 4,6-dichloro-5-(o-methoxyphenoxy)-2-(4-pyridyl)-pyrimidine (100 mg, Referential Example 1d)) to give pyridine-2-sulfamic acid-[6-chloro-5-(o-methoxyphenoxy)-2-(4-pyridyl)-4-pyrimidinyl]-amide (100 mg). $t_R$=3.83 min (LC); [M−H]$^+$=483.33 (ES−);

Referential Example 13

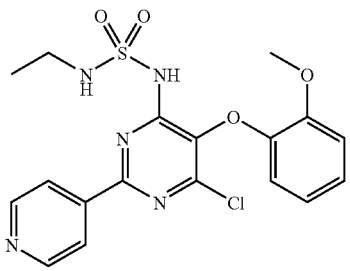

According to the procedure described in referential Example 1e), ethyl-sulfamic acid amide (40 mg, Referential Example 22) was reacted with 4,6-dichloro-5-(o-methoxyphenoxy)-2-(4-pyridyl)-pyrimidine (100 mg, Referential Example 1d)) to give pyridine-2-sulfamic acid-[6-chloro-5-(o-methoxyphenoxy)-2-(4-pyridyl)-4-pyrimidinyl]-amide (70 mg). $t_R$=4.40 min (LC); [M–H]$^+$=434.28 (ES–);

Referential Example 14

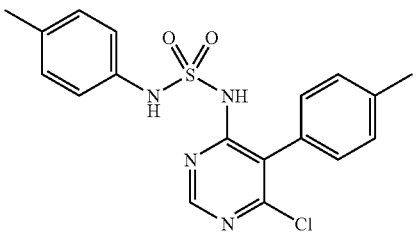

To 4,6-dichloro-5-p-tolyl-pyrimidine (Referential Example 7) (2.0 g) dissolved in DMSO (35 ml) was added di-isopropyl-ethyl-amine (1.46 ml) followed by addition of 4-methyl-phenyl sulfamic acid amide potassium salt (2.78 g) [prepared from the product described in Referential Example 19 and potassium tert.-butylate in methanol followed by evaporation of the solvent]. The mixture was stirred for 48 h at rt then poured onto water (500 ml) and diethylether (250 ml) was added and the solution was stirred for 30 min. The layers were separated and the water layer was acidified with acetic acid (2.0 ml) and cooled to 0° C. for 1 h. The precipitated product was filtered off and washed with water and diethylether and dried to give 4-methyl-phenyl sulfamic acid-[6-chloro-5-(p-tolyl)-4-pyrimidinyl]-amide (2.02 g). $t_R$=5.00 min (LC); [M+H]$^+$=389.11 (ES+);

Referential Example 15

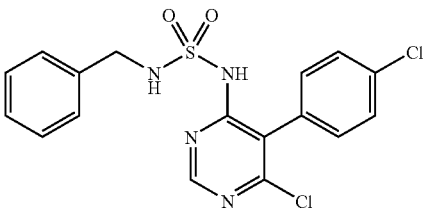

To 4,6-dichloro-5-(4-chloro-phenyl)-pyrimidine (Referential Example 9) (2.59 g) dissolved in DMSO (14 ml) was added di-isopropyl-ethyl-amine (1.8 ml) followed by the addition of benzyl sulfamic acid amide potassium salt (2.25 g) [prepared from the product described in Referential Example 22 and potassium tert.-butylate in methanol followed by the evaporation of the solvent]. The mixture was stirred for 24 h at rt then poured onto water (300 ml) and diethylether (120 ml) was added and the solution was stirred for 30 min. The layers were separated and the water layer was acidified with solid citric acid (pH=3) and cooled to 0° C. for 1 h. The precipitated product was filtered off, washed with water and recrystallized from methanol to give benzyl sulfamic acid-[6-chloro-5-(p-chloro-phenyl)-4-pyrimidinyl]-amide (1.8 g). $t_R$=4.94 min (LC); [M+H]$^+$=410.90 (ES+);

Referential Example 16

According to the procedure described for the synthesis of Referential Example 15, the following compounds could be prepared:

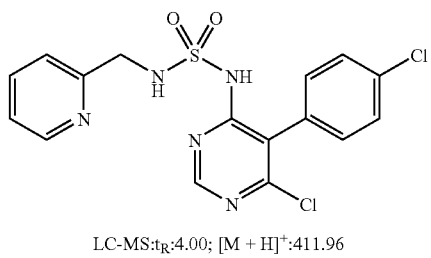

LC-MS:$t_R$:4.00; [M + H]$^+$:411.96

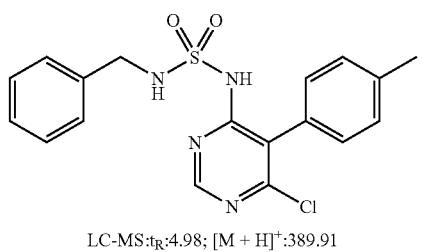

LC-MS:$t_R$:4.98; [M + H]$^+$:389.91

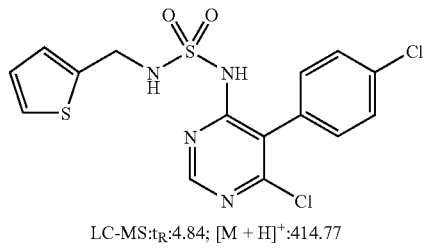

LC-MS:$t_R$:4.84; [M + H]$^+$:414.77

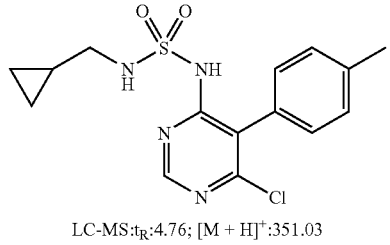

LC-MS:$t_R$:4.76; [M + H]$^+$:351.03

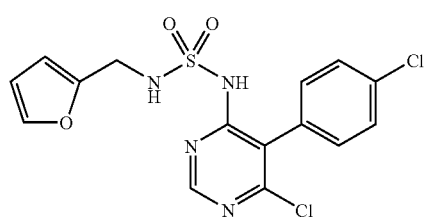
LC-MS:t$_R$:4.66; [M + H]$^+$:400.88
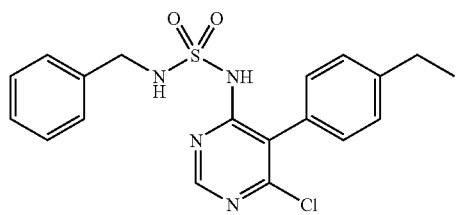
LC-MS:t$_R$:5.10; [M + H]$^+$:403.05
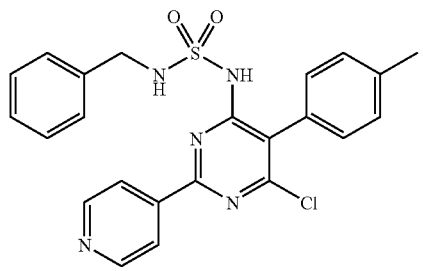
LC-MS:t$_R$:4.84; [M + H]$^+$:466.11
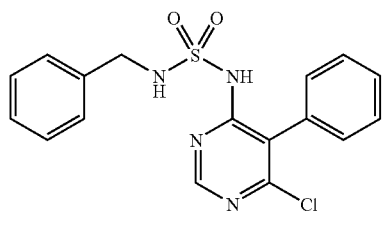
LC-MS:t$_R$:4.65; [M + H]$^+$:375.05
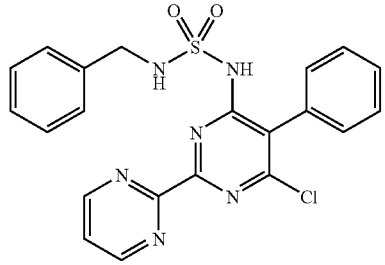
LC-MS:t$_R$:4.45; [M + H]$^+$:453.03
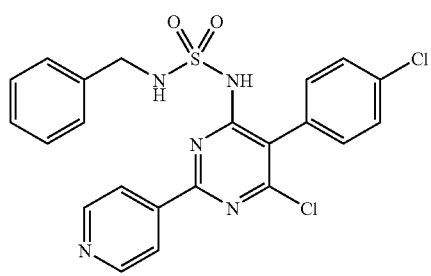
LC-MS:t$_R$:5.06; [M + H]$^+$:486.01
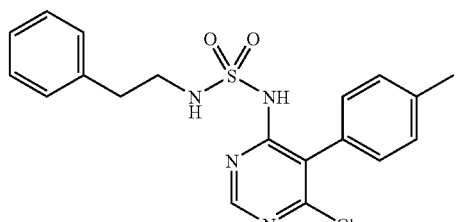
LC-MS:t$_R$:5.08; [M + H]$^+$:403.03
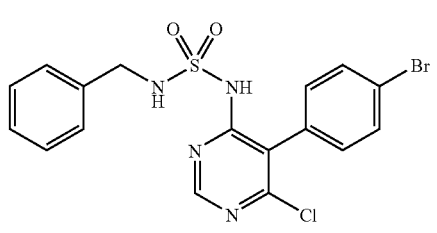
LC-MS:t$_R$:5.05; [M + H]$^+$:454.99
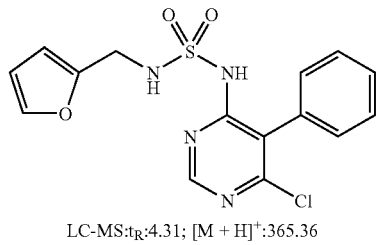
LC-MS:t$_R$:4.31; [M + H]$^+$:365.36
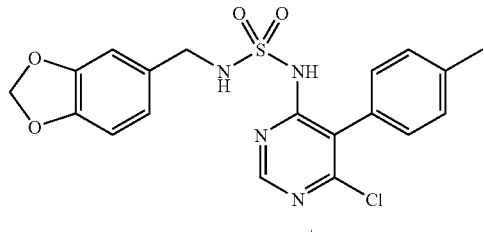
LC-MS:t$_R$:5.05; [M + H]$^+$:454.99
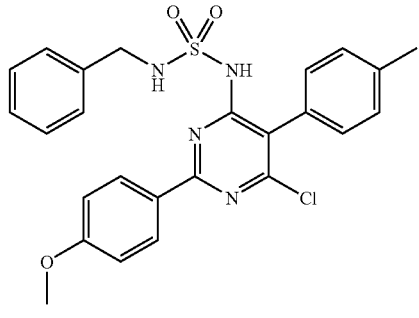
LC-MS:t$_R$:6.02; [M + H]$^+$:495.30

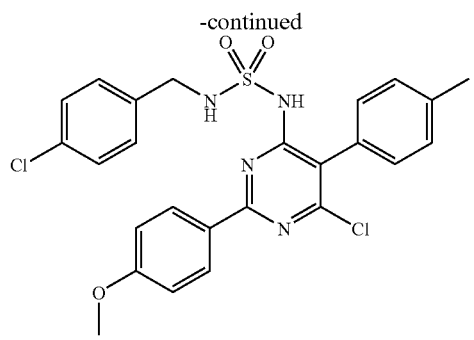
LC-MS:t$_R$:6.11; [M + H]$^+$:529.28
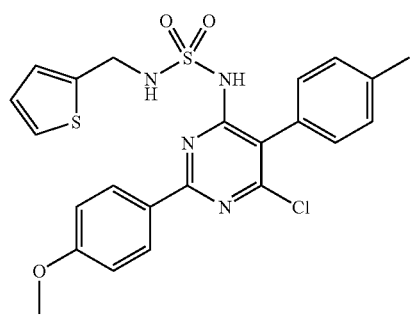
LC-MS:t$_R$:5.86; [M + H]$^+$:501.08
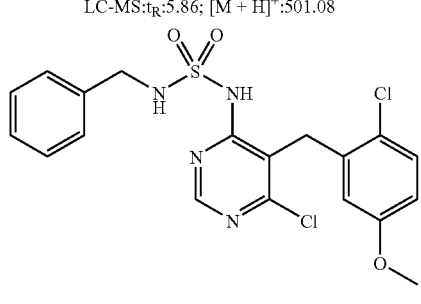
LC-MS:t$_R$:5.13; [M + H]$^+$:456.91
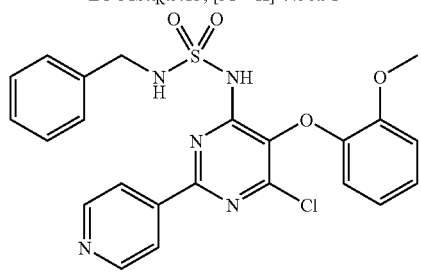
LC-MS:t$_R$:4.68; [M + H]$^+$:498.14
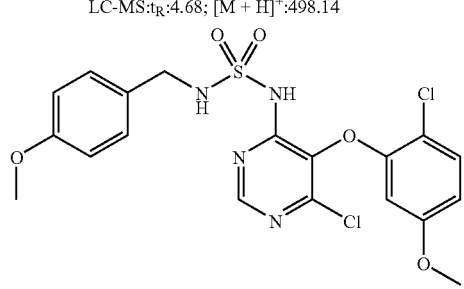
LC-MS:t$_R$:4.93; [M + H]$^+$:484.95
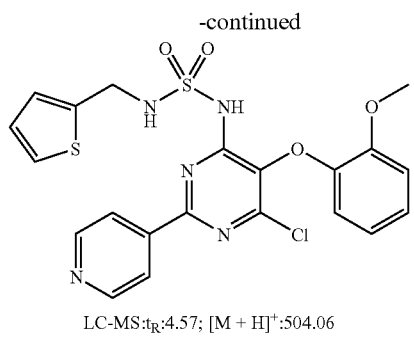
LC-MS:t$_R$:4.57; [M + H]$^+$:504.06
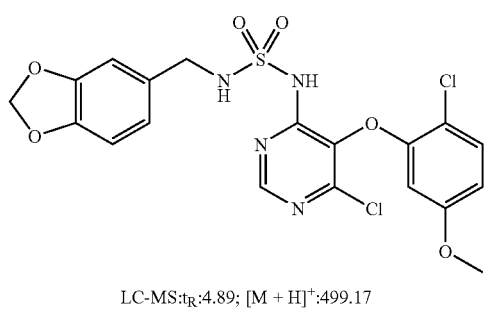
LC-MS:t$_R$:4.89; [M + H]$^+$:499.17
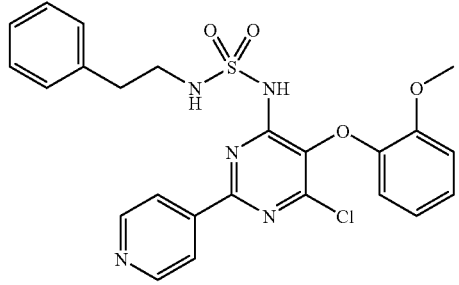
LC-MS:t$_R$:4.90; [M + H]$^+$:512.18
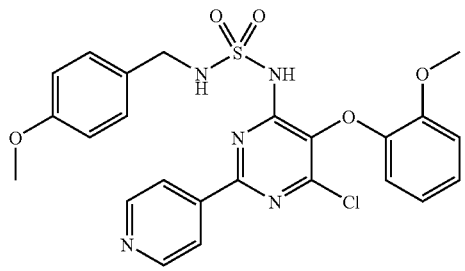
LC-MS:t$_R$:4.72; [M + H]$^+$:527.94
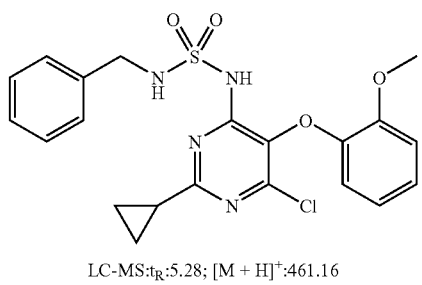
LC-MS:t$_R$:5.28; [M + H]$^+$:461.16

-continued
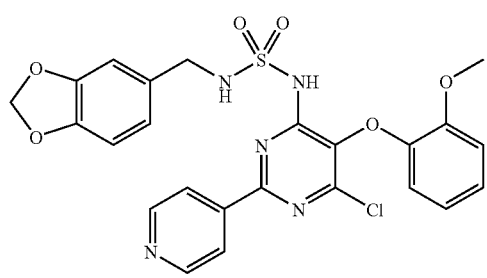
LC-MS:t$_R$:4.63; [M + H]$^+$:542.08
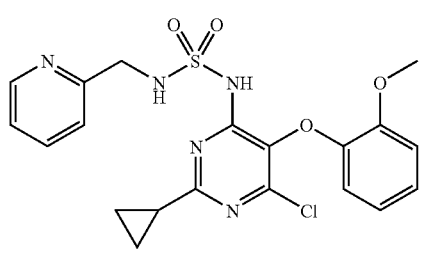
LC-MS:t$_R$:3.91; [M + H]$^+$:462.17
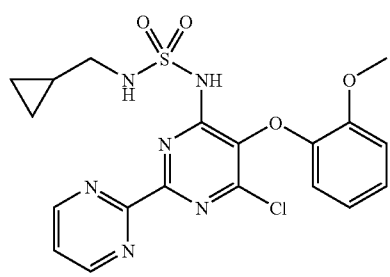
LC-MS:t$_R$:4.43; [M + H]$^+$:463.09
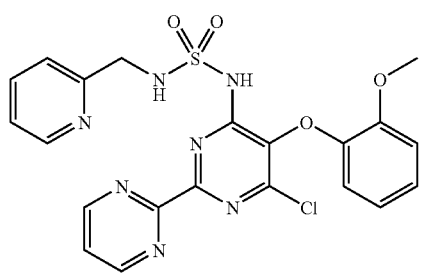
LC-MS:t$_R$:3.20; [M + H]$^+$:497.93
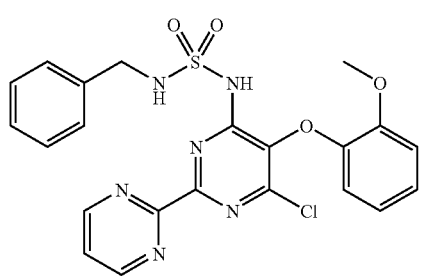
LC-MS:t$_R$:4.47; [M + H]$^+$:499.11
-continued
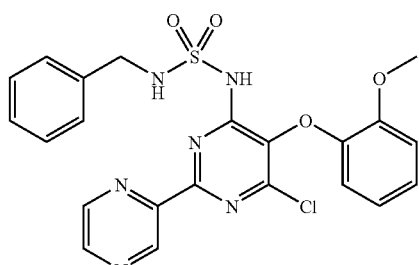
LC-MS:t$_R$:4.90; [M + H]$^+$:499.06
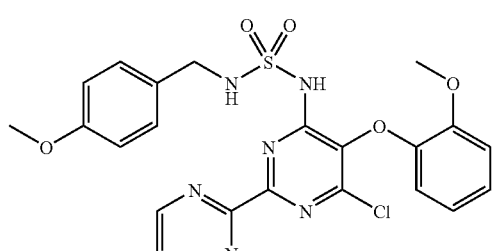
LC-MS:t$_R$:4.44; [M + H]$^+$:529.22
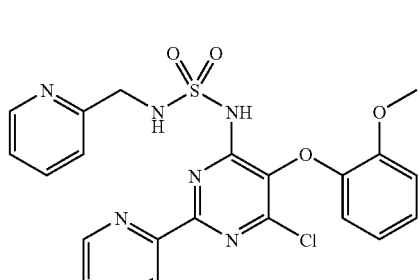
LC-MS:t$_R$:3.94; [M + H]$^+$:500.06
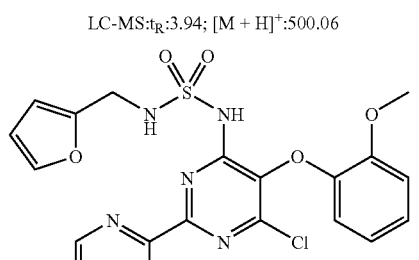
LC-MS:t$_R$:4.33; [M + H]$^+$:489.51
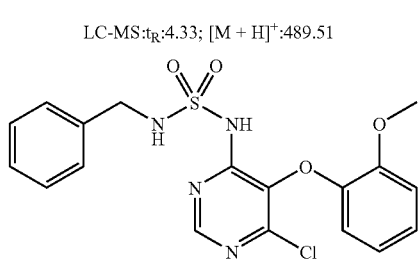
LC-MS:t$_R$:4.68; [M + H]$^+$:421.09

-continued
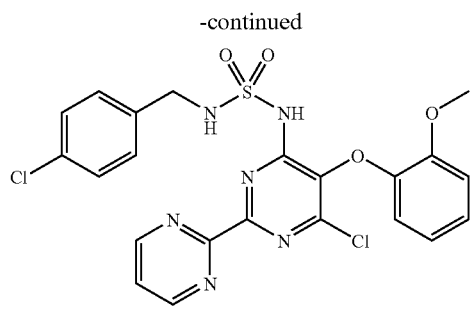
LC-MS:t$_R$:4.74; [M + H]$^+$:535.06
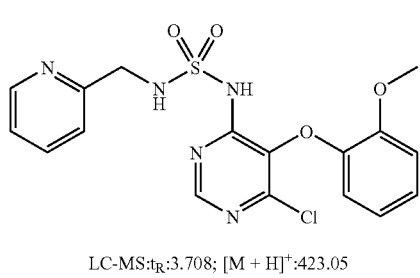
LC-MS:t$_R$:3.708; [M + H]$^+$:423.05
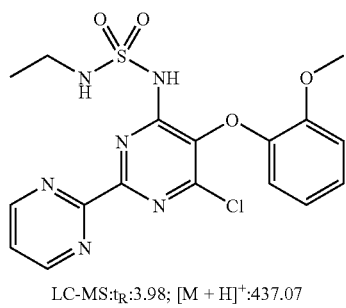
LC-MS:t$_R$:3.98; [M + H]$^+$:437.07
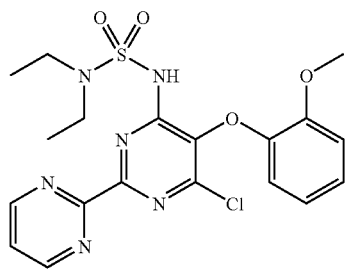
LC-MS:t$_R$:4.53; [M + H]$^+$:465.22
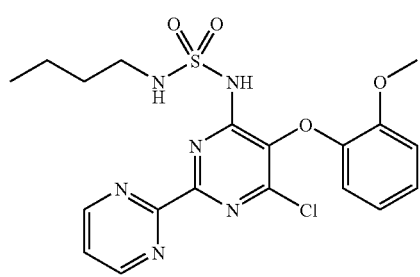
LC-MS:t$_R$:5.51; [M + H]$^+$:465.15
-continued
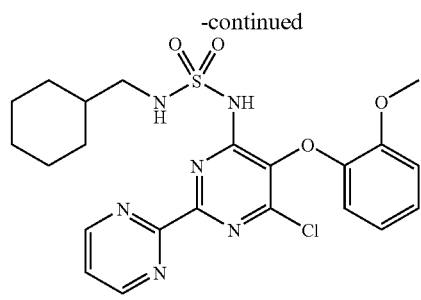
LC-MS:t$_R$:5.14; [M + H]$^+$:505.20
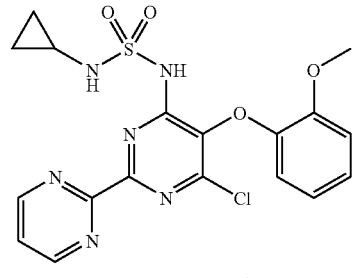
LC-MS:t$_R$:4.23; [M + H]$^+$:449.17
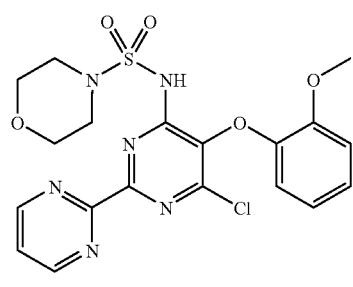
LC-MS:t$_R$:4.08; [M + H]$^+$:479.22
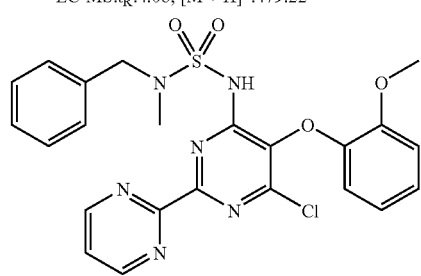
LC-MS:t$_R$:5.07; [M + H]$^+$:513.19
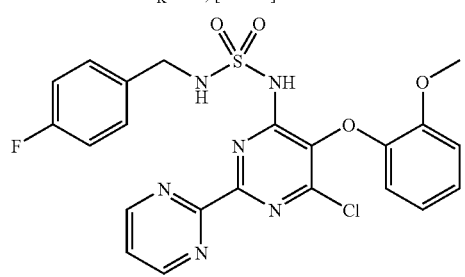
LC-MS:t$_R$:4.67; [M + H]$^+$:517.26

-continued
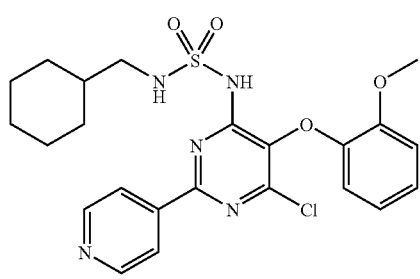
LC-MS:t$_R$:5.36; [M + H]$^+$:505.63
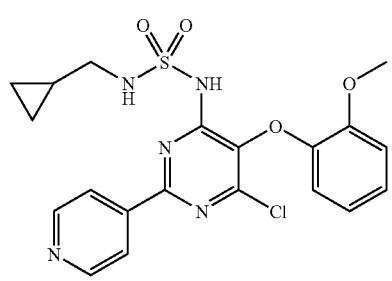
LC-MS:t$_R$:4.69; [M + H]$^+$:462.23
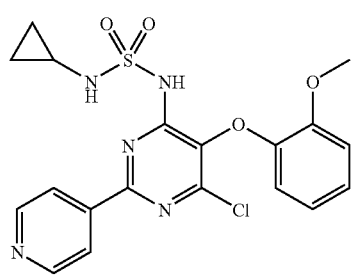
LC-MS:t$_R$:4.38; [M + H]$^+$:448.27
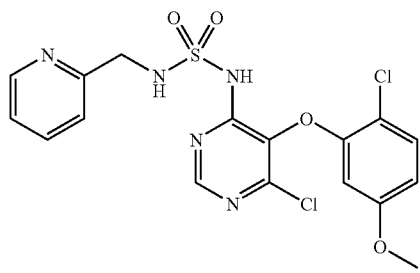
LC-MS:t$_R$:4.09; [M + H]$^+$:456.21
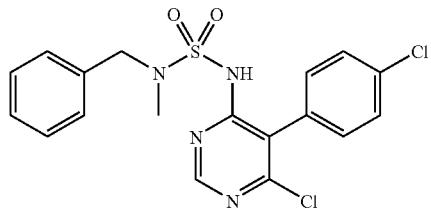
LC-MS:t$_R$:5.48; [M + H]$^+$:424.80
-continued
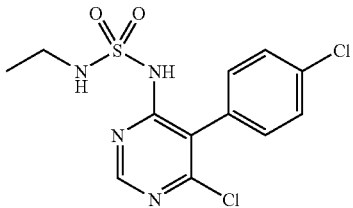
LC-MS:t$_R$:4.42; [M + H]$^+$:347.03
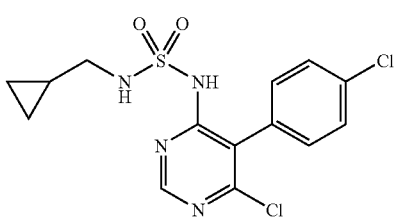
LC-MS:t$_R$:4.85; [M + H]$^+$:375.03
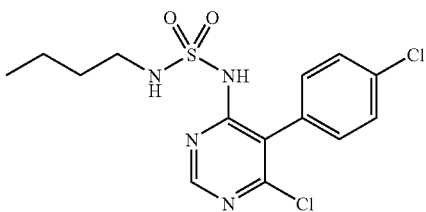
LC-MS:t$_R$:4.94; [M + H]$^+$:376.65
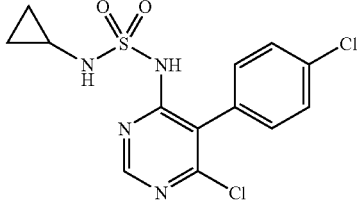
LC-MS:t$_R$:4.61; [M + H]$^+$:360.99
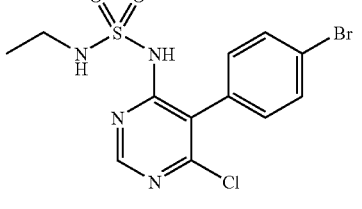
LC-MS:t$_R$:4.41; [M + H]$^+$:392.95
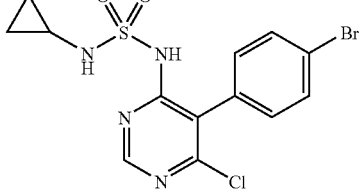
LC-MS:t$_R$:4.94; [M + H]$^+$:404.97

Synthesis of the sulfamic acid amides:

Sulfamoylchloride ($NH_2$—$SO_2$—Cl) was prepared according to the procedure given in the literature [11] and [12].

Referential Example 17

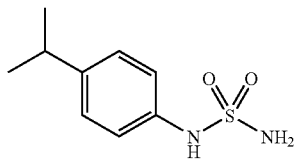

To a solution of sulfamoylchloride in benzene (0.09 mol in 70 ml) was added 4-i-propyl aniline (25.6 ml) via addition funnel at 0° C. The suspension was diluted with benzene (80 ml) and stirred for 20 min. $NaOH_{aq}$ (36 ml; 5 N) was added and the suspension was thoroughly shaken. EtOAc (500 ml) was added and under ice cooling conc. hydrochloric acid was added until pH=6. The water was separated and the EtOAc was evaporated. The brown residue was shaken twice with hexane followed by the addition of a sodium hydroxide solution (5 N). The mixture is was extracted three times with diethylether. The water layer was cooled to 0° C. and the pH adjusted to 2 by the addition of conc. hydrochloric acid. The product precipitated and was filtered off and washed with cold water. After high vacuum drying 4-isopropyl-phenyl-sulfamic acid amide was obtained (3.47 g).

Referential Example 18

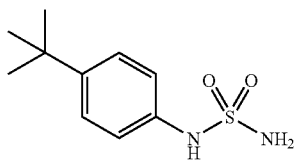

According to the procedure described in Referential Example 17, 4-tert.-butyl-phenyl-sulfamic acid amide was prepared.

Referential Example 19

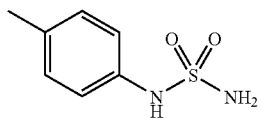

According to the procedure described in Referential Example 17, 4-methyl-phenyl-sulfamic acid amide was prepared.

Referential Example 20

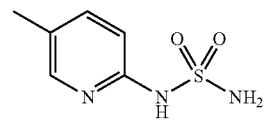

To a solution of 2-amino-5-methyl-pyridine (3.24 g) in THF (30 ml) was added sodium hydride (1.2 g; 60% disperison in mineral oil). The mixture was warmed to 45° C. for 30 min. After cooling to 10° C. a solution of sulfamoylchloride in diethylether (0.0445 mol in 62.5 ml) was added within 30 min followed by stirring for 30 min at r.t. and evaporation of the solvent. To the residue was added a sodium hydroxide solution (5 N, 15 ml). The mixture was extracted several times with toluene. The water layer was cooled to 0° C. and the pH was adjusted to 7 by the addition of conc. hydrochloric acid. The product crystallized and was filtered off to give 5-methyl-pyridine-2-sufamic acid amide (1.1 g).

Referential Example 21

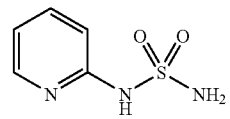

According to the procedure described in Referential Example 20, pyridine-2-sulfamic acid amide was prepared.

Further cycloalkyl-, aryl- or heteroaryl-sulfamic acid amides (as given by the formulae in FIG. 1) can be prepared according to the procedure described in Referential Example 17 (for cycloalkyl and aryl derivatives) or according to the procedure described in Referential Example 21 (for heteroaryl derivatives) or according to the procedure described in Referential Example 22 (for cycloalkyl derivatives).

Figure 1:

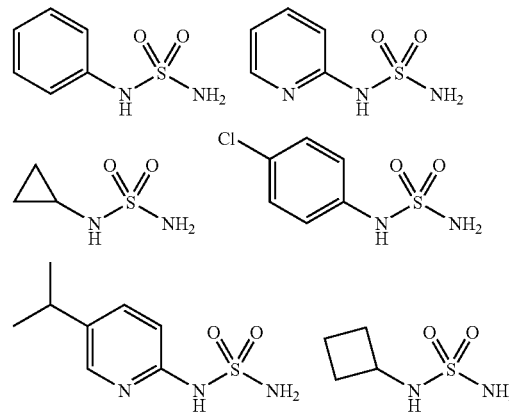

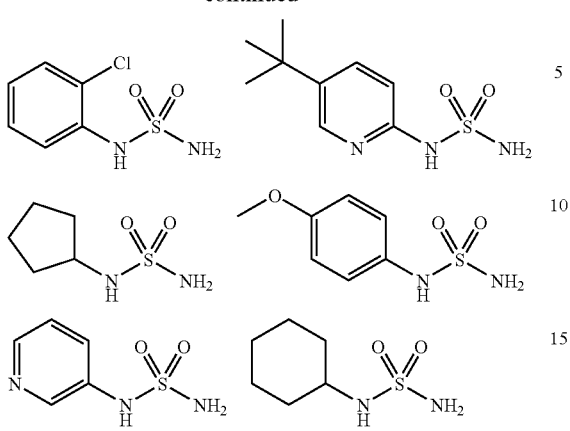

Referential Example 22: [19]

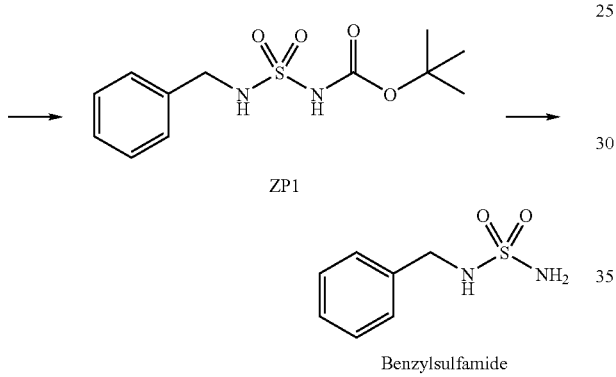

a) Chlorosulfonylisocyanate (14.14 g) was dissolved in DCM (50 ml) and cooled to 0° C. A solution of tert.-butanol (9.6 ml) in DCM (50 ml) was added within 30 minutes. Stirring was continued for additional 30 minutes at rt.

b) The solution prepared as described under a) was then added at 0° C. within 1 h to a solution of benzylamine (10.7 g) and triethylamine (15.32 ml) in DCM (200 ml). Stirring was continued for 10 h at rt. The mixture was concentrated in vacuo, taken into EtOAc (500 ml) and washed with water (2 times 40 ml) and brine (30 ml), dried with magnesium sulfate and again concentrated in vacuo. The crude material was crystallized from EtOAc and dried at HV to give ZP1 (13.68 g). ZP1 was dissolved in dioxane (20 ml) and 120 ml 4 M HCl in dioxane was added within 1 h at rt. Stirring was continued for 8 h followed by complete evaporation of the solvents and drying at HV to give benzylsulfamide (9.47 g).

Further —HN—CH$_2$-aryl/—HN—CH$_2$-heteroaryl/—HN—CH$_2$-alkyl/—HN—CH$_2$-cycloalkyl/—HN—CH$_2$-heterocyclyl and other sulfamic acid amides (as given by the formulae in FIG. 2) can be prepared according to the procedure described in Referential Example 22.

Figure 2:

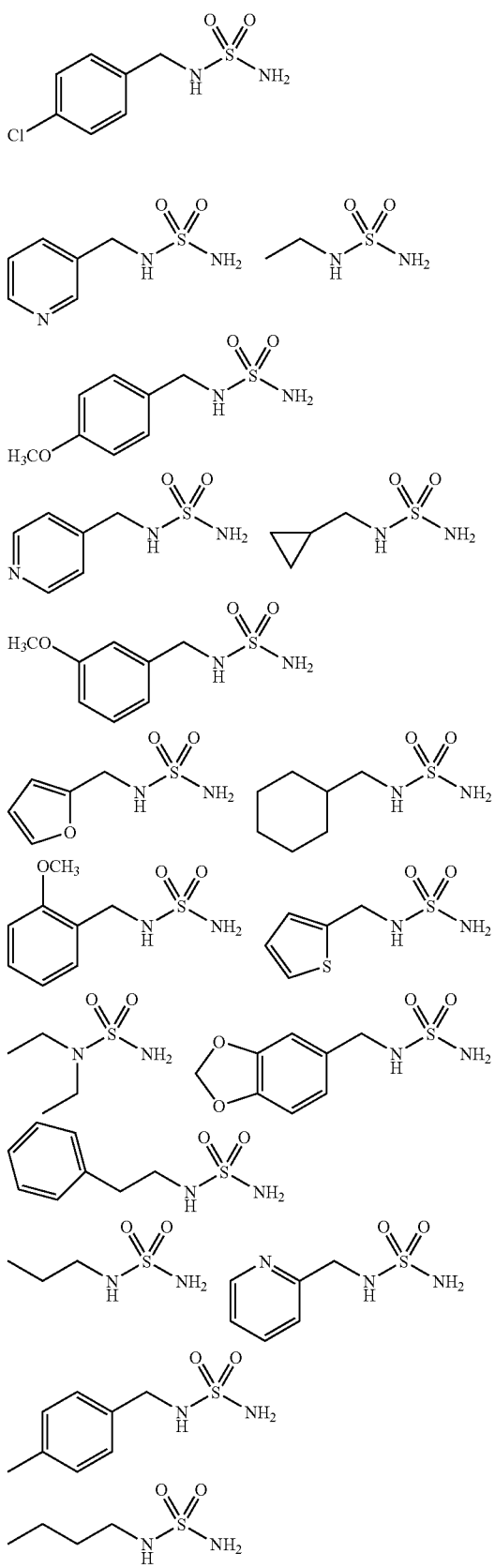

-continued

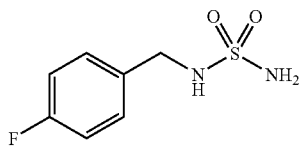

Example 1

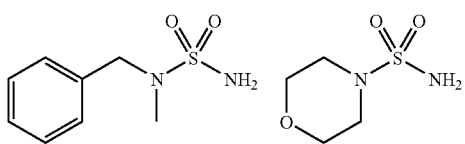

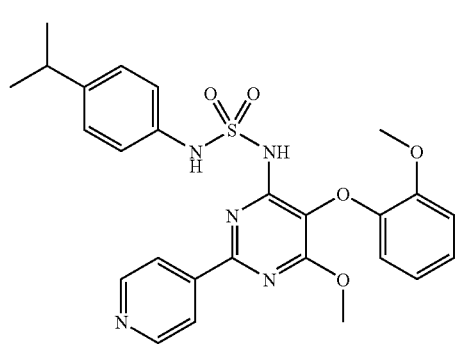

To a mixture of methanol (1 ml) and THF (2 ml) was added sodium hydride (100 mg, 60% dispersion in mineral oil) followed by the addition of 4-i-propyl-phenyl sulfamic acid-[6-chloro-5-(o-methoxyphenoxy)-2-(4-pyridyl)-pyrimidin-4-yl]-amide (100 mg, Referential Example 1e)). DMF (0.5 ml) was added and the reaction mixture was heated to 80° C. for 20 h. The solvents were evaporated, water (14 ml) and a 10% solution of citric acid was added until the pH was 3. The precipitate was filtered off and washed with water to give 4-i-propyl-phenyl sulfamic acid-[6-methoxy-5-(o-methoxyphenoxy)-2-(4-pyridyl)-pyrimidin-4-yl]-amide (100 mg). $t_R$=5.08 min, (LC); [M+H]$^+$=522.45 (ES+).

Example 2

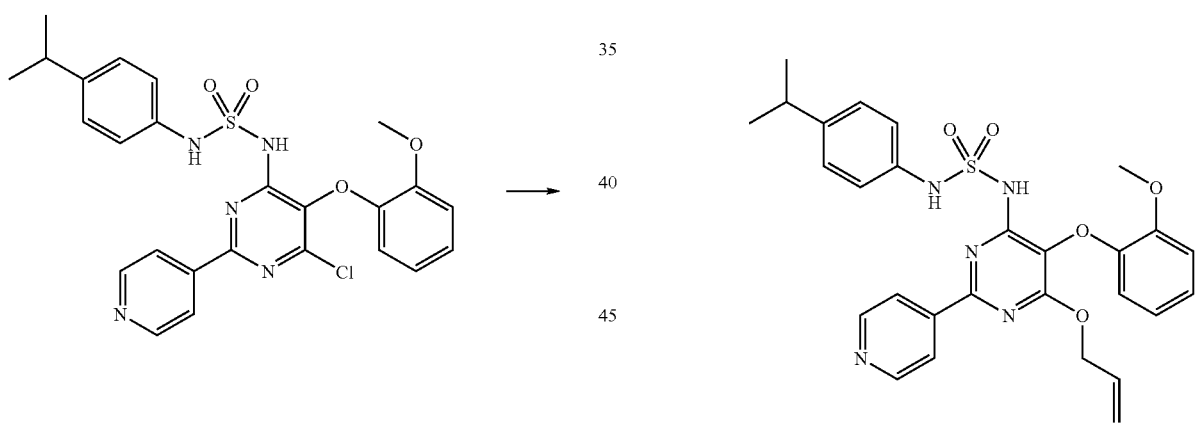

To a mixture of allyl alcohol (1 ml) and THF (2 ml) was added sodium hydride (100 mg, 60% dispersion in mineral oil) followed by the addition of 4-i-propyl-phenyl sulfamic acid-[6-chloro-5-(o-methoxyphenoxy)-2-(4-pyridyl)pyrimidin-4-yl]-amide (100 mg, Referential Example 1e)). DMF (0.5 ml) was added and the reaction mixture was heated to 80° C. for 20 h. The solvents were evaporated, water (14 ml) and a 10% solution of citric acid was added until the pH was 3. The precipitate was filtered off and washed with water and purified by chromatography through silicagel with EtOAc/Hex=3:2 to give 4-i-propyl-phenyl sulfamic acid-[6-allyloxy-5-(o-methoxyphenoxy)-2-(4-pyridyl)pyrimidin-4-yl]-amide (10 mg). $t_R$=5.36 min, (LC); [M+H]$^+$=548.46 (ES+).

Example 3

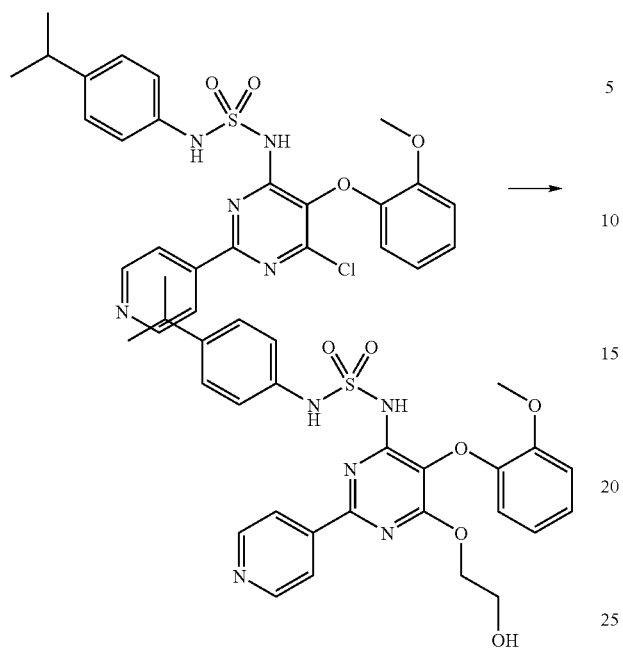

Sodium hydride (17 mg, 60% dispersion in mineral oil) was added to ethylene glycol (1.2 ml) followed by addition of dimethoxyethane (0.5 ml). Stirring was continued for 30 min, then 4-i-propyl-phenyl sulfamic acid-[6-chloro-5-(o-methoxyphenoxy)-2-(4-pyridyl)-pyrimidin-4-yl]-amide (45 mg, Referential Example 1e)) was added and the reaction mixture was heated to 80° C. for 48 h. The solvents were evaporated, water (10 ml) and a 10% solution of citric acid was added until the pH was 3 followed by extraction with EtOAc. The organic layers were dried over sodium sulfate and the solvent was evaporated. The crude product was purified by chromatography through silicagel with EtOAc to give 4-i-propyl-phenyl sulfamic acid-[6-(2-hydroxy-ethoxy)-5-(o-methoxyphenoxy)-2-(4-pyridyl)-pyrimidin-4-yl]-amide (38 mg). $t_R$=4.56 min, (LC); [M+H]$^+$=552.36 (ES+).

Example 4

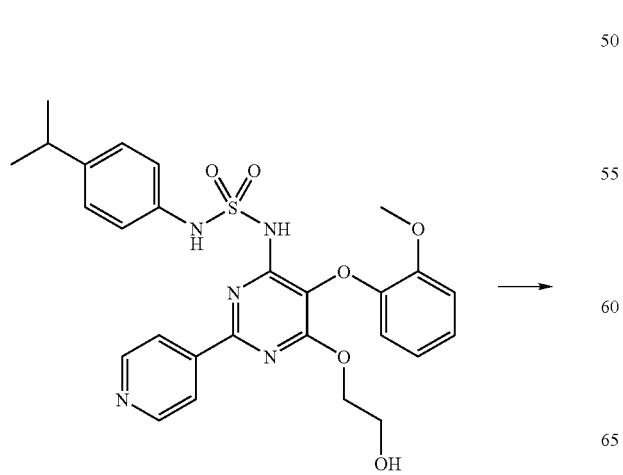

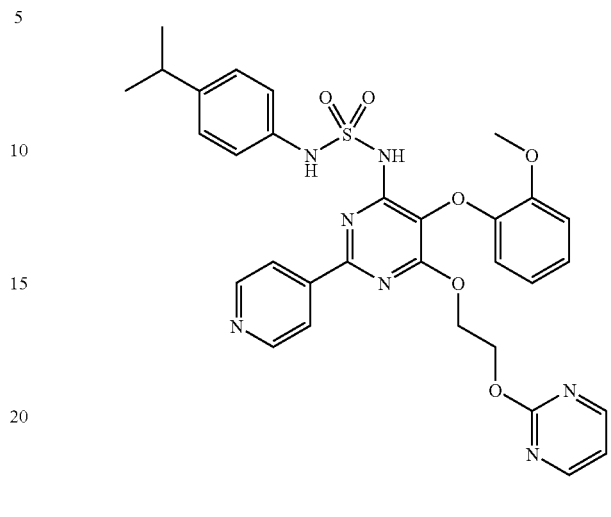

4-i-Propyl-phenyl sulfamic acid-[6-(2-hydroxy-ethoxy)-5-(o-methoxyphenoxy)-2-(4-pyridyl)-pyrimidin-4-yl]-amide (60 mg, Example 3) was dissolved in THF (8 ml) and sodium hydride (14 mg, 60% dispersion in mineral oil) was added and stirring continued for 10 min. 2-Chloro-pyrimidine (22 mg) was added and the mixture was heated to 60° C. for 90 min. DMF (0.5 ml) was added and the solution was stirred at r.t. for 48 h. The solvents were evaporated, water (12 ml) and a 10% solution of citric acid was added until the pH was 3. The precipitate was filtered off and washed with water and purified by recrystallization from diethyl ether to give 4-i-propyl-phenyl sulfamic acid-[6-[2-(pyrimidin-2-yloxy)-ethoxy]-5-(o-methoxyphenoxy)-2-(4-pyridyl)pyrimidin-4-yl]-amide (50 mg). $t_R$=4.80 min, (LC); [M+H]$^+$=630.91 (ES+).

Example 5

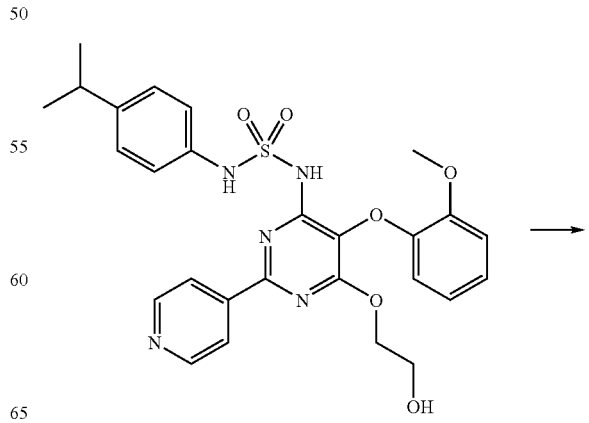

-continued

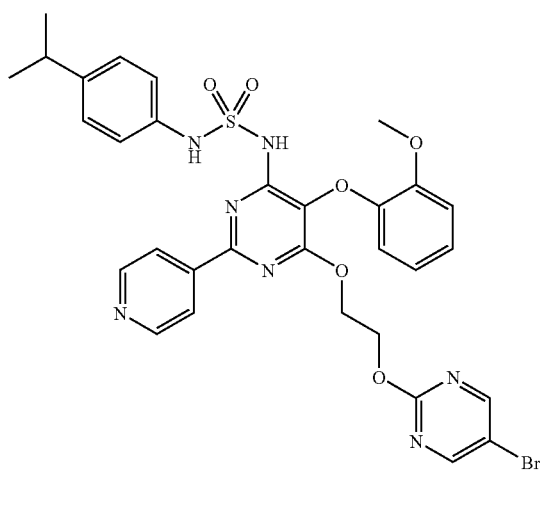

4-i-Propyl-phenyl sulfamic acid-[6-(2-hydroxy-ethoxy)-5-(o-methoxyphenoxy)-2-(4-pyridyl)-pyrimidin-4-yl]-amide (60 mg, Example 3) was dissoved in THF (8 ml). Sodium hydride (14 mg, 60% dispersion in mineral oil) was added and stirring continued for 10 min. 5-Bromo-2-chloro-pyrimidine (37 mg) was added and the mixture was heated to 60° C. for 120 min. DMF (0.5 ml) was added and the solution was stirred at r.t. for 48 h. The solvents were evaporated, water (12 ml) and a 10% solution of citric acid was added until the pH was 3. The precipitate was filtered off and washed with water and purified by chromatography through silica gel with EtOAc/Hex=1:1 to give 4-i-propyl-phenyl sulfamic acid-[6-[2-(5-bromo-pyrimidin-2-yloxy)-ethoxy]-5-(o-methoxy-phenoxy)-2-(4-pyridyl)pyrimidin-4-yl]-amide (55.4 mg). $t_R$=5.30 min, (LC); [M+H]$^+$=710.35 (ES+).

Example 6

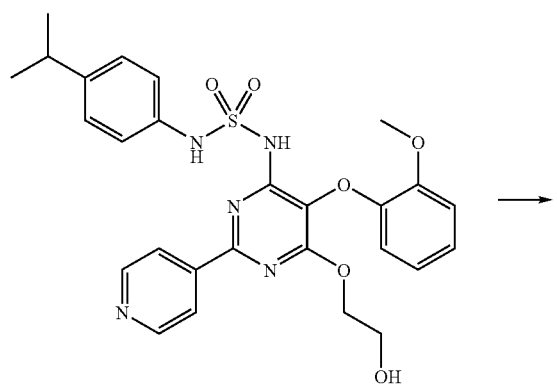

→

-continued

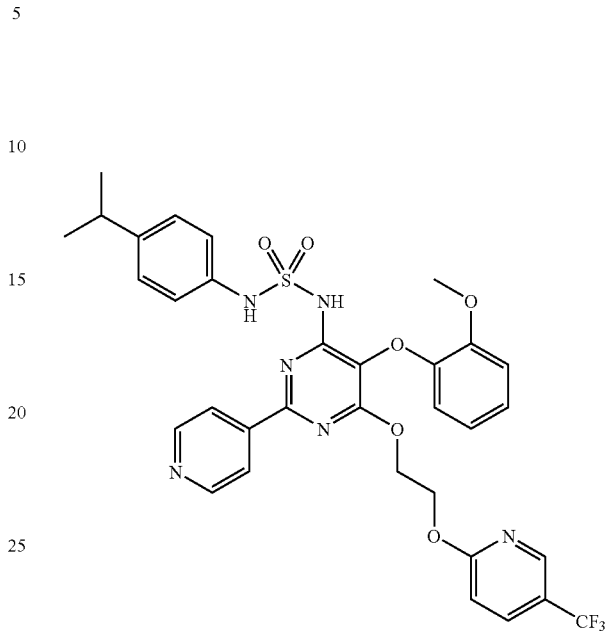

4-i-Propyl-phenyl sulfamic acid-[6-(2-hydroxy-ethoxy)-5-(o-methoxyphenoxy)-2-(4-pyridyl)-pyrimidin-4-yl]-amide (50 mg, Example 3) was dissolved in THF (8 ml). Sodium hydride (12 mg, 60% dispersion in mineral oil) was added and stirring continued for 10 min. 5-Trifluoromethyl-2-chloro-pyridine (28 mg) was added and the mixture was heated to 60° C. for 180 min. The solvents were evaporated, water (12 ml) and a 10% solution of citric acid was added until the pH was 3. The precipitate was filtered off, washed with water and purified by recrystallization with diethylether to give 4-i-propyl-phenyl sulfamic acid-[6-[2-(5-trifluorom-ethyl-pyridin-2-yloxy)-ethoxy]-5-(o-methoxy-phenoxy)-2-(4-pyridyl)-pyrimidin-4-yl]-amide (41 mg). $t_R$=5.81 min, (LC); [M+H]$^+$=697.17 (ES+).

Example 7

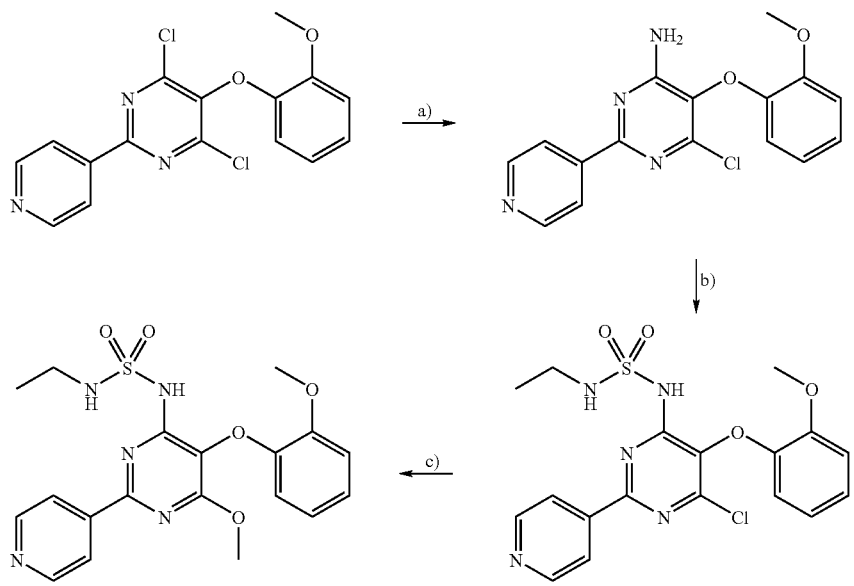

a) 4,6-Dichloro-5-(o-methoxyphenoxy)-2-(4-pyridyl)-pyrimidine (2.9 g, Referential Example 1d)) was suspended in dioxane (30 ml) and ammonia (gaseous) was introduced until the solution was saturated. Stirring was continued for 7 days while the saturation of the reaction mixture with ammonia (gaseous) was repeated every 16 to 20 h. The solvent was evaporated, water was added to the residue and the precipitate was filtered off. After drying at HV/50° C. 4-amino-6-chloro-5-(o-methoxyphenoxy)-2-(4-pyridyl)-pyrimidine (2.7 g) was obtained.

b) 4-Amino-6-chloro-5-(o-methoxyphenoxy)-2-(4-pyridyl)-pyrimidine (100 mg) was dissolved in THF (5 ml) and DCM (5 ml). DBU (46 mg) and DMAP (37 mg) were added followed by the addition of ethyl-sulfamoylchloride (prepared from ethylamine hydrochloride and sulfuryl chloride). The mixture was stirred for 12 h at r.t. The solvent was evaporated. Water and a 10% solution of citric acid were added followed by extraction with EtOAc and DCM. The combined organic layers were dried over sodium sulfate and the solvent was evaporated under reduced pressure. After purification of the residue by chromatography over silicagel with EtOAc/methanol/ammonia=4:1:0.5, ethyl sulfamic acid-[6-chloro-5-(o-methoxy-phenoxy)-2-(4-pyridyl)pyrimidin-4-yl]-amide (10 mg) was obtained. $t_R$=4.31 min, (LC); [M+H]$^+$=436.14 (ES+).

c) Ethyl sulfamic acid-[6-chloro-5-(o-methoxy-phenoxy)-2-(4-pyridyl)-pyrimidin-4-yl]-amide (14 mg) was suspended in methanol (1 ml) followed by addition of a solution of potassium tert.-butylate (8.5 mg) in methanol (1 ml). The mixture was heated to 85° C. for 18 h. The solvent was evaporated and water and a 10% solution of citric acid was added. The precipitate was filtered off and washed with water. After drying at HV ethyl sulfamic acid-[6-methoxy-5-(o-methoxy-phenoxy)-2-(4-pyridyl)-pyrimidin-4-yl]-amide (10 mg) were obtained. $t_R$=4.25 min, (LC); [M+H]$^+$=432.32 (ES+).

Example 8

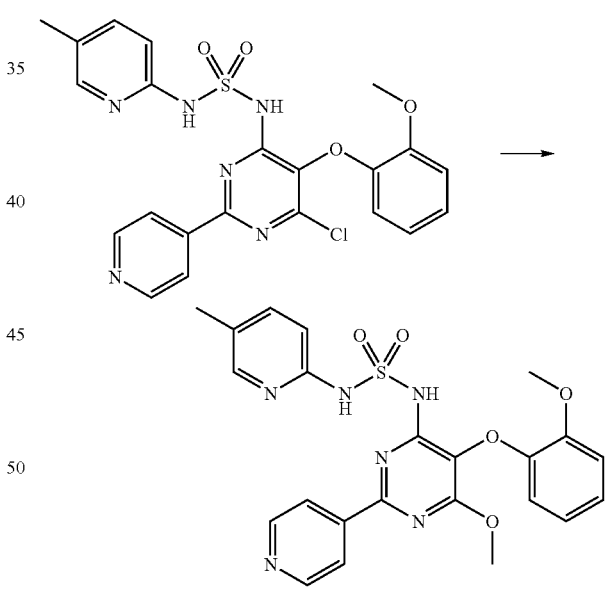

Sodium hydride (100 mg, 60% dispersion in mineral oil) was dissloved in methanol (1.2 ml). 5-methyl-pyridine-2-sulfamic acid-[6-chloro-5-(o-methoxy-phenoxy)-2-(4-pyridyl)-4-pyrimidinyl]-amide (50 mg, Referential Example 11), DMF (0.5 ml) and THF (1 ml) was added and the solution was stirred for 30 h at 80° C. The solvents were evaporated and the residue was washed with hexane (3×) and the hexane was decanted. A solution of 10% citric acid was added and the precipitate was filtered off and washed with water. After drying at HV 5-methyl-pyridine-2-sulfamic acid-[6-methoxy-5-(o-methoxy-phenoxy)-2-(4-pyridyl)-4-pyrimidinyl]-amide (37 mg) was obtained. $t_R$=3.73 min, (LC); [M+H]$^+$=495.38 (ES+).

Example 9

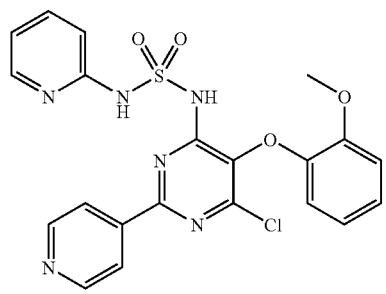

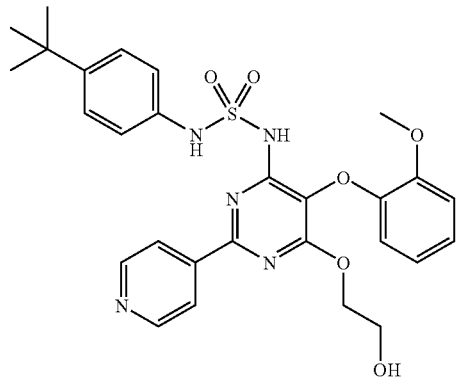

Pyridine-2-sulfamic acid-[6-chloro-5-(o-methoxyphenoxy)-2-(4-pyridyl)-4-pyrimidinyl]-amide (15 mg, Referential Example 12) was suspended in THF (1 ml) and DMF (0.2 ml) and sodium methylate (40 mg) was added. The mixture was stirred for 90 h at 80° C. followed by evaporation of the solvents. A solution of 10% citiric acid was added to the residue. The precipitate was filtered off and washed with water. After drying at HV pyridine-2-sulfamic acid-[6-methoxy-5-(o-methoxyphenoxy)-2-(4-pyridyl)-4-pyrimidinyl]-amide (7 mg) was obtained. $t_R$=3.55 min, (LC); $[M-H]^+$=479.41 (ES−).

Example 10

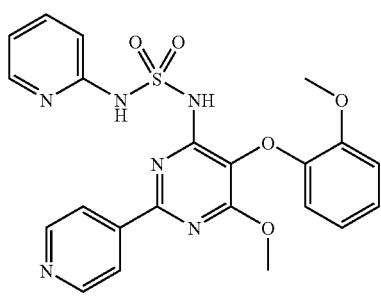

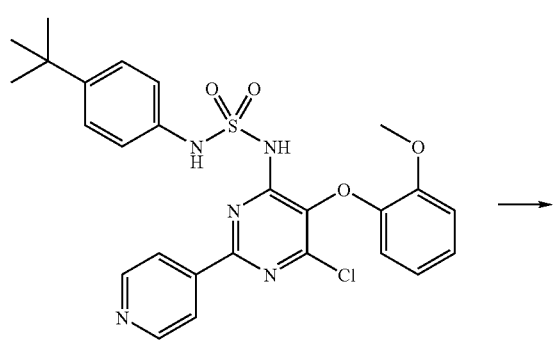

Sodium hydride (28 mg, 60% dispersion in mineral oil) was dissolved in ethyleneglycol (1.2 ml) and 1,2-dimethoxyethane (1 ml). 4-t-butyl-phenyl sulfamic acid-[6-chloro-5-(o-methoxyphenoxy)-2-(4-pyridyl)-4-pyrimidinyl]-amide (75 mg, Referential Example 10) was added and stirring continued for 90 h at 80° C. The mixture was evaporated and a 10% solution of citric acid was added. The precipitate was filtered off and washed with water. After purification by chromatography over silica gel with EtOAc 4-t-butyl-phenyl sulfamic acid-[6-(2-hydroxy-ethoxy-5-(o-methoxy-phenoxy)-2-(4-pyridyl)-4-pyrimidinyl]-amide (40 mg) could be isolated. $t_R$=4.81 min, (LC); $[M+H]^+$=566.35 (ES−).

Example 11

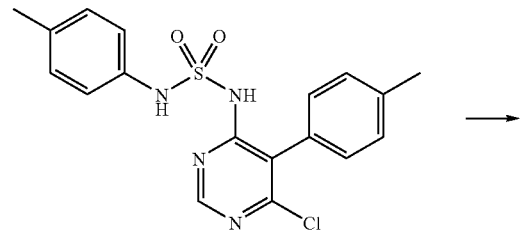

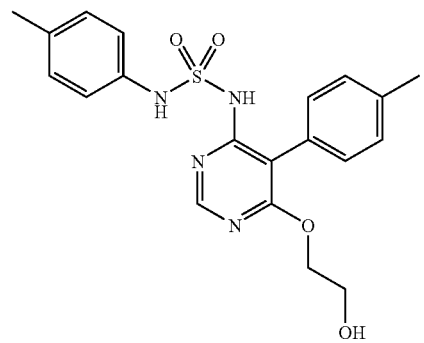

To a mixture of 1,2-dimethoxyethan (15 ml) and ethyleneglycol (40 ml) was added sodium (298 mg) in small portions. The mixture was stirred until the sodium was completely dissolved. Then DMF (15 ml), followed by 4-methyl-phenyl sulfamic acid-[6-chloro-5-(p-tolyl)-4-pyrimidinyl]-amide (1.0 g, Referential Example 14) was added. Stirring was continued for 4 days at 100° C. The mixture was evaporated and water (150 ml) was added to the residue followed by addition of acetic acid (1.0 ml). The precipitate was filtered off, washed with water and dried. The crude material was purified by chromatography over silicagel with EtOAc/methanol/aquous ammonia (25%)=4/1/0.5 to give 4-methyl-phenyl sulfamic acid-[6-(2-hydroxy-ethoxy)-5-(p-tolyl)-4-pyrimidinyl]-amide (500 mg). $t_R$=4.38 (LC); $[M+H]^+$=415.19 (ES+).

Example 12

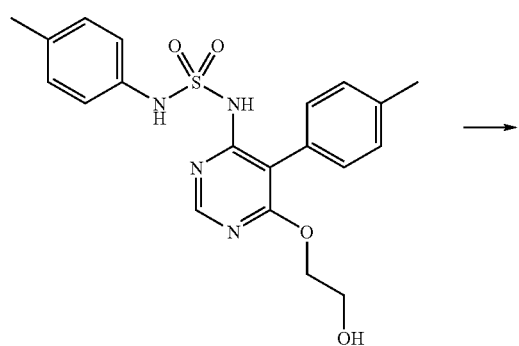

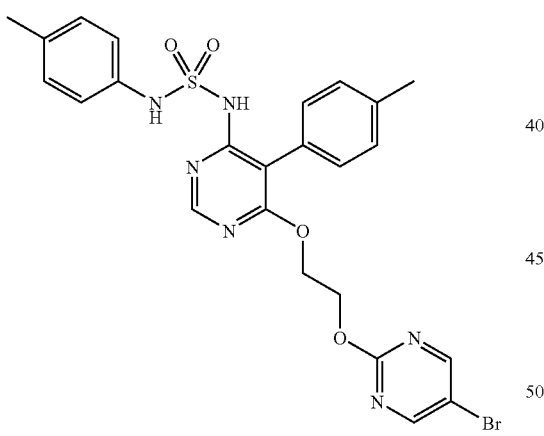

To 4-methyl-phenyl sulfamic acid-[6-(2-hydroxy-ethoxy)-5-(p-tolyl)-4-pyrimidinyl]-amide (47 mg, Example 11) dissolved in THF (8 ml) was added sodium hydride (14.6 mg, 60% dispersion in mineral oil) and stirring was continued for 15 min followed by the addition of 5-bromo-2-chloro-pyrimidine (39 mg). Stirring was continued for 2 h at 50° C. and 80 h at r.t. The mixture was evaoprated and a 10% citric acid solution was added. The precipitate was filtered off, washed with water and purified by chromatography over silicagel with EtOAc/Hex=1/1 to give 4-methyl-phenyl sulfamic acid-[6-[2-(5-bromo-pyrimidin-2-yloxy)-ethoxy]-5-(p-tolyl)-4-pyrimidinyl]-amide (34 mg). $t_R$=5.34 (LC); $[M+H]^+$=573.02 (ES+).

Example 13

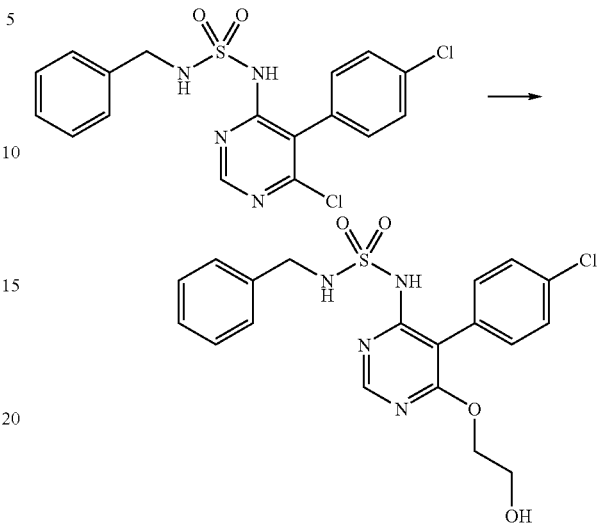

Potassium tert.-butoxide (3.5 g) was dissolved in ethyleneglycol (35 ml), benzyl sulfamic acid-[6-chloro-5-(4-chlorophenyl)-4-pyrimidinyl]-amide (1.8 g, Referential Example 15) was added and the mixture was heated to 102° C. for 11 h. The mixture was poured onto ice/water and acidified to pH=4 with solid citric acid. The precipitated product was filtered off, washed with water and dried at HV to give benzyl sulfamic acid-[6-(2-hydroxy-ethoxy)-5-(4-chlorophenyl)-4-pyrimidinyl]-amide (1.77 g). $t_R$=4.36 (LC); $[M+H]^+$=435.09 (ES+).

Example 14

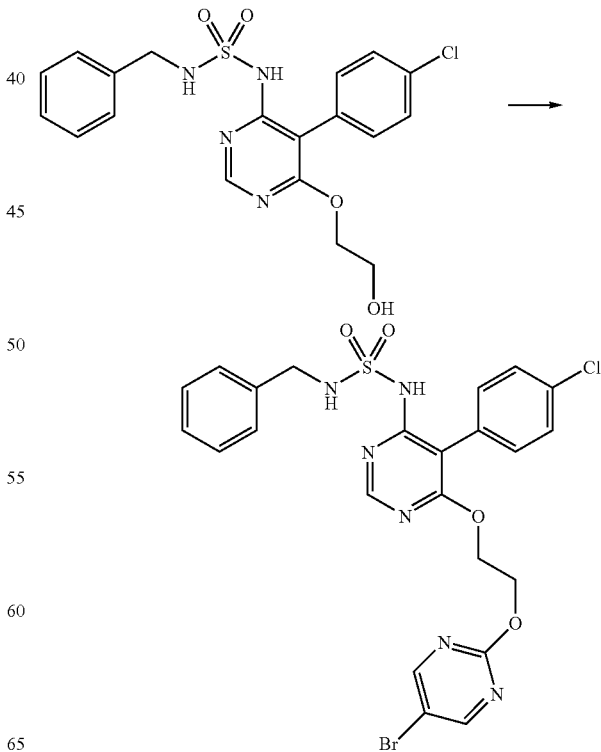

Benzyl sulfamic acid-[6-(2-hydroxy-ethoxy)-5-(4-chlorophenyl)-4-pyrimidinyl]-amide (375 mg, Example 13) was dissolved in THF (30 ml) followed by addition of sodium hydride (60% dispersion in mineral oil) (140 mg).

The mixture was stirred for 30 min followed by the addition of 5-bromo-2-chloro-pyrimidine (320 mg). Stirring was continued at 60° C. for 8 h. The reaction mixture was poured onto ice/water and acidified with solid citric acid. The precipitate was filtered off and purified by chromatography over silicagel with hexane/EtOAc=2/1 to give benzyl sulfamic acid-[6-[2-(5-bromo-pyrimidin-2-yloxy)-ethoxy]-5-(4-chlorophenyl)-4-pyrimidinyl]-amide (198 mg). $t_R$=5.32 (LC); [M+H]$^+$=592.68 (ES+).

Examples 15-202

The corresponding starting materials are treated in a manner according to the procedures given in examples 1'-14 to give the compounds as listed in Tables 3-36.

TABLE 3

| Ex. No. | R$^1$ | R$^2$ | LC-MS |
|---|---|---|---|
| 15 | benzyl | 5-methoxy-pyrimidin-2-yl-O(CH$_2$)$_2$ | $t_R$ = 5.00 [M + H]$^+$: 543.18 |
| 16 | benzyl | 5-methyl-pyrimidin-2-yl-O(CH$_2$)$_2$ | $t_R$ = 4.95 [M + H]$^+$: 527.28 |
| 17 | 2-pyridylmethyl | HO-(CH$_2$)- | $t_R$ = 3.28 [M + H]$^+$: 435.65 |
| 18 | 2-pyridylmethyl | 5-bromo-pyrimidin-2-yl-O(CH$_2$)$_2$ | $t_R$ = 4.46 [M + H]$^+$: 594.25 |
| 19 | 2-pyridylmethyl | 5-methoxy-pyrimidin-2-yl-O(CH$_2$)$_2$ | $t_R$ = 4.03 [M + H]$^+$: 544.10 |

TABLE 3-continued

| Ex. No. | R$^1$ | R$^2$ | LC-MS |
|---|---|---|---|
| 20 | 2-thienylmethyl | 5-bromo-pyrimidin-2-yl-O(CH$_2$)$_2$ | $t_R$ = 5.21 [M + H]$^+$: 599.20 |
| 21 | 2-thienylmethyl | 5-methoxy-pyrimidin-2-yl-O(CH$_2$)$_2$ | $t_R$ = 4.84 [M + H]$^+$: 548.97 |

TABLE 4

| Ex. No. | R$^1$ | R$^2$ | LC-MS |
|---|---|---|---|
| 22 | 2-thienylmethyl | 5-trifluoromethyl-pyridin-2-yl-O(CH$_2$)$_2$ | $t_R$ = 5.67 [M + H]$^+$: 585.75 |
| 23 | 2-furylmethyl | 5-methoxy-pyrimidin-2-yl-O(CH$_2$)$_2$ | $t_R$ = 4.67 [M + H]$^+$: 532.77 |
| 24 | 2-furylmethyl | 5-bromo-pyrimidin-2-yl-O(CH$_2$)$_2$ | $t_R$ = 5.07 [M + H]$^+$: 582.71 |

TABLE 5

(structure with R¹NH-S(O)₂-NH-pyrimidine-phenyl, OR², 2-pyrimidinyl substituent)

| Ex. No. | R¹ | R² | LC-MS |
|---|---|---|---|
| 25 | benzyl | HO-propyl | $t_R = 4.07$ $[M + H]^+$: 479.11 |
| 26 | benzyl | 5-bromo-2-(O(CH₂)₂)-pyrimidinyl | $t_R = 4.88$ $[M + H]^+$: 637.54 |
| 27 | benzyl | 5-methoxy-2-(O(CH₂)₂)-pyrimidinyl | $t_R = 4.51$ $[M - H]^+$: 584.93 |

TABLE 6

(structure with R¹NH-S(O)₂-NH-pyrimidine-(4-ethylphenyl), OR²)

| Ex. No. | R¹ | R² | LC-MS |
|---|---|---|---|
| 28 | benzyl | HO-propyl | $t_R = 4.52$ $[M + H]^+$: 429.14 |

TABLE 6-continued

| Ex. No. | R¹ | R² | LC-MS |
|---|---|---|---|
| 29 | benzyl | 5-bromo-2-(O(CH₂)₂)-pyrimidinyl | $t_R = 5.48$ $[M + H]^+$: 585.38 |
| 30 | benzyl | 5-methoxy-2-(O(CH₂)₂)-pyrimidinyl | $t_R = 5.12$ $[M + H]^+$: 537.22 |

(structure with R¹NH-S(O)₂-NH-pyrimidine-(4-methylphenyl), OR², 4-pyridyl substituent)

| Ex. No. | R¹ | R² | LC-MS |
|---|---|---|---|
| 31 | benzyl | HO-propyl | $t_R = 3.99$ $[M + H]^+$: 492.23 |
| 32 | benzyl | 5-bromo-2-(O(CH₂)₂)-pyrimidinyl | $t_R = 5.04$ $[M + H]^+$: 650.50 |

TABLE 7

| Ex. No. | R¹ | R² | LC-MS |
|---|---|---|---|

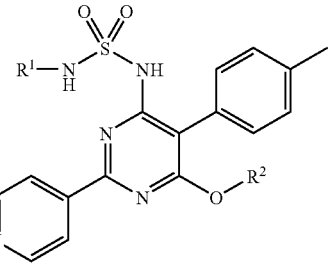

TABLE 7-continued

| Ex. No. | R¹ | R² | LC-MS |
|---|---|---|---|
| 33 | benzyl | 5-(methylthio)pyrimidin-2-yl-O(CH₂)₂ | $t_R$ = 5.00 [M + H]⁺: 616.18 |
| 34 | benzyl | pyridin-2-yl-NHC(O)O(CH₂)₂ | $t_R$ = 4.47 [M + H]⁺: 612.41 |
| 35 | 1,3-benzodioxol-5-ylmethyl | HO(CH₂)₃ | $t_R$ = 4.27 [M + H]⁺: 459.15 |

TABLE 8

| Ex. No. | R¹ | R² | LC-MS |
|---|---|---|---|
| 36 | benzyl | HO(CH₂)₃ | $t_R$ = 4.13 [M + H]⁺: 525.17 |
| 37 | benzyl | 5-bromopyrimidin-2-yl-O(CH₂)₂ | $t_R$ = 4.87 [M + H]⁺: 682.50 |
| 38 | benzyl | 5-methoxypyrimidin-2-yl-O(CH₂)₂ | $t_R$ = 4.55 [M + H]⁺: 631.05 |
| 39 | benzyl | pyrimidin-2-yl-O(CH₂)₂ | $t_R$ = 4.38 [M + H]⁺: 603.45 |
| 40 | benzyl | 5-(trifluoromethyl)pyridin-2-yl-O(CH₂)₂ | $t_R$ = 5.31 [M + H]⁺: 670.27 |
| 41 | benzyl | pyridin-2-yl-NHC(O)O(CH₂)₂ | $t_R$ = 4.36 [M + H]⁺: 645.11 |
| 42 | benzyl | pyrazin-2-yl-NHC(O)O(CH₂)₂ | $t_R$ = 4.29 [M + H]⁺: 646.12 |

TABLE 9

| Ex. No. | R¹ | R² | LC-MS |
|---|---|---|---|
| 43 | benzyl | -(CH₂)₂-O-C(O)-NH-phenyl | $t_R$ = 4.89<br>[M + H]⁺: 644.24 |
| 44 | benzyl | propargyl (HC≡C-CH₂-) | $t_R$ = 4.60<br>[M + H]⁺: 519.18 |
| 45 | benzyl | allyl (CH₂=CH-CH₂-) | $t_R$ = 4.74<br>[M + H]⁺: 521.21 |
| 46 | benzyl | (tetrahydrofuran-2-yl)methyl | $t_R$ = 4.71<br>[M + H]⁺: 565.66 |
| 47 | 4-methoxybenzyl | HO-(CH₂)₃- | $t_R$ = 4.10<br>[M + H]⁺: 555.59 |
| 48 | 4-methoxybenzyl | -(CH₂)₂-O-(5-bromopyrimidin-2-yl) | $t_R$ = 4.82<br>[M + H]⁺: 713.18 |
| 49 | 4-methoxybenzyl | -(CH₂)₂-O-(5-methoxypyrimidin-2-yl) | $t_R$ = 4.52<br>[M + H]⁺: 663.54 |

TABLE 10

| Ex. No. | R¹ | R² | LC-MS |
|---|---|---|---|
| 50 | 4-methoxybenzyl | -(CH₂)₂-O-C(O)-NH-(pyridin-2-yl) | $t_R$ = 4.32<br>[M + H]⁺: 675.34 |

TABLE 10-continued
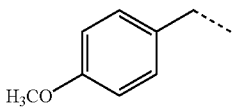
| Ex. No. | R¹ | R² | LC-MS |
|---|---|---|---|
| 51 |  | 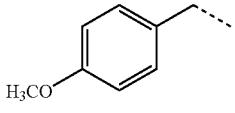 H₃C | $t_R$ = 4.51<br>[M + H]⁺: 524.91 |
| 52 | 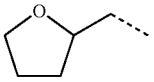 | 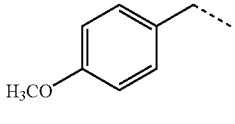 | $t_R$ = 4.67<br>[M + H]⁺: 595.20 |
| 53 | 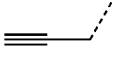 | 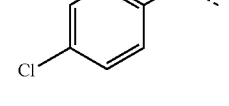 | $t_R$ = 4.65<br>[M + H]⁺: 549.33 |
| 54 |  | HO 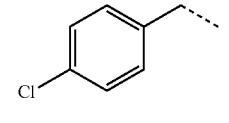 | $t_R$ = 4.35<br>[M + H]⁺: 559.30 |
| 55 | 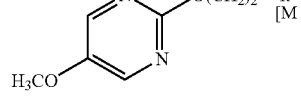 | 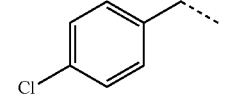 | $t_R$ = 4.79<br>[M + H]⁺: 667.34 |
| 56 | 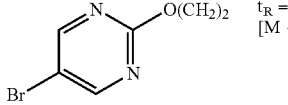 | 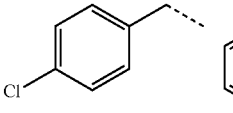 | $t_R$ = 5.11<br>[M + H]⁺: 717.09 |
TABLE 11
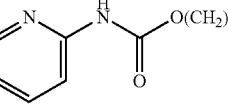
| Ex. No. | R¹ | R² | LC-MS |
|---|---|---|---|
| 57 | (4-Cl-benzyl) | (pyridin-2-yl-NHC(O)O(CH₂)₂) | $t_R$ = 4.71<br>[M − H]⁺: 678.68 |

TABLE 11-continued

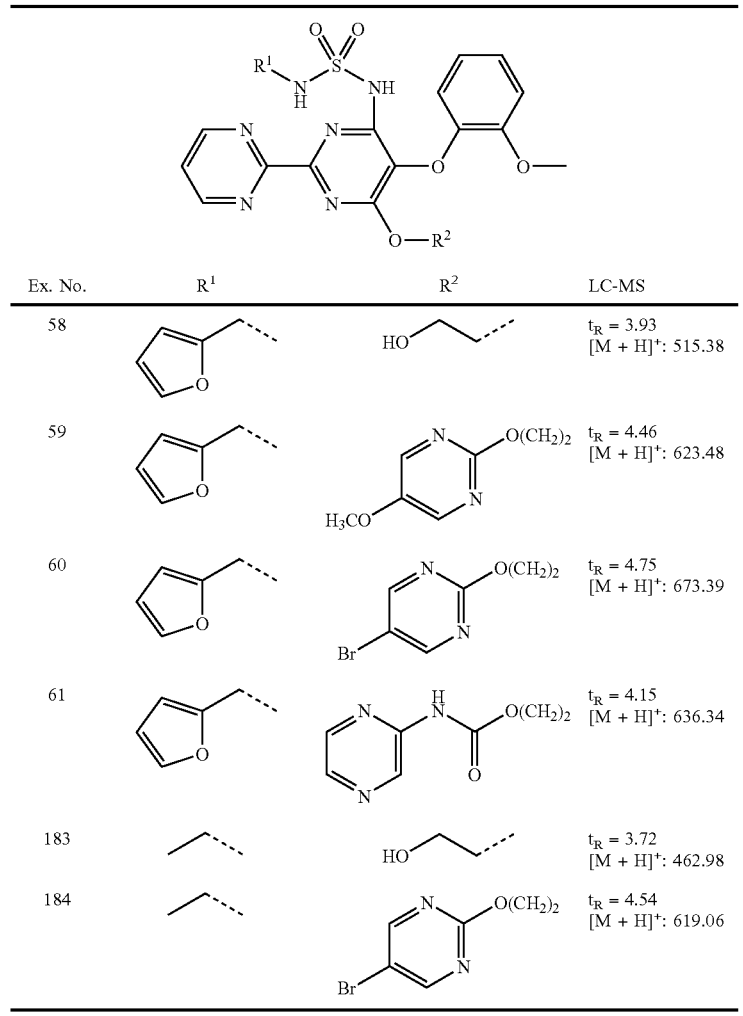

| Ex. No. | R¹ | R² | LC-MS |
|---|---|---|---|
| 58 | furan-2-yl-CH₂ | HO(CH₂)₃ | $t_R = 3.93$ $[M + H]^+$: 515.38 |
| 59 | furan-2-yl-CH₂ | 5-methoxy-pyrimidin-2-yl-O(CH₂)₂ | $t_R = 4.46$ $[M + H]^+$: 623.48 |
| 60 | furan-2-yl-CH₂ | 5-bromo-pyrimidin-2-yl-O(CH₂)₂ | $t_R = 4.75$ $[M + H]^+$: 673.39 |
| 61 | furan-2-yl-CH₂ | pyrazin-2-yl-NHC(O)O(CH₂)₂ | $t_R = 4.15$ $[M + H]^+$: 636.34 |
| 183 | CH₃CH₂CH₂ | HO(CH₂)₃ | $t_R = 3.72$ $[M + H]^+$: 462.98 |
| 184 | CH₃CH₂CH₂ | 5-bromo-pyrimidin-2-yl-O(CH₂)₂ | $t_R = 4.54$ $[M + H]^+$: 619.06 |

TABLE 12

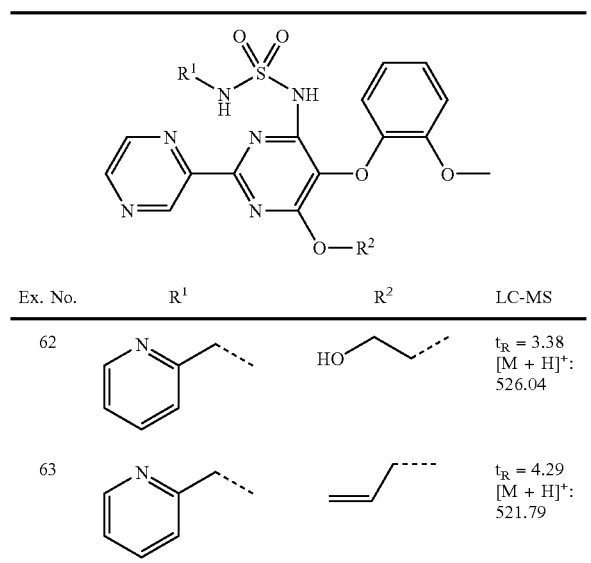

| Ex. No. | R¹ | R² | LC-MS |
|---|---|---|---|
| 62 | pyridin-2-yl-CH₂ | HO(CH₂)₃ | $t_R = 3.38$ $[M + H]^+$: 526.04 |
| 63 | pyridin-2-yl-CH₂ | CH₂=CHCH₂ | $t_R = 4.29$ $[M + H]^+$: 521.79 |

TABLE 12-continued

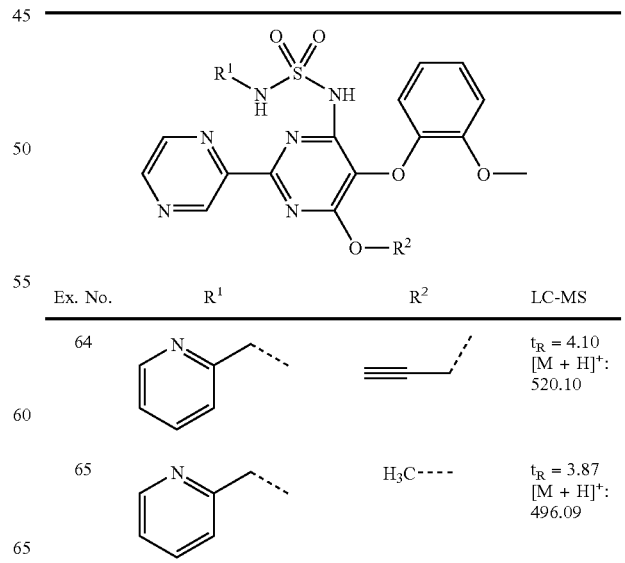

| Ex. No. | R¹ | R² | LC-MS |
|---|---|---|---|
| 64 | pyridin-2-yl-CH₂ | HC≡CCH₂ | $t_R = 4.10$ $[M + H]^+$: 520.10 |
| 65 | pyridin-2-yl-CH₂ | H₃C | $t_R = 3.87$ $[M + H]^+$: 496.09 |

TABLE 12-continued

Structure: pyrazinyl-pyrimidine with R¹-NH-S(O)₂-NH- and 2-methoxyphenoxy, O-R² substituents

| Ex. No. | R¹ | R² | LC-MS |
|---|---|---|---|
| 66 | pyridin-2-ylmethyl | (5-bromopyrimidin-2-yl)-O(CH₂)₂- | $t_R$ = 4.40 [M + H]⁺: 683.15 |
| 67 | benzyl | HO(CH₂)₃- | $t_R$ = 4.30 [M + H]⁺: 525.25 |
| 68 | benzyl | H₃C- | $t_R$ = 4.84 [M − H]⁺: 493.13 |

TABLE 13

Structure: pyrazinyl-pyrimidine with R¹-NH-S(O)₂-NH- and 2-methoxyphenoxy, O-R² substituents

| Ex. No. | R¹ | R² | LC-MS |
|---|---|---|---|
| 69 | benzyl | propargyl (CH₂-C≡CH) | $t_R$ = 4.95 [M − H]⁺: 517.58 |
| 70 | benzyl | allyl-CH₂- (but-3-enyl) | $t_R$ = 5.13 [M + H]⁺: 521.30 |
| 71 | benzyl | (5-bromopyrimidin-2-yl)-O(CH₂)₂- | $t_R$ = 5.22 [M + H]⁺: 683.42 |

TABLE 14

Structure: pyridin-4-yl-pyrimidine with R¹-NH-S(O)₂-NH- and 2-methoxyphenoxy, O-R² substituents

| Ex. No. | R¹ | R² | LC-MS |
|---|---|---|---|
| 72 | benzyl | HO(CH₂)₃- | $t_R$ = 3.79 [M + H]⁺: 524.28 |
| 73 | benzyl | (5-bromopyrimidin-2-yl)-O(CH₂)₂- | $t_R$ = 4.76 [M + H]⁺: 681.59 |
| 74 | benzyl | (5-methylthiopyrimidin-2-yl)-O(CH₂)₂- | $t_R$ = 4.70 [M + H]⁺: 648.25 |
| 75 | benzyl | (pyridin-2-yl)NHC(O)O(CH₂)₂- | $t_R$ = 4.30 [M + H]⁺: 645.65 |
| 76 | thiophen-2-ylmethyl | HO(CH₂)₃- | $t_R$ = 3.73 [M + H]⁺: 530.25 |
| 77 | thiophen-2-ylmethyl | propargyl (CH₂-C≡CH) | $t_R$ = 4.38 [M + H]⁺: 524.23 |
| 78 | thiophen-2-ylmethyl | but-3-enyl | $t_R$ = 4.59 [M + H]⁺: 526.10 |

TABLE 15

[Structure: pyrimidine core with R¹-NH-S(O)₂-NH- group, 2-pyridyl, 2-methoxyphenoxy, and O-R² substituents]

| Ex. No. | R¹ | R² | LC-MS |
|---|---|---|---|
| 79 | 2-thienylmethyl | H₃C– | t_R = 4.36; [M + H]⁺: 500.14 |
| 80 | 2-thienylmethyl | 5-bromo-2-(pyrimidinyl)-O(CH₂)₂ | t_R = 4.82; [M + H]⁺: 688.54 |
| 81 | 2-thienylmethyl | pyridin-2-yl-NH-C(O)-O(CH₂)₂ | t_R = 4.25; [M + H]⁺: 650.09 |
| 82 | benzo[1,3]dioxol-5-ylmethyl | HC≡C-CH₂-CH₂– | t_R = 4.43; [M + H]⁺: 562.16 |

TABLE 16 (and TABLE 16-continued)

[Structure: pyrimidine core with R¹-NH-S(O)₂-NH- group, 2-cyclopropyl, 2-methoxyphenoxy, and O-R² substituents]

| Ex. No. | R¹ | R² | LC-MS |
|---|---|---|---|
| 83 | pyridin-2-ylmethyl | HO-(CH₂)₃– | t_R = 3.38; [M + H]⁺: 488.30 |
| 84 | pyridin-2-ylmethyl | 5-bromopyrimidin-2-yl-O(CH₂)₂ | t_R = 4.46; [M + H]⁺: 646.17 |
| 85 | pyridin-2-ylmethyl | 5-methoxypyrimidin-2-yl-O(CH₂)₂ | t_R = 4.15; [M + H]⁺: 596.31 |
| 86 | pyridin-2-ylmethyl | pyridin-2-yl-NH-C(O)-O(CH₂)₂ | t_R = 3.96; [M + H]⁺: 608.69 |
| 87 | benzyl | HO-(CH₂)₃– | t_R = 4.77; [M + H]⁺: 488.18 |
| 88 | benzyl | 5-bromopyrimidin-2-yl-O(CH₂)₂ | t_R = 5.89; [M + H]⁺: 644.83 |

TABLE 16-continued

[Structure: R¹-NH-S(O)₂-NH-pyrimidine core with cyclopropyl, 2-methoxyphenoxy, and O-R² substituents]

| Ex. No. | R¹ | R² | LC-MS |
|---|---|---|---|
| 89 | benzyl | -(CH₂)₂-O-(5-methoxypyrimidin-2-yl) | $t_R$ = 5.56 [M + H]⁺: 595.20 |

TABLE 17

[Structure: R¹-NH-S(O)₂-NH-pyrimidine core with cyclopropyl, 2-methoxyphenoxy, and O-R² substituents]

| Ex. No. | R¹ | R² | LC-MS |
|---|---|---|---|
| 90 | benzyl | -(CH₂)₂-O-(5-methylthiopyrimidin-2-yl) | $t_R$ = 5.82 [M + H]⁺: 611.19 |
| 91 | benzyl | -(CH₂)₂-O-C(O)NH-(pyridin-2-yl) | $t_R$ = 5.31 [M + H]⁺: 607.32 |

TABLE 18

[Structure: R¹-NH-S(O)₂-NH-pyrimidine core with 2-methoxyphenoxy and O-R² substituents]

| Ex. No. | R¹ | R² | LC-MS |
|---|---|---|---|
| 92 | (pyridin-2-yl)methyl | HO-(CH₂)₃- | $t_R$ = 2.54 [M + H]⁺: 448.08 |

TABLE 18-continued

[Structure: R¹-NH-S(O)₂-NH-pyrimidine core with 2-methoxyphenoxy and O-R² substituents]

| Ex. No. | R¹ | R² | LC-MS |
|---|---|---|---|
| 93 | (pyridin-2-yl)methyl | -(CH₂)₂-O-(5-bromopyrimidin-2-yl) | $t_R$ = 4.20 [M + H]⁺: 605.54 |
| 94 | (pyridin-2-yl)methyl | -(CH₂)₂-O-(5-methoxypyrimidin-2-yl) | $t_R$ = 3.82 [M + H]⁺: 556.15 |
| 95 | benzyl | HO-(CH₂)₃- | $t_R$ = 4.14 [M + H]⁺: 447.26 |
| 96 | benzyl | -(CH₂)₂-O-(5-bromopyrimidin-2-yl) | $t_R$ = 5.10 [M + H]⁺: 604.67 |
| 97 | benzyl | -(CH₂)₂-O-(5-methylthiopyrimidin-2-yl) | $t_R$ = 5.01 [M + H]⁺: 571.18 |
| 98 | benzyl | -(CH₂)₂-O-C(O)NH-(pyridin-2-yl) | $t_R$ = 4.53 [M + H]⁺: 567.23 |

TABLE 19

[Structure: R¹-NH-S(O)₂-NH-pyrimidine core with 4-bromophenyl and O-R² substituents]

| Ex. No. | R¹ | R² | LC-MS |
|---|---|---|---|
| 99 | benzyl | HO-(CH₂)₃- | $t_R$ = 4.46 [M + H]⁺: 481.20 |

TABLE 19-continued

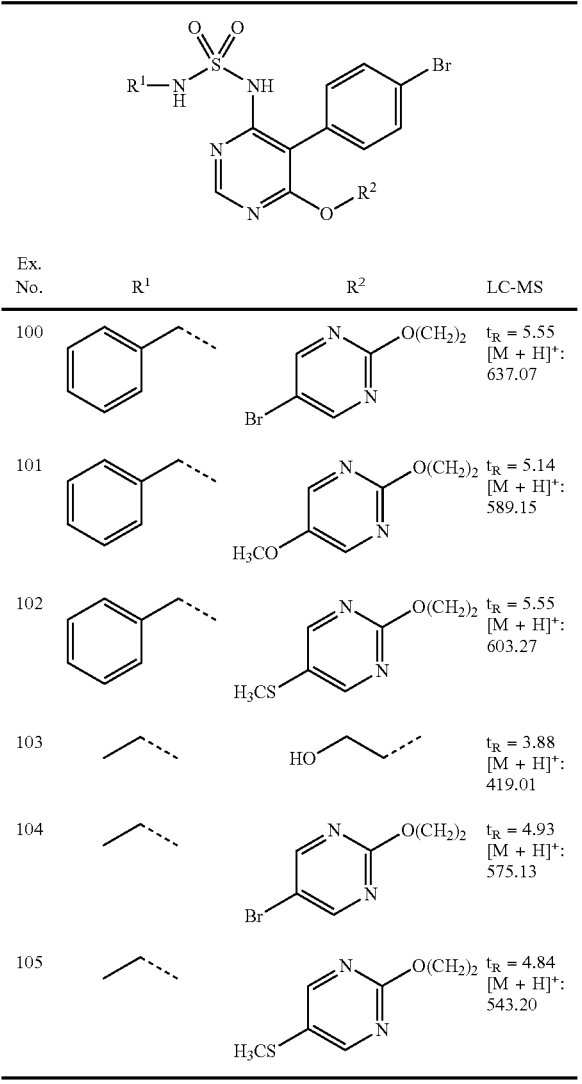

| Ex. No. | R¹ | R² | LC-MS |
|---|---|---|---|
| 100 | benzyl | 5-bromo-pyrimidin-2-yl-O(CH₂)₂ | $t_R$ = 5.55 [M + H]⁺: 637.07 |
| 101 | benzyl | 5-methoxy-pyrimidin-2-yl-O(CH₂)₂ | $t_R$ = 5.14 [M + H]⁺: 589.15 |
| 102 | benzyl | 5-methylthio-pyrimidin-2-yl-O(CH₂)₂ | $t_R$ = 5.55 [M + H]⁺: 603.27 |
| 103 | propyl | HO(CH₂)₃ | $t_R$ = 3.88 [M + H]⁺: 419.01 |
| 104 | propyl | 5-bromo-pyrimidin-2-yl-O(CH₂)₂ | $t_R$ = 4.93 [M + H]⁺: 575.13 |
| 105 | propyl | 5-methylthio-pyrimidin-2-yl-O(CH₂)₂ | $t_R$ = 4.84 [M + H]⁺: 543.20 |

TABLE 20

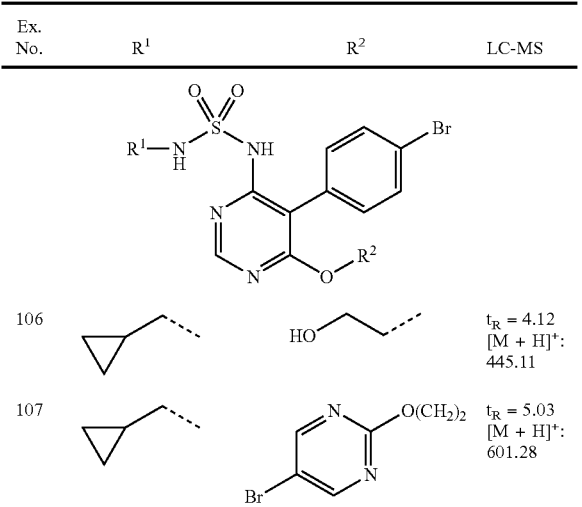

| Ex. No. | R¹ | R² | LC-MS |
|---|---|---|---|
| 106 | cyclopropylmethyl | HO(CH₂)₃ | $t_R$ = 4.12 [M + H]⁺: 445.11 |
| 107 | cyclopropylmethyl | 5-bromo-pyrimidin-2-yl-O(CH₂)₂ | $t_R$ = 5.03 [M + H]⁺: 601.28 |
| 108 | cyclopropylmethyl | 5-methylthio-pyrimidin-2-yl-O(CH₂)₂ | $t_R$ = 4.98 [M + H]⁺: 568.44 |

TABLE 20-continued

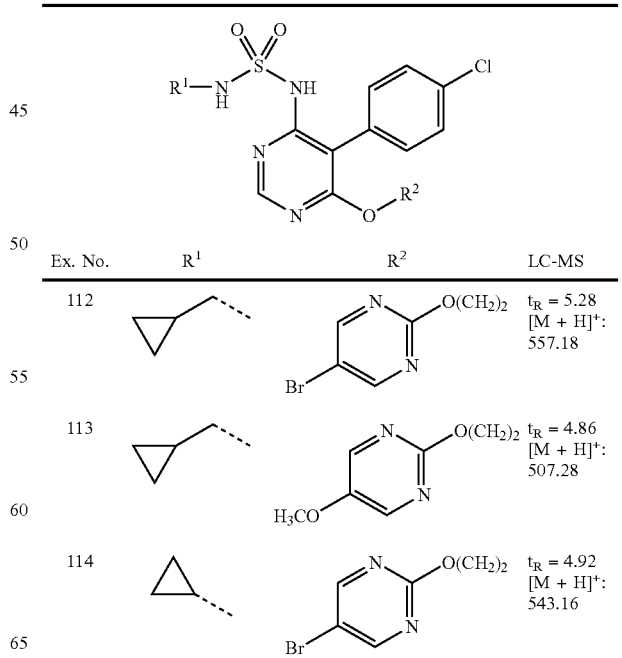

| Ex. No. | R¹ | R² | LC-MS |
|---|---|---|---|
| 109 | benzyl | 5-bromo-pyrimidin-2-yl-O(CH₂)₂ | $t_R$ = 4.92 [M + H]⁺: 670.30 |
| 110 | benzyl | 5-methylthio-pyrimidin-2-yl-O(CH₂)₂ | $t_R$ = 5.07 [M + H]⁺: 636.34 |
| 111 | benzyl | 5-methoxy-pyrimidin-2-yl-O(CH₂)₂ | $t_R$ = 4.76 [M + H]⁺: 620.07 |

TABLE 21

| Ex. No. | R¹ | R² | LC-MS |
|---|---|---|---|
| 112 | cyclopropylmethyl | 5-bromo-pyrimidin-2-yl-O(CH₂)₂ | $t_R$ = 5.28 [M + H]⁺: 557.18 |
| 113 | cyclopropylmethyl | 5-methoxy-pyrimidin-2-yl-O(CH₂)₂ | $t_R$ = 4.86 [M + H]⁺: 507.28 |
| 114 | cyclopropyl | 5-bromo-pyrimidin-2-yl-O(CH₂)₂ | $t_R$ = 4.92 [M + H]⁺: 543.16 |

TABLE 21-continued

Structure: R¹—NH—S(O)₂—NH attached to pyrimidine bearing 4-chlorophenyl and OR²

| Ex. No. | R¹ | R² | LC-MS |
|---|---|---|---|
| 115 | ethyl | 5-bromopyrimidin-2-yl-O(CH₂)₂ | $t_R$ = 4.87 [M + H]$^+$: 531.13 |
| 116 | ethyl | 5-(methylthio)pyrimidin-2-yl-O(CH₂)₂ | $t_R$ = 4.78 [M + H]$^+$: 497.24 |
| 117 | n-butyl | 5-bromopyrimidin-2-yl-O(CH₂)₂ | $t_R$ = 5.32 [M + H]$^+$: 559.19 |
| 118 | n-butyl | 5-(methylthio)pyrimidin-2-yl-O(CH₂)₂ | $t_R$ = 5.23 [M + H]$^+$: 525.31 |

TABLE 22

Structure: R¹—NH—S(O)₂—NH attached to pyrimidine bearing 4-methylphenyl and OR²

| Ex. No. | R¹ | R² | LC-MS |
|---|---|---|---|
| 119 | cyclopropylmethyl | 5-bromopyrimidin-2-yl-O(CH₂)₂ | $t_R$ = 5.20 [M + H]$^+$: 537.14 |
| 120 | cyclopropylmethyl | 5-methoxypyrimidin-2-yl-O(CH₂)₂ | $t_R$ = 4.77 [M + H]$^+$: 487.25 |
| 121 | cyclopropylmethyl | pyrimidin-2-yl-O(CH₂)₂ | $t_R$ = 4.56 [M + H]$^+$: 456.89 |
| 144 | 1,3-benzodioxol-5-ylmethyl | HO(CH₂)₃ | $t_R$ = 4.27 [M + H]$^+$: 459.15 |
| 145 | 1,3-benzodioxol-5-ylmethyl | 5-bromopyrimidin-2-yl-O(CH₂)₂ | $t_R$ = 5.77 [M + H]$^+$: 616.66 |

TABLE 22-continued

| Ex. No. | R¹ | R² | LC-MS |
|---|---|---|---|
| 146 | benzo[1,3]dioxol-5-ylmethyl | 5-methoxy-pyrimidin-2-yl-O(CH₂)₂ | $t_R$ = 6.01<br>[M + H]⁺: 567.36 |
| 147 | benzo[1,3]dioxol-5-ylmethyl | 5-(methylthio)-pyrimidin-2-yl-O(CH₂)₂ | $t_R$ = 5.22<br>[M + H]⁺: 582.88 |

TABLE 23

| Ex. No. | R¹ | R² | LC-MS |
|---|---|---|---|
| 122 | pyridin-4-yl | HO(CH₂)₃ | $t_R$ = 3.63<br>[M + H]⁺: 488.49 |
| 123 | pyridin-4-yl | 5-bromo-pyrimidin-2-yl-O(CH₂)₂ | $t_R$ = 4.66<br>[M + H]⁺: 646.30 |
| 124 | pyridin-4-yl | 5-methoxy-pyrimidin-2-yl-O(CH₂)₂ | $t_R$ = 4.29<br>[M + H]⁺: 596.44 |
| 125 | pyrimidin-2-yl | HO(CH₂)₃ | $t_R$ = 3.96<br>[M + H]⁺: 489.56 |
| 126 | pyrimidin-2-yl | 5-bromo-pyrimidin-2-yl-O(CH₂)₂ | $t_R$ = 4.79<br>[M + H]⁺: 645.07 |

TABLE 23-continued

| Ex. No. | R¹ | R² | LC-MS |
|---|---|---|---|
| 127 | pyrimidin-2-yl | 5-methoxy-pyrimidin-2-yl-O(CH₂)₂ | $t_R$ = 4.47<br>[M + H]⁺: 597.31 |
| 128 | pyrimidin-2-yl | propargyl | $t_R$ = 4.47<br>[M + H]⁺: 483.34 |

TABLE 24

| Ex. No. | R¹ | R² | LC-MS |
|---|---|---|---|
| 129 | pyridin-4-yl | HO(CH₂)₃ | $t_R$ = 4.29<br>[M + H]⁺: 530.49 |

TABLE 24-continued

Structure: cyclohexylmethyl-NH-S(=O)2-NH- attached to pyrimidine with R1 at 2-position, 2-methoxyphenoxy at 5-position, O-R2 at 6-position.

| Ex. No. | R¹ | R² | LC-MS |
|---|---|---|---|
| 130 | pyridin-4-yl | 5-bromo-pyrimidin-2-yl-O(CH₂)₂ | $t_R$ = 5.35 [M + H]⁺: 688.27 |
| 131 | pyridin-4-yl | 5-methoxy-pyrimidin-2-yl-O(CH₂)₂ | $t_R$ = 4.93 [M + H]⁺: 638.64 |
| 132 | pyrimidin-2-yl | HO(CH₂)₂– | $t_R$ = 4.70 [M + H]⁺: 531.54 |
| 133 | pyrimidin-2-yl | 5-bromo-pyrimidin-2-yl-O(CH₂)₂ | $t_R$ = 5.39 [M + H]⁺: 689.26 |
| 134 | pyrimidin-2-yl | 5-methoxy-pyrimidin-2-yl-O(CH₂)₂ | $t_R$ = 5.06 [M + H]⁺: 639.36 |
| 135 | pyrimidin-2-yl | 5-trifluoromethyl-pyridin-2-yl-O(CH₂)₂ | $t_R$ = 5.83 [M + H]⁺: 676.34 |

TABLE 25

Structure: n-butyl-NH-S(=O)2-NH- attached to pyrimidine with R1 at 2-position, 2-methoxyphenoxy at 5-position, O-R2 at 6-position.

| Ex. No. | R¹ | R² | LC-MS |
|---|---|---|---|
| 136 | phenyl | HO(CH₂)₂– | $t_R$ = 4.11 [M + H]⁺: 491.29 |
| 137 | phenyl | 5-bromo-pyrimidin-2-yl-O(CH₂)₂ | $t_R$ = 4.88 [M + H]⁺: 649.18 |
| 138 | phenyl | 5-methylthio-pyrimidin-2-yl-O(CH₂)₂ | $t_R$ = 4.82 [M + H]⁺: 615.67 |

TABLE 26

Structure: 4-fluorobenzyl-NH-S(=O)2-NH- attached to pyrimidine with R1 at 2-position, 2-methoxyphenoxy at 5-position, O-R2 at 6-position.

| Ex. No. | R¹ | R² | LC-MS |
|---|---|---|---|
| 139 | pyrimidin-2-yl | HO(CH₂)₂– | $t_R$ = 4.27 [M + H]⁺: 543.37 |
| 140 | pyrimidin-2-yl | H₃C– | $t_R$ = 4.55 [M + H]⁺: 513.31 |
| 141 | pyrimidin-2-yl | tetrahydrofuran-2-yl-methyl | $t_R$ = 4.70 [M + H]⁺: 583.52 |
| 142 | pyrimidin-2-yl | 5-bromo-pyrimidin-2-yl-O(CH₂)₂ | $t_R$ = 4.92 [M + H]⁺: 701.37 |
| 143 | pyrimidin-2-yl | 5-methoxy-pyrimidin-2-yl-O(CH₂)₂ | $t_R$ = 4.60 [M + H]⁺: 651.40 |

TABLE 27

| Ex. No. | R¹ | R² | LC-MS |
|---|---|---|---|
| 148 | 4-pyridyl | propargyl (CH₂-C≡CH) | $t_R$ = 4.43 [M + H]⁺: 562.16 |
| 149 | 4-pyridyl | H₃C---- | $t_R$ = 4.27 [M + H]⁺: 538.18 |

| Ex. No. | R¹ | R² | LC-MS |
|---|---|---|---|
| 150 | H | HO(CH₂)₂- | $t_R$ = 4.37 [M + H]⁺: 522.83 |
| 151 | H | 5-bromo-2-pyrimidinyl-O(CH₂)₂- | $t_R$ = 5.21 [M + H]⁺: 682.98 |
| 152 | H | 5-methoxy-2-pyrimidinyl-O(CH₂)₂- | $t_R$ = 4.86 [M + H]⁺: 631.19 |

TABLE 28

| Ex. No. | R¹ | R² | LC-MS |
|---|---|---|---|
| 153 | 4-pyridyl | HO(CH₂)₂- | $t_R$ = 3.15 [M − H]⁺: 523.09 |

TABLE 28-continued

| Ex. No. | R¹ | R² | LC-MS |
|---|---|---|---|
| 154 | 2-pyrimidinyl | HO(CH₂)₂- | $t_R$ = 3.20 [M + H]⁺: 526.44 |
| 155 | 2-pyrimidinyl | 5-(H₃CS)-2-pyrimidinyl-O(CH₂)₂- | $t_R$ = 3.96 [M + H]⁺: 650.39 |
| 156 | 2-pyrimidinyl | 5-bromo-2-pyrimidinyl-O(CH₂)₂- | $t_R$ = 4.00 [M + H]⁺: 684.29 |
| 157 | 2-pyrimidinyl | 2-thiazolyl-O(CH₂)₂- | $t_R$ = 3.86 [M + H]⁺: 609.32 |
| 158 | 4-pyridyl | 5-(H₃CS)-2-pyrimidinyl-O(CH₂)₂- | $t_R$ = 4.14 [M + H]⁺: 649.30 |

TABLE 29

| Ex. No. | R¹ | R² | LC-MS |
|---|---|---|---|
| 160 | 4-pyridyl | propargyl (CH₂-C≡CH) | $t_R$ = 4.58 [M + H]⁺: 548.41 |
| 161 | 4-pyridyl | H₃C---- | $t_R$ = 4.32 [M + H]⁺: 524.19 |

TABLE 29-continued

| Ex. No. | R¹ | R² | LC-MS |
|---|---|---|---|

(Structure: 4-methoxybenzyl-NH-S(=O)₂-NH- attached to pyrimidine with R¹, and 5-O-(2-Cl-5-methoxyphenyl), 6-OR²)

| 162 | H | HO-(CH₂)₃- | $t_R$ = 4.41 [M + H]⁺: 511.11 |
| 163 | H | 5-Br-pyrimidin-2-yl-O-(CH₂)₂- | $t_R$ = 5.26 [M + H]⁺: 668.91 |
| 164 | H | 5-H₃CO-pyrimidin-2-yl-O-(CH₂)₂- | $t_R$ = 4.98 [M + H]⁺: 619.17 |

TABLE 30

(Structure: 3,4-dimethoxybenzyl-NH-S(=O)₂-NH- attached to pyrimidine with R¹, and 5-O-(2-methoxyphenyl), 6-OR²)

| Ex. No. | R¹ | R² | LC-MS |
|---|---|---|---|
| 165 | pyrimidin-2-yl | HO-(CH₂)₃- | $t_R$ = 3.90 [M + H]⁺: 585.52 |
| 166 | pyrimidin-2-yl | 5-Br-pyrimidin-2-yl-O-(CH₂)₂- | $t_R$ = 4.69 [M + H]⁺: 743.19 |
| 167 | pyrimidin-2-yl | pyrimidin-2-yl-O-(CH₂)₂- | $t_R$ = 4.24 [M + H]⁺: 663.47 |
| 168 | pyrimidin-2-yl | PhNHC(=O)O-(CH₂)₂- | $t_R$ = 4.78 [M + H]⁺: 704.54 |

TABLE 31

(Structure: 3-methoxybenzyl-NH-S(=O)₂-NH- attached to pyrimidine with R¹, and 5-O-(2-methoxyphenyl), 6-OR²)

| Ex. No. | R¹ | R² | LC-MS |
|---|---|---|---|
| 169 | pyrimidin-2-yl | HO-(CH₂)₃- | $t_R$ = 4.16 [M + H]⁺: 555.69 |
| 170 | pyrimidin-2-yl | 5-Br-pyrimidin-2-yl-O-(CH₂)₂- | $t_R$ = 4.76 [M + H]⁺: 713.26 |
| 171 | pyrimidin-2-yl | pyrimidin-2-yl-O-(CH₂)₂- | $t_R$ = 4.45 [M + H]⁺: 633.64 |
| 172 | pyrimidin-2-yl | PhNHC(=O)O-(CH₂)₂- | $t_R$ = 4.98 [M + H]⁺: 674.55 |

TABLE 32

(Structure: 2-methoxybenzyl-NH-S(=O)₂-NH- attached to pyrimidine with R¹, and 5-O-(2-methoxyphenyl), 6-OR²)

| Ex. No. | R¹ | R² | LC-MS |
|---|---|---|---|
| 173 | pyrimidin-2-yl | HO-(CH₂)₃- | $t_R$ = 4.20 [M + H]⁺: 555.37 |
| 174 | pyrimidin-2-yl | 5-Br-pyrimidin-2-yl-O-(CH₂)₂- | $t_R$ = 4.99 [M + H]⁺: 713.35 |
| 175 | pyrimidin-2-yl | pyrimidin-2-yl-O-(CH₂)₂- | $t_R$ = 4.45 [M + H]⁺: 633.70 |
| 176 | pyrimidin-2-yl | PhNHC(=O)O-(CH₂)₂- | $t_R$ = 4.99 [M + H]⁺: 674.95 |

TABLE 33

[Structure: phenethyl-NH-S(O)₂-NH-pyrimidine with R¹ at 2-position, 2-methoxyphenoxy at 5-position, and O-R² at 6-position]

| Ex. No. | R¹ | R² | LC-MS |
|---|---|---|---|
| 177 | 4-pyridyl | H₃C---- | t_R = 4.54<br>[M + H]⁺: 508.22 |
| 178 | 4-pyridyl | -CH₂-C≡CH (propargyl) | t_R = 4.62<br>[M + H]⁺: 532.23 |
| 179 | 4-pyridyl | HO-CH₂CH₂CH₂- | t_R = 3.90<br>[M + H]⁺: 538.33 |

TABLE 33-continued

| Ex. No. | R¹ | R² | LC-MS |
|---|---|---|---|
| 180 | 4-pyridyl | CH₃-O-CH₂CH₂CH₂- | t_R = 4.46<br>[M + H]⁺: 552.27 |
| 181 | 4-pyridyl | PhNH-C(O)-O-(CH₂)₂- | t_R = 4.78<br>[M + H]⁺: 657.46 |
| 182 | 4-pyridyl | (5-bromopyrimidin-2-yl)-O-(CH₂)₂- | t_R = 4.91<br>[M + H]⁺: 696.51 |

TABLE 34

[Structure: R¹-S(O)₂-NH-pyrimidine with pyrimidin-2-yl at 2-position, 2-methoxyphenoxy at 5-position, and O-R² at 6-position]

| Ex. No. | R¹ | R² | LC-MS |
|---|---|---|---|
| 185 | PhCH₂-N(CH₃)- | H₃C---- | t_R = 4.84<br>[M + H]⁺: 507.15 |
| 186 | PhCH₂-N(CH₃)- | HO-CH₂CH₂CH₂- | t_R = 4.51<br>[M + H]⁺: 539.47 |
| 187 | PhCH₂-N(CH₃)- | (5-bromopyrimidin-2-yl)-O-(CH₂)₂- | t_R = 5.18<br>[M + H]⁺: 695.09 |

TABLE 34-continued

| Ex. No. | R¹ | R² | LC-MS |
|---|---|---|---|
| 188 | benzyl(methyl)amino | 5-methoxypyrimidin-2-yl-O(CH$_2$)$_2$ | $t_R$ = 4.86<br>[M + H]$^+$: 647.43 |
| 189 | morpholino | HO-CH$_2$CH$_2$- | $t_R$ = 3.56<br>[M + H]$^+$: 505.35 |
| 190 | morpholino | 5-bromopyrimidin-2-yl-O(CH$_2$)$_2$ | $t_R$ = 4.38<br>[M + H]$^+$: 663.05 |
| 191 | diethylamino | 5-(methylthio)pyrimidin-2-yl-O(CH$_2$)$_2$ | $t_R$ = 4.77<br>[M + H]$^+$: 615.32 |

TABLE 35

| Ex. No. | R¹ | R² | LC-MS |
|---|---|---|---|
| 192 | benzyl(methyl)amino | HO-CH$_2$CH$_2$CH$_2$- | $t_R$ = 4.84<br>[M + H]$^+$: 447.17 |
| 193 | benzyl(methyl)amino | 5-bromopyrimidin-2-yl-O(CH$_2$)$_2$ | $t_R$ = 5.66<br>[M + H]$^+$: 607.22 |
| 194 | benzyl(methyl)amino | 5-methoxypyrimidin-2-yl-O(CH$_2$)$_2$ | $t_R$ = 5.31<br>[M + H]$^+$: 557.42 |

TABLE 35-continued

[Structure: R¹-S(O)₂-NH attached to pyrimidine with 4-bromophenyl and O-R² substituents]

| Ex. No. | R¹ | R² | LC-MS |
|---|---|---|---|
| 195 | cyclopropyl-NH- | HOCH₂CH₂- | $t_R$ = 3.92 [M + H]⁺: 431.09 |
| 196 | cyclopropyl-NH- | 5-bromopyrimidin-2-yl-O(CH₂)₂- | $t_R$ = 4.99 [M + H]⁺: 587.13 |
| 197 | cyclopropyl-NH- | 5-(methylthio)pyrimidin-2-yl-O(CH₂)₂- | $t_R$ = 4.90 [M + H]⁺: 555.18 |

TABLE 36

[Structure: cyclopropyl-NH-S(O)₂-NH attached to pyrimidine with 2-methoxyphenoxy, O-R² and R¹ substituents]

| Ex. No. | R¹ | R² | LC-MS |
|---|---|---|---|
| 198 | pyrimidin-2-yl | pyrimidin-2-yl-O(CH₂)₂- | $t_R$ = 4.11 [M + H]⁺: 551.34 |
| 199 | pyrimidin-2-yl | 5-bromopyrimidin-2-yl-O(CH₂)₂- | $t_R$ = 4.61 [M + H]⁺: 633.37 |
| 200 | pyrimidin-2-yl | 5-methoxypyrimidin-2-yl-O(CH₂)₂- | $t_R$ = 4.35 [M + H]⁺: 583.40 |
| 201 | pyrimidin-2-yl | 5-(trifluoromethyl)pyridin-2-yl-O(CH₂)₂- | $t_R$ = 5.05 [M + H]⁺: 617.98 |
| 202 | pyridin-4-yl | 5-bromopyrimidin-2-yl-O(CH₂)₂- | $t_R$ = 4.51 [M + H]⁺: 632.16 |

Example 203-206

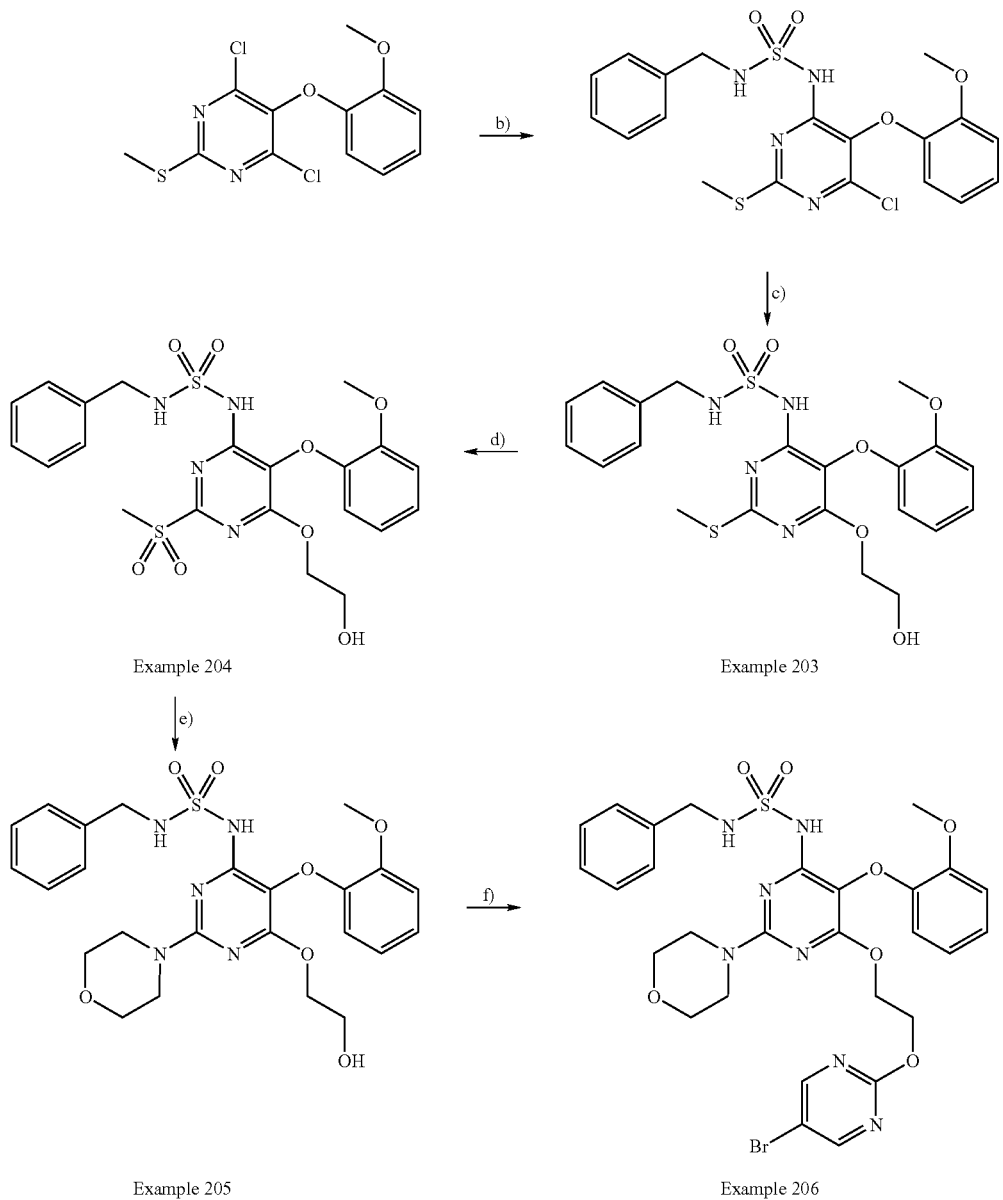

Example 204

Example 203

Example 205

Example 206 a) According to the procedures described in [5], the preparation of 4,6-dichloro-5-(2-methoxy-phenoxy)-2-methylsulfanyl-pyrimidine was achieved by the condensation of thiourea (6.4 g) with 2-(2-methoxy-phenoxy)-malonic acid dimethyl ester (20.32 g) followed by reacting the 2-mercapto-5-(2-methoxy-phenoxy)-pyrimidine-4,6-diol with methyliodide (5.9 ml) and subsequent chlorination with phosphorus oxychloride/N,N-dimethylaniline. Yield: 18.6 g; LC-MS: $t_R$=5.73; [M+H]$^+$=318.2.

b) 4,6-Dichloro-5-(2-methoxy-phenoxy)-2-methylsulfanyl-pyrimidine (1.5 g) was dissolved in DMSO (30 ml) and benzylsulfamic acid amide potassium salt (2.12 g, Referential Example 22) was added. Stirring was continued for 18 h. The reaction mixture was poured onto water, acidified by solid citric acid (1.9 g), cooled to 0° C. and the precipitate was filtered off and purified by column chromatography over silica gel with hexane/EtOAc=2/1 to give benzylsulfamic acid [6-chloro-5-(2-methoxy-phenoxy)-2-methylsulfanyl-pyrimidin-4-yl]-amide (1.75 g) as a white powder. LC-MS: $t_R$=5.27; [M+H]$^+$=467.04.

c) Benzylsulfamic acid [6-chloro-5-(2-methoxy-phenoxy)-2-methylsulfanyl-pyrimidin-4-yl]-amide (1.75 g) was added to a solution of potassium tert.-butylate (1.87 g) in ethylene glycol (30 ml) and stirred at 100° C. for 40 h. The reaction mixture was poured onto water (120 ml), acidified with solid citric acid (1.9 g) and cooled to 0° C. The precipitate was filtered off, washed with water and dried at HV to give benzylsulfamic acid [6-(2-hydroxy-ethoxy)-5-(2-methoxy-phenoxy)-2-methylsulfanyl-pyrimidin-4-yl]-amide (Example 203). LC-MS: $t_R$=4.70; [M+H]$^+$=493.09.

d) Benzylsulfamic acid [6-(2-hydroxy-ethoxy)-5-(2-methoxy-phenoxy)-2-methylsulfanyl-pyrimidin-4-yl]-amide (1.49 g) was dissolved in DCM (50 ml) and cooled to 0° C. followed by slow addition of m-chloroperbenzoic acid (1.65 g; 70%) dissolved in DCM (15 ml). Stirring was continued for 30 min at 0° C. and for 1.5 h at rt. The mixture was concentrated in vacuo until the product started to precipitate. The product was filtered off and purified by chromatography through silicagel with EtOAc/hexane=2:1 to give benzylsulfamic acid [6-(2-hydroxy-ethoxy)-2-methanesulfonyl-5-(2-methoxy-phenoxy)pyrimidin-4-yl]-amide (Example 204) (1.4 g) as a white powder. LC-MS: $t_R$=4.12; $[M+H]^+$=525.09.

e) Benzylsulfamic acid [6-(2-hydroxy-ethoxy)-2-methanesulfonyl-5-(2-methoxy-phenoxy)-pyrimidin-4-yl]-amide (85 mg) were dissolved in THF (2 ml) and morpholine (2 ml) was added. The reaction mixture was stirred at 45° C. for 48 hours, poured onto water, acidified with solid citric acid and extracted with EtOAc (2×). The combined EtOAc layers were washed with 10% citric acid solution and with brine, dried over magnesium sulfate, filtered and the solvent was evaporated. The crude product was purified by chromatography on plates with toluene/EtOAc=1/1 to give benzylsulfamic acid [6-(2-hydroxy-ethoxy)-5-(2-methoxy-phenoxy)-2-morpholin-4-yl-pyrimidin-4-yl]-amide (Example 205) (60 mg). LC-MS: $t_R$=4.69; $[M+H]^+$=532.15.

f) Benzylsulfamic acid [6-[2-(5-bromo-pyrimidin-2-yloxy)-ethoxy]-5-(2-methoxy-phenoxy)-2-morpolin-4-yl-pyrimidin-4-amide (Example 206) (40 mg) {LC-MS: $t_R$=5.63; $[M+H]^+$=690.50} was prepared accoridng to the procedure described in Examples 5, 12 and 14 from benzylsulfamic acid [6-(2-hydroxy-ethoxy)-5-(2-methoxy-phenoxy)-2-morpholin-4-yl-pyrimidin-4-yl]-amide (Example 205) (50 mg).

According to the procedures described for the preparation of Examples 203-206, the following compounds can be prepared:

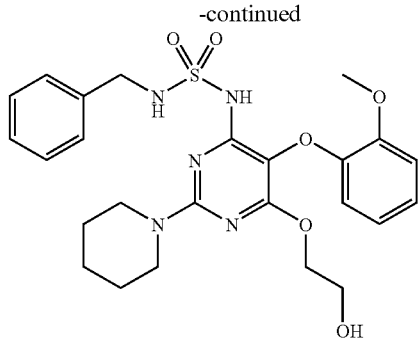

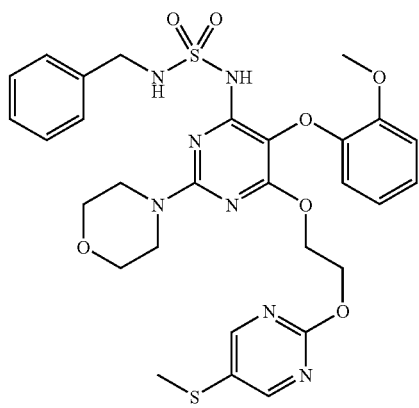

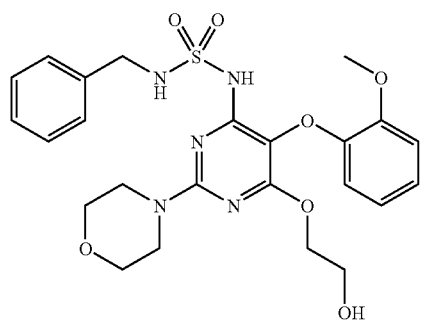

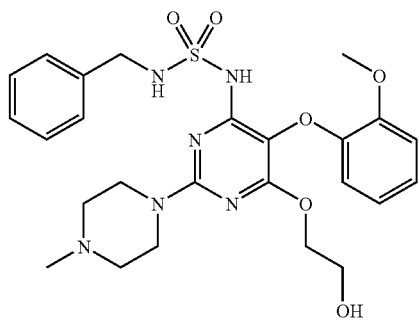

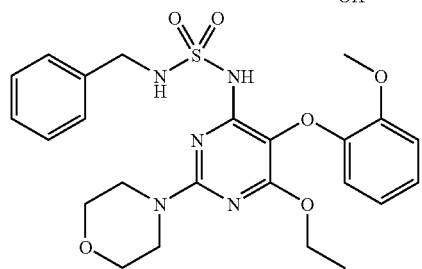

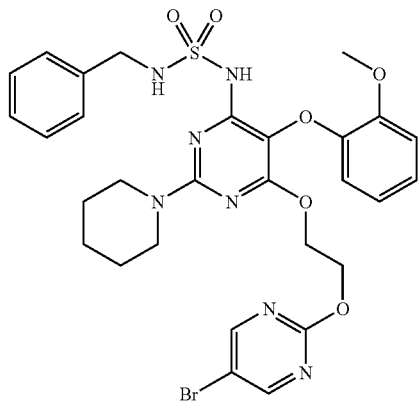

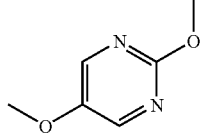

-continued

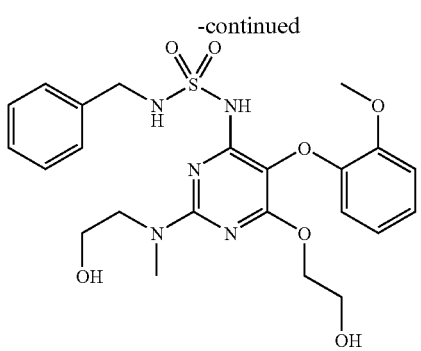

The preparation of compounds by the above described procedures is not limited to the molecules schematically depicted. Further variations, especially also in the sulfamide part of the molecule, can be achieved via the same pathway.

Example 207 off and recrystallized form EtOAc to give benzylsulfamic acid [6-chloro-2-(2-cyano-pyridin-4-yl)-5-(2-methoxy-phenoxy)-pyrimidin-4-yl]-amide (4.17 g). LC-MS: $t_R$=5.55; [M+H]$^+$=523.29.

c) Benzylsulfamic acid [6-chloro-2-(2-cyano-pyridin-4-yl)-5-(2-methoxy-phenoxy)-pyrimidin-4-yl]-amide (4.17 g) was dissolved in DMF (55 ml). Sodium azide (5.2 g) and ammonium chloride (4.28 g) were added and the mixture was stirred for 20 h at 80° C. Then the mixture was pored onto water and extracted with EtOAc. The layers were separated and the water layer was acidified with acetic acid to pH ~5 and extracted with EtOAc. The combined organic layers from the 2$^{nd}$ extraction were washed with brine, dried over magnesium sulfate, filtered and evaporated. The crude material was purified by chromatography over silicagel with EtOAc/MeOH/ammonia=5/1/0.5 to give benzylsulfamic acid [6-chloro-5-(2-methoxy-phenoxy)-2-[2-(1H-tetrazol-5-

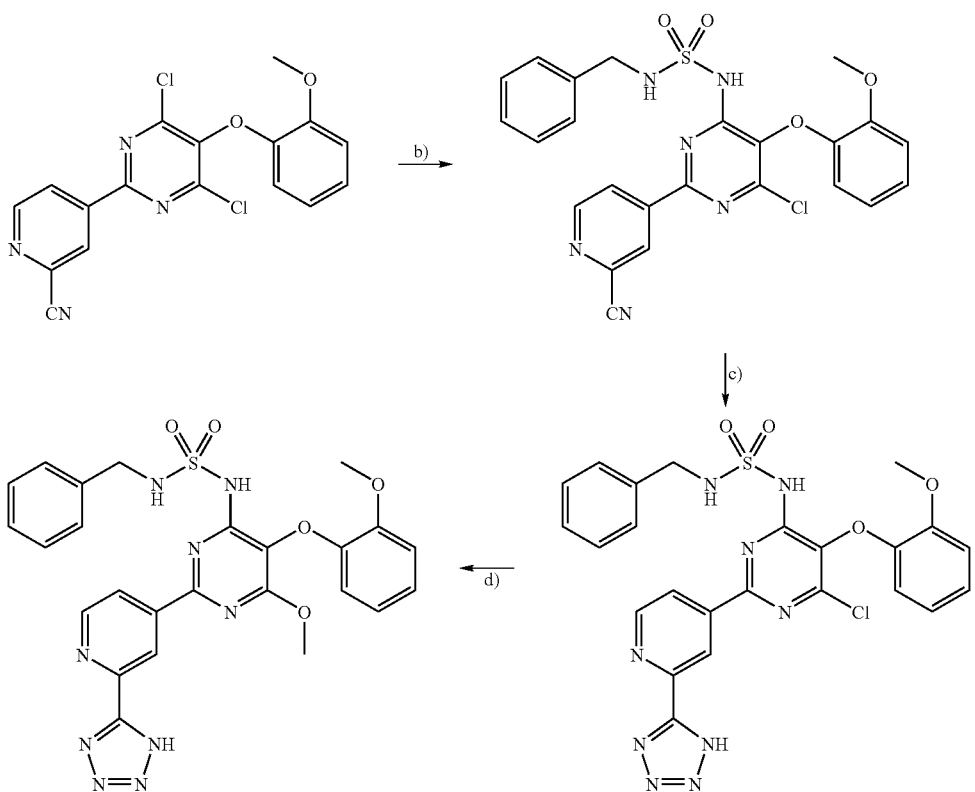

Example 207 a) 4-[4,6-Dichloro-5-(2-methoxy-phenoxy)-pyrimidin-2-yl]-pyridine-2-carbonitrile can be prepared as described in WO 96/19459 and WO 00/42035.

b) 4-[4,6-Dichloro-5-(2-methoxy-phenoxy)-pyrimidin-2-yl]-pyridine-2-carbonitrile (3.2 g) was dissolved in DMSO (20 ml), N-ethyldiisopropylamine (1.7 ml) and benzylsulfamic acid amide potassium salt (3.52 g) was added. The mixture was stirred for 18 h at rt, poured onto ice/water, acidified with solid citric acid and the precipitate was filtered yl)-pyridin-4-yl]-pyrimidin-4-yl]-amide (1.67 g). LC-MS: $t_R$=5.02; [M+H]$^+$=566.36.

d) According to the procedures described in Examples 1, 8 and 9, benzylsulfamic acid [6-chloro-5-(2-methoxy-phenoxy)-2-[2-(1H-tetrazol-5-yl pyridin-4-yl]-pyrimidin-4-yl]-amide (150 mg) was transformed to benzylsulfamic acid [6-methoxy-5-(2-methoxy-phenoxy)-2-[2-(1H-tetrazol-5-yl)-pyridin-4-yl]-pyrimidin-4-yl]-amide (50 mg) (Example 207). LC-MS: $t_R$=4.84; [M+H]$^+$=562.29.

Example 208

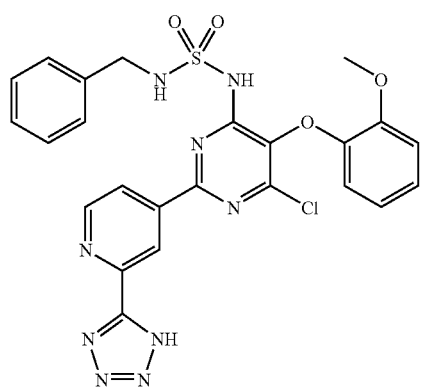

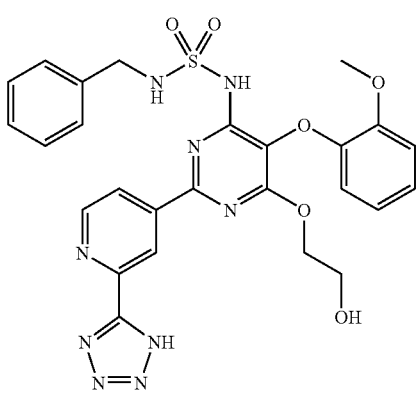

Example 208

Benzylsulfamic acid [6-(2-hydroxy-ethoxy)-5-(2-methoxy-phenoxy)-2-[2-(1H-tetrazol-5-yl)-pyridin-4-yl]-pyrimidin-4-tl]-amide (1.5 g) was prepared according to the procedure described in Example 207d. LC-MS: $t_R$=4.28; [M+H]$^+$=592.63.

Example 209

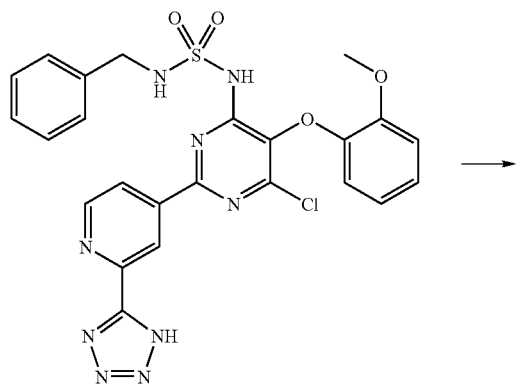

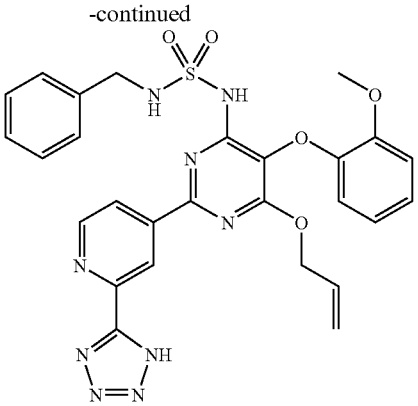

Example 209

Benzylsulfamic acid [6-allyloxy-5-(2-methoxy-phenoxy)-2-[2-(1H-tetrazol-5-yl)-pyridin-4-yl]-pyrimidin-4-yl]-amide (94 mg) was prepared according to the procedure described in Example 207d. LC-MS: $t_R$=4.96; (M+H)$^+$=588.70.

Example 210

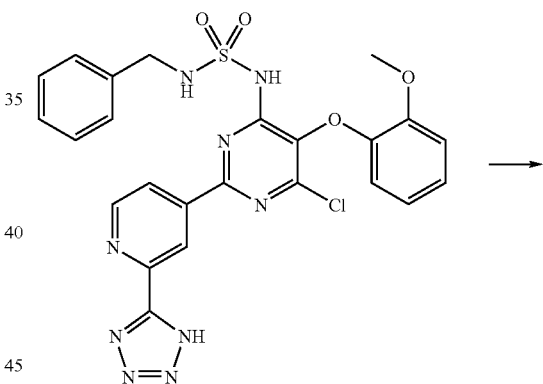

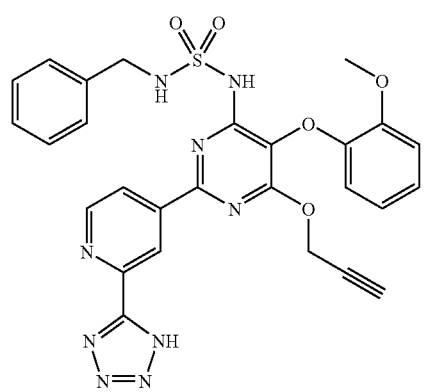

Example 210

Benzylsulfamic acid [5-(2-methoxy-phenoxy)-6-prop-2-ynyloxy-2-[2-(1H-tetrazol-5-yl)pyridin-4-yl]-pyrimidin-4- yl]-amide (100 mg) was prepared according to the procedure described in Example 207d. LC-MS: $t_R$=4.77; [M+H]$^+$=486.51.

Example 211-212

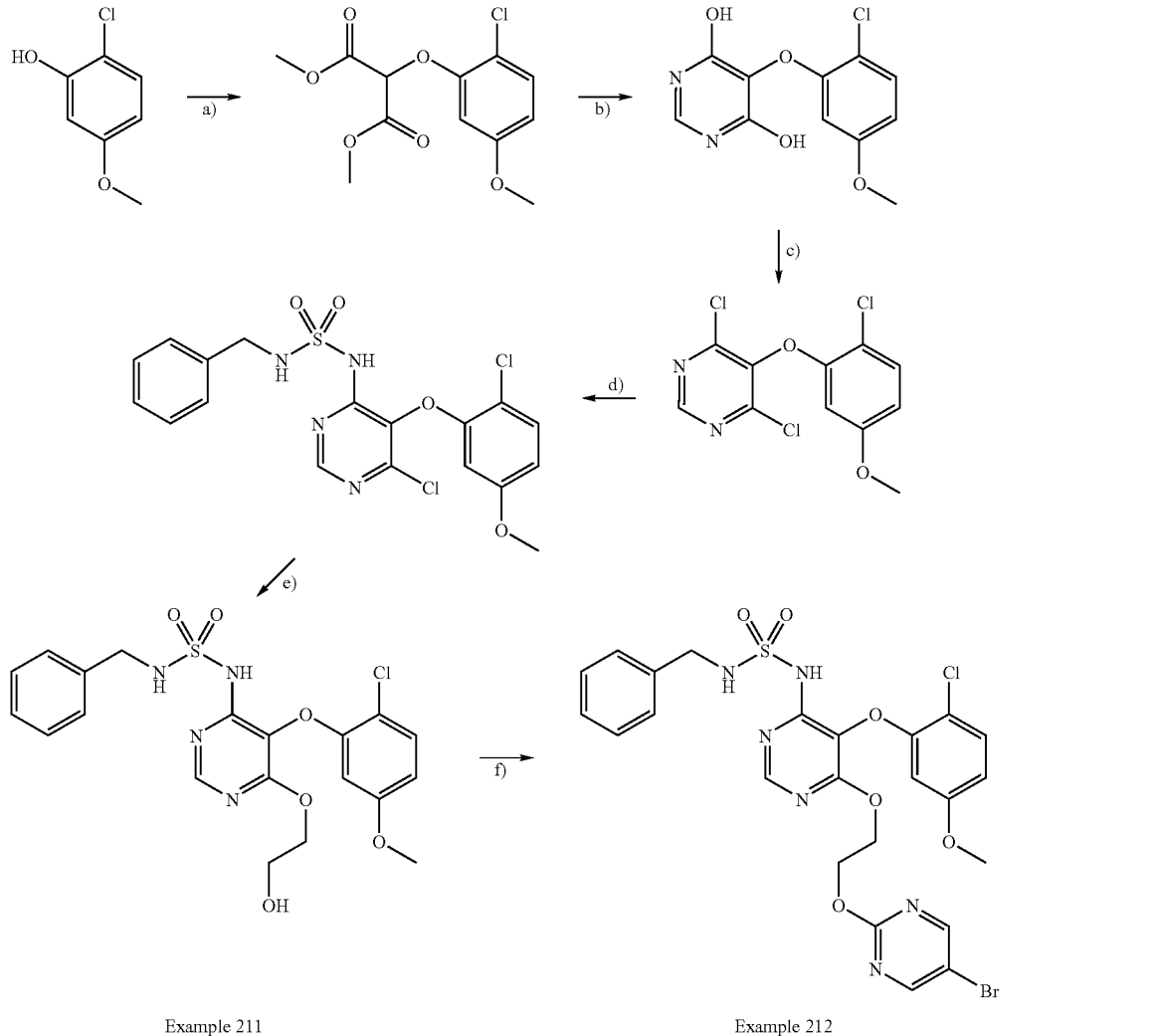

Example 211

Example 212

2-Chloro-5-methoxy-phenol was prepared according to procedures described in the literature [M. Julia, J. de Rosnay; *Chimie Thérapeutique*, 1969, 4, p 334-343.]

a) 2-Chloro-5-methoxy-phenol was reacted with chloro dimethyl malonate in acetone and potassium carbonate according to the procedure described in so Referential Example 1b to give 2-(2-chloro-5-methoxy-phenoxy)-malonic acid dimethyl ester.

b) 5-(2-Chloro-5-methoxy-phenoxy)-pyrimidine-4,6-diol was prepared from 2-(2-chloro-5-methoxy-phenoxy)-malonic acid dimethyl ester and formamidine hydrochloride according to the procedure described in Referential Example 1c.

c) 4,6-Dichloro-5-(2-chloro-5-methoxy-phenoxy)-pyrimidine was prepared from 5-(2-Chloro-5-methoxy-phenoxy)-pyrimidine-4,6-diol according to the procedure described in Referential Example 3b. LC-MS: $t_R$=5.18; [M+H]$^+$=306.40; $^1$H-NMR (CDCl$_3$): 8.7 ppm (s, 1H); 7.4 ppm (d, 1H); 6.6 ppm (d, 1H); 6.02 ppm (s, 1H); 3.86 ppm (s, 3H).

d) Benzylsulfamic acid [6-chloro-5-(2-chloro-5-methoxy-phenoxy)-pyrimidinyl]-amide (0.7 g) was prepared from 4,6-dichloro-5-(2-chloro-5-methoxy-phenoxy)-pyrimidine (1 g) and benzylsulfamic acid amide potassium salt (1.21 g) according to the procedure described in Referential Example 15. LC-MS: $t_R$=5.13; [M+H]$^+$=456.91.

e) Benzylsulfamic acid [5-(2-chloro-5-methoxy-phenoxy)-6-(2-hydroxy-ethoxy)-pyrimidin-4-yl]-amide (0.6 g) (Example 211) was prepared from benzylsulfamic acid [6-chloro-5-(2-chloro-5-methoxy-phenoxy)-pyrimidin-4-yl]-amide (0.697 g) according to the procedure described in Example 3, 10 or 13. LC-MS: $t_R$=4.50; [M+H]$^+$=481.12.

f) Benzylsulfamic acid [6-[2-(5-bromo-pyrimidin-2-yloxy)-ethoxy]-5-(2-chloro-5-methoxy-phenoxy)-pyrimidin-4-yl]-amide (77 mg) (Example 212) was prepared from benzylsulfamic acid [5-(2-chloro-5-methoxy-phenoxy)-6-(2-hydroxy-ethoxy)-pyrimidin-4-yl]-amide (120 mg) (Example 211) and 5-bromo-2-chloropyrimidine (100 mg)

according to the procedure described in Example 14. LC-MS: $t_R$=5.29; [M+H]$^+$=639.04.

Example 213

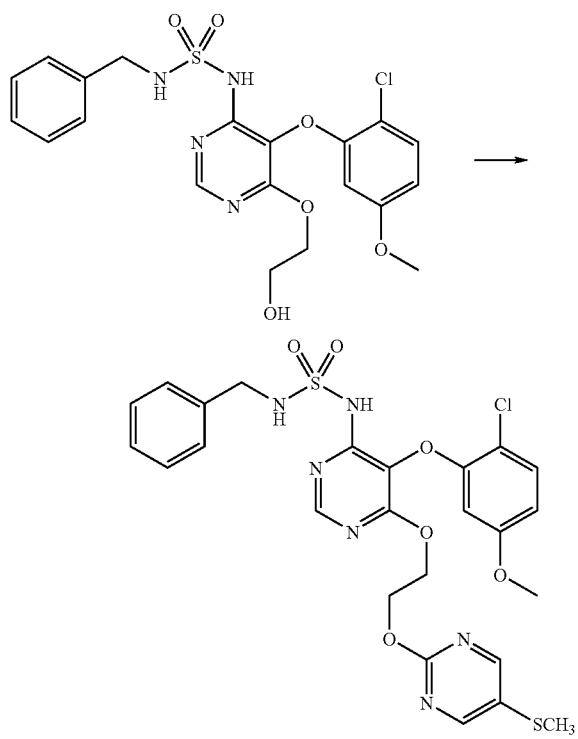

Benzylsulfamic acid [6-[2-(5-methylsulfanyl-pyrimidin-2-yloxy)-ethoxy]-5-(2-chloro-5-methoxy-phenoxy)-pyrimidin-4-yl]-amide (138 mg) (Example 213) was prepared from benzylsulfamic acid [5-(2-chloro-5-methoxy-phenoxy)-6-(2-hydroxy-ethoxy)-pyrimidin-4-yl]-amide (240 mg) (Example 211) and 5-methylsulfanyl-2-chloropyrimidine (180 mg) according to the procedure described in Example 14. LC-MS: $t_R$=5.22; [M+H]$^+$=606.75.

Example 214

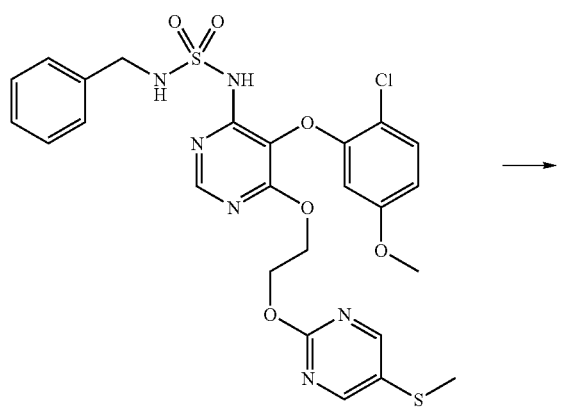

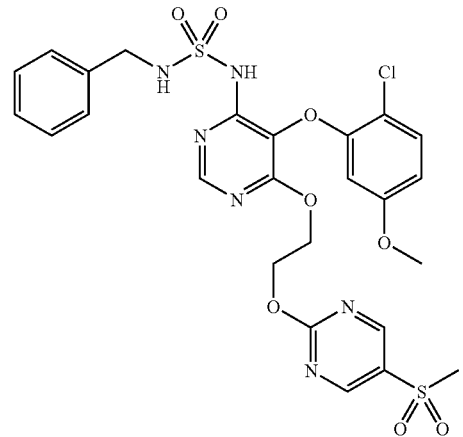

Benzylsulfamic acid [5-(2-chloro-5-methoxy-phenoxy)-6-[2-(5-methanesulfonyl-pyrimidin-2-yloxy)-ethoxy]-pyrimidin-4-yl]-amide (47 mg) (Example 214) was prepared by oxidation of benzylsulfamic acid [6-[2-(5-methylsulfanyl-pyrimidin-2-yloxy)-ethoxy]-5-(2-chloro-5-methoxy-phenoxy)-pyrimidin-4-yl]-amide (80 mg) (Example 213) with peracetic acid according to general procedures described in the literature. LC-MS: $t_R$=4.72; [M−H]$^+$=635.05.

According to the procedures described for the preparation of Examples 211-214, the following compounds can be prepared:

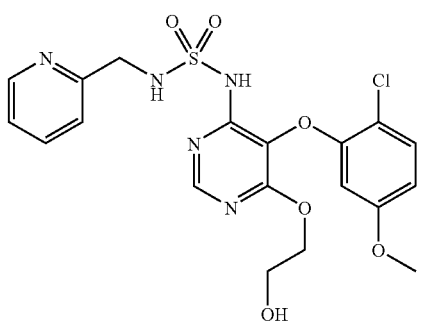

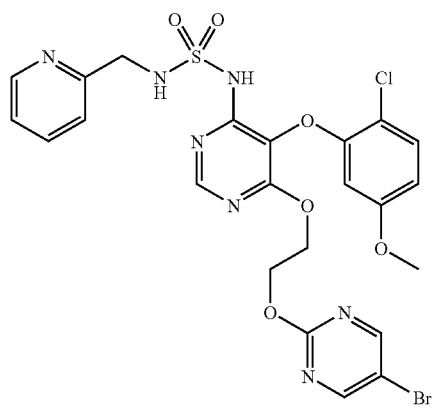

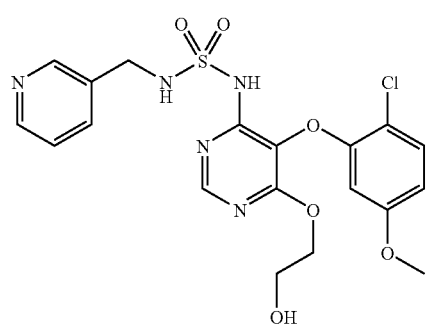

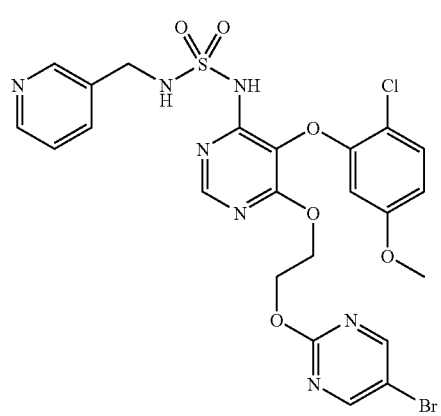

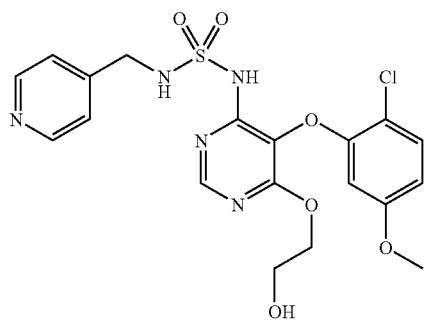

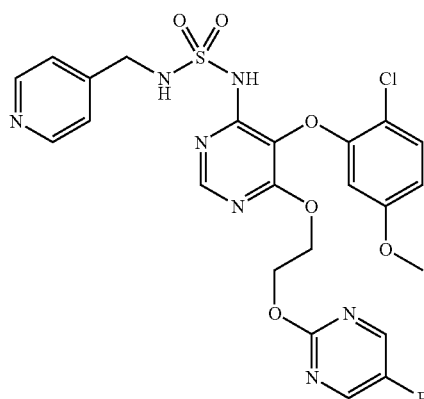

The preparation of compounds by the above described procedures is not limited to the molecules schematically depicted. Further variations, especially in the sulfamide-part and at the side chain in position 6 of the core pyrimidine ring of the molecule, can be achieved via the same pathway.

Example 215

Using methods described in the above Examples and in Schemes 1 to 4 and the cited references, the compounds disclosed in Table a) can be prepared:

TABLE a
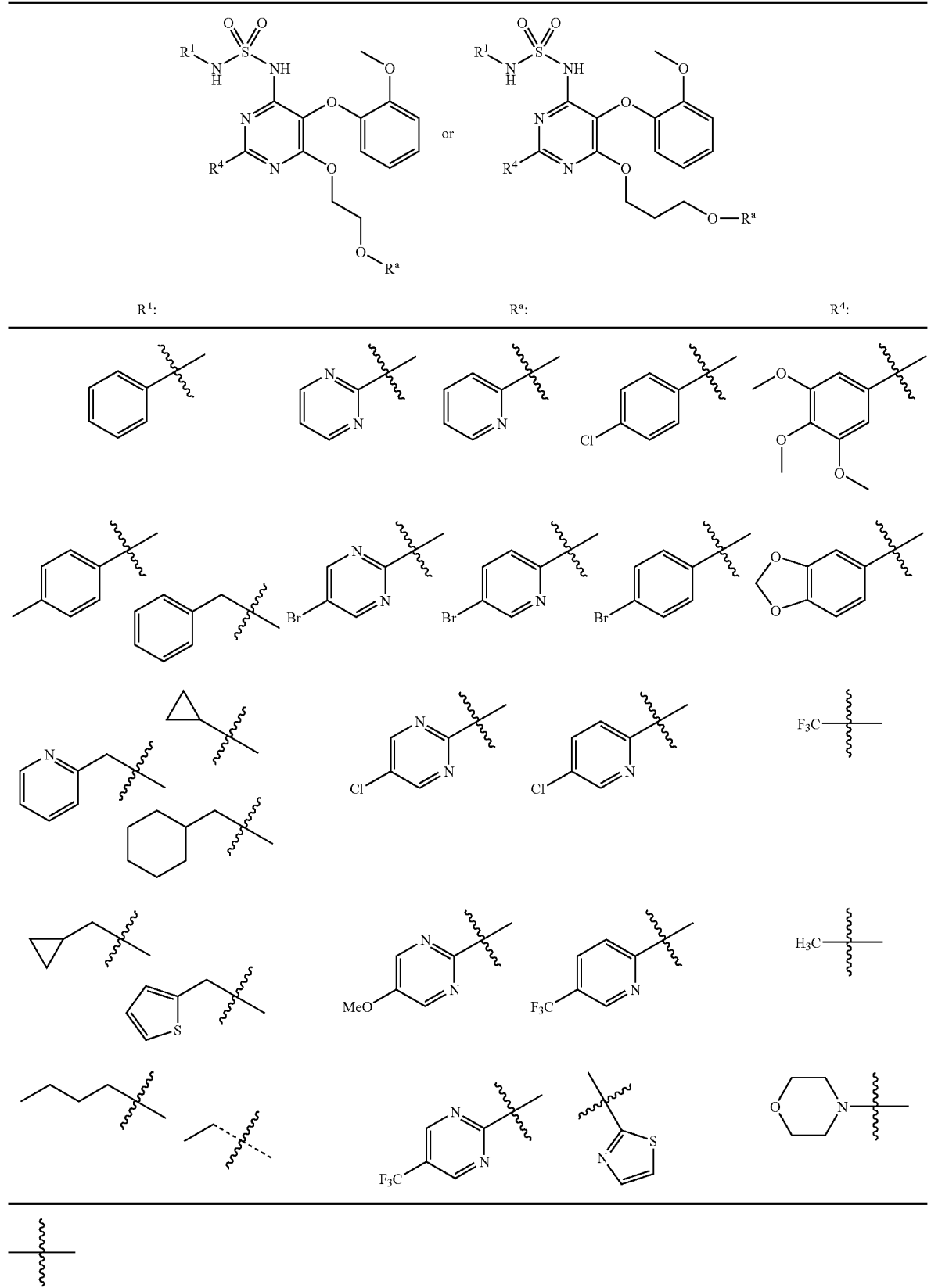
indicates the connection of the substituents to the respective atom of the core unit

Example 216
Using methods described in the above Examples and in Schemes 1 to 4 and in the cited references, the compounds disclosed in Table b) can be prepared:
TABLE b
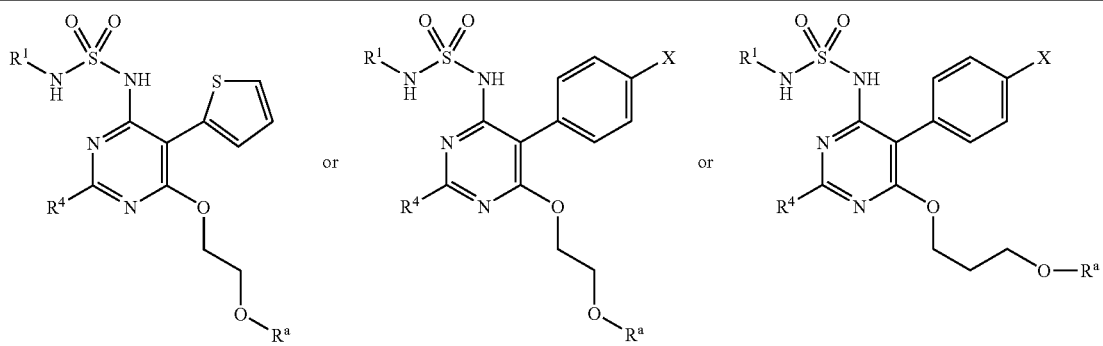
X = H; CH₃; Cl; Br; OCH₃; F; CF₃; CH₂CH₃
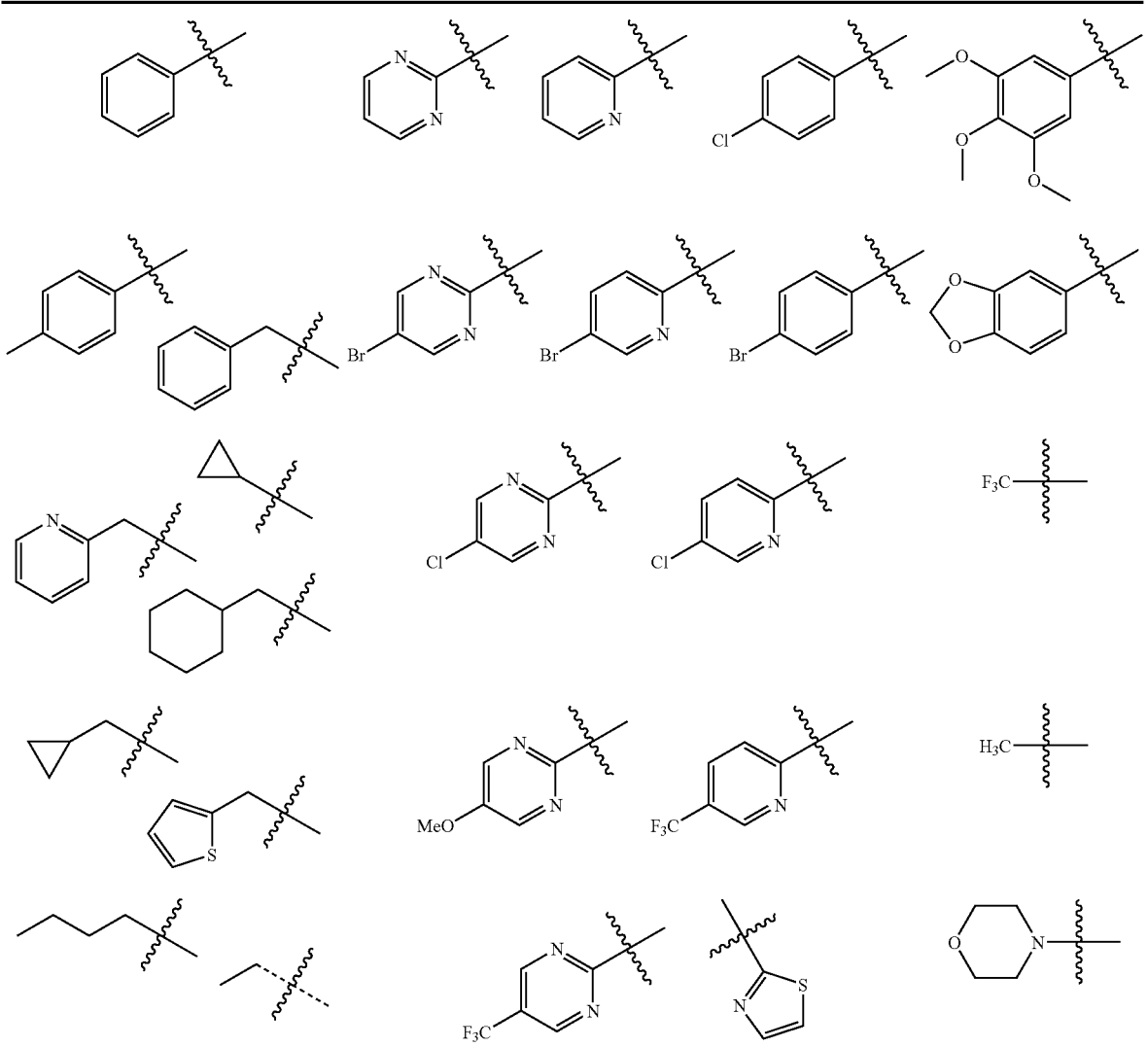

TABLE b-continued
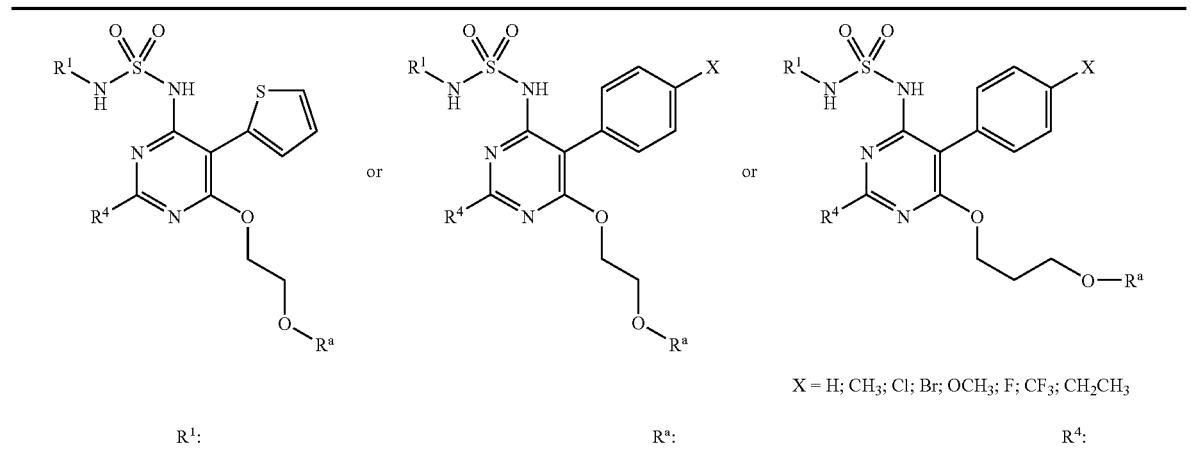
X = H; CH₃; Cl; Br; OCH₃; F; CF₃; CH₂CH₃
| R¹: | Rᵃ: | R⁴: |
|---|---|---|
indicates the connection of the substituents to the respective atom of the core unit
What is claimed:
1. A compound selected from the group consisting of the compounds having the following structures:
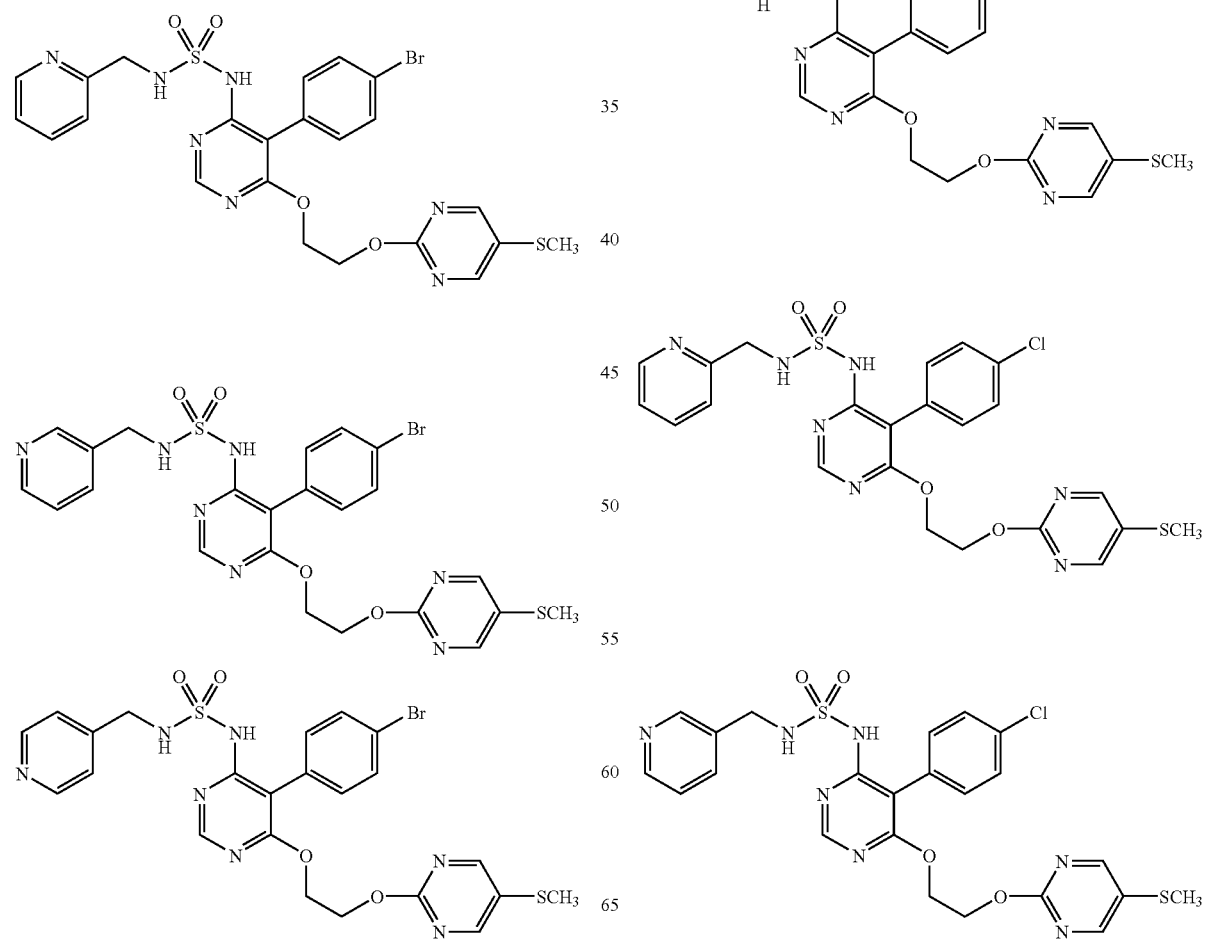

127 128
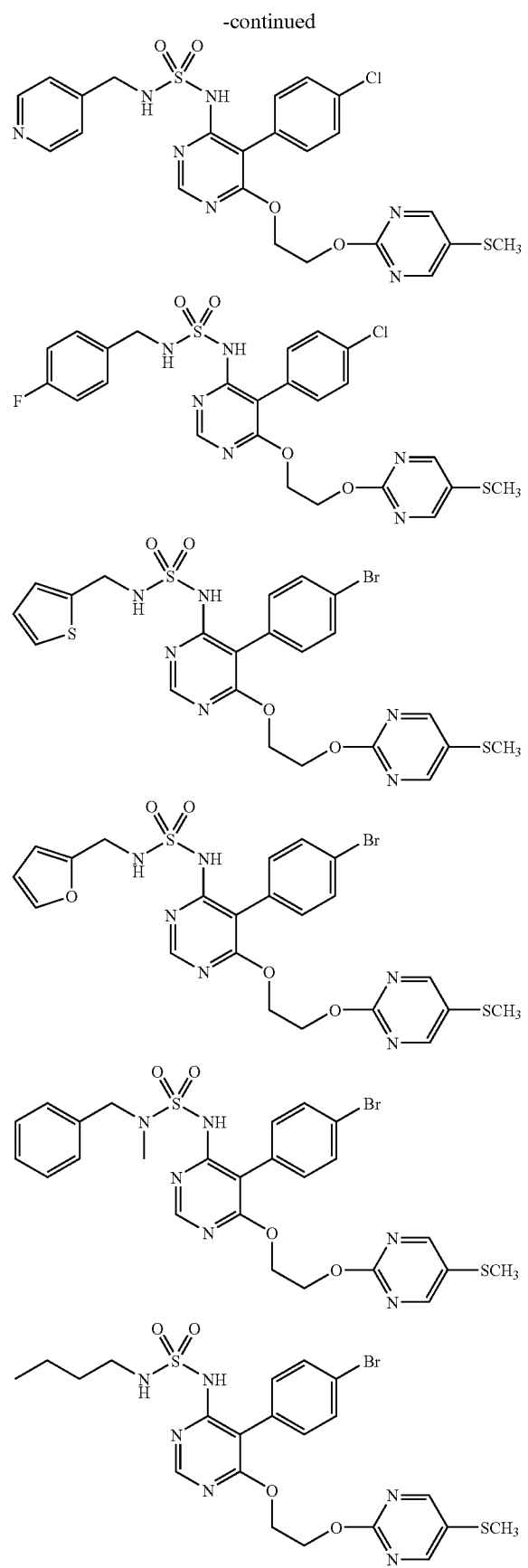
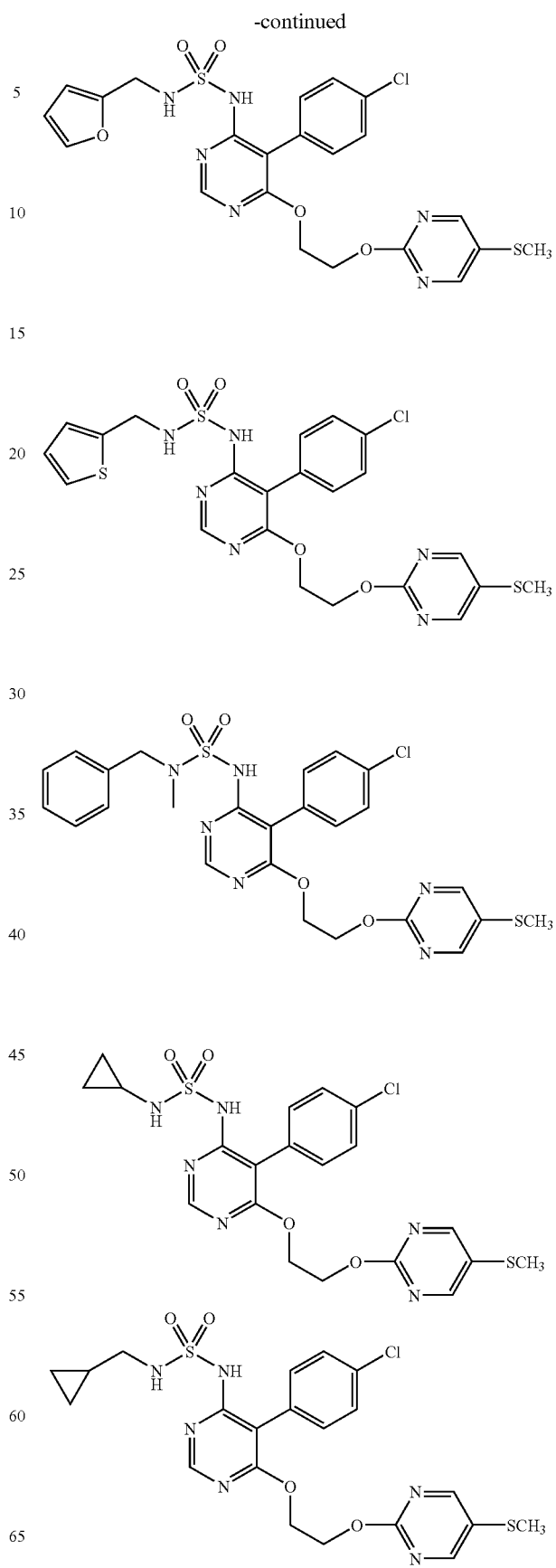

-continued
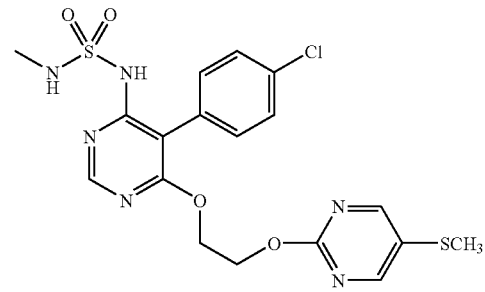
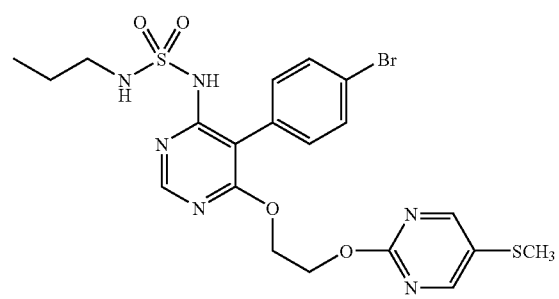
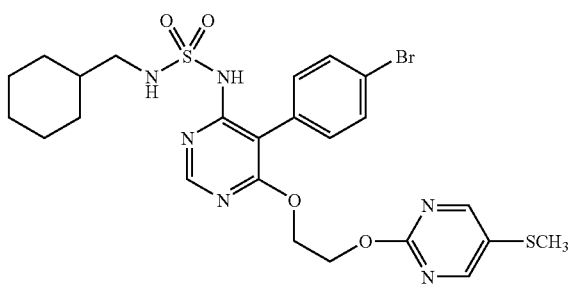
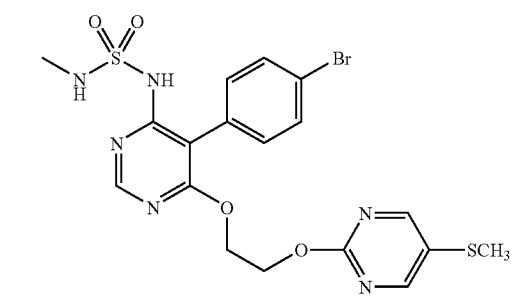
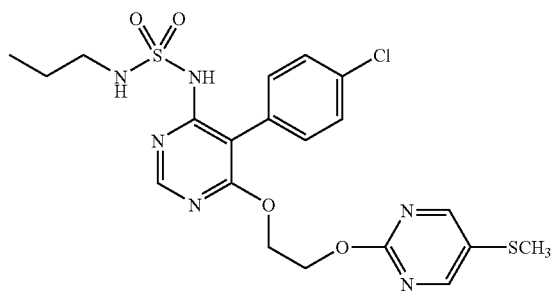
-continued
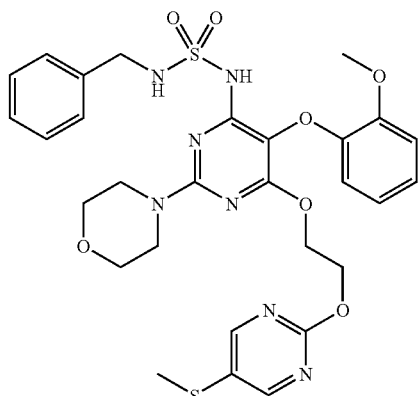
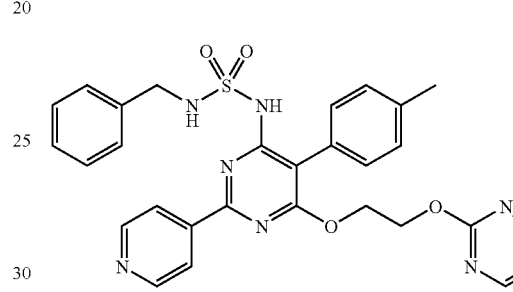
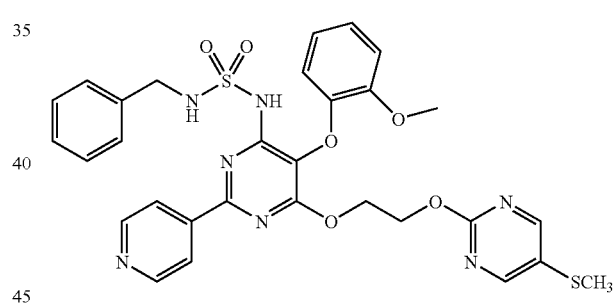
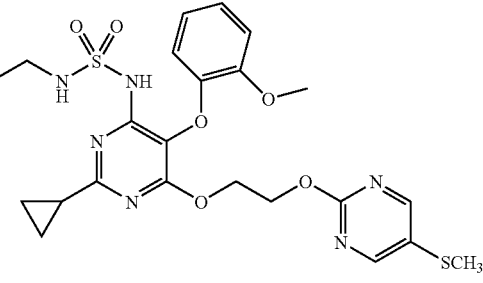
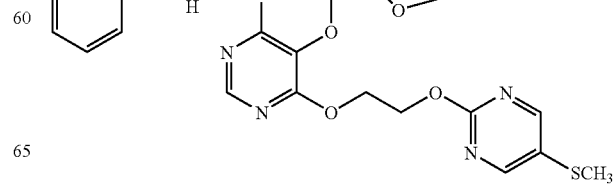

-continued
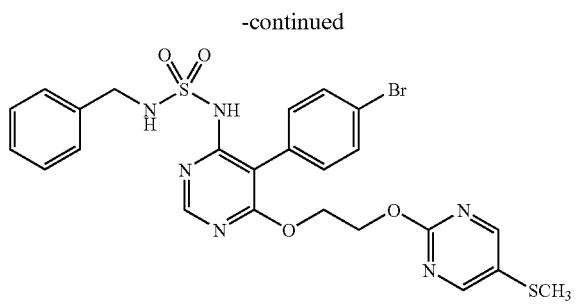
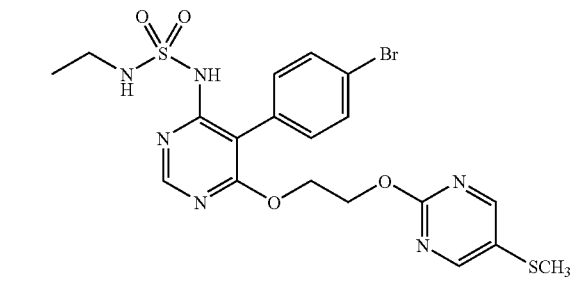
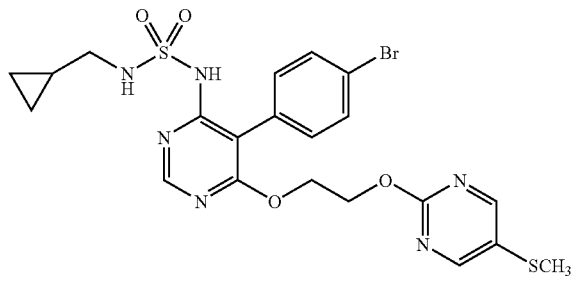
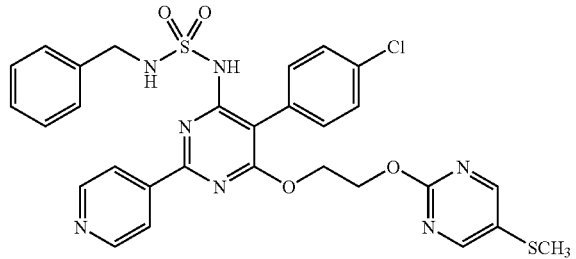
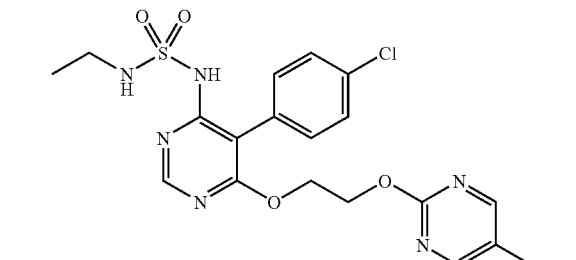
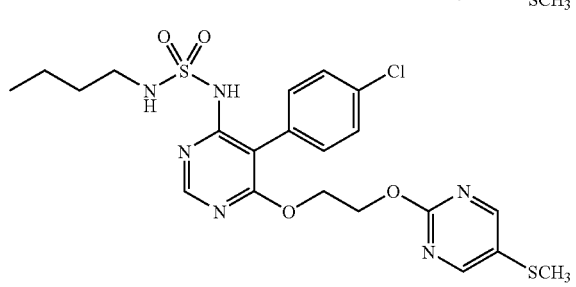
-continued
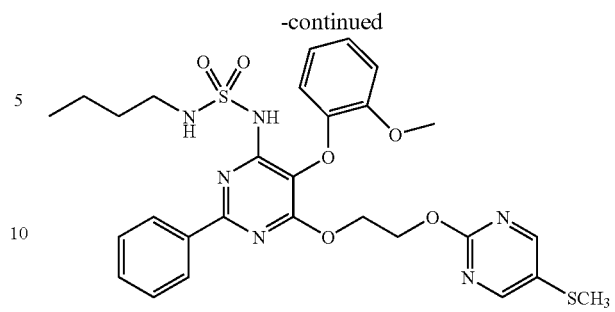
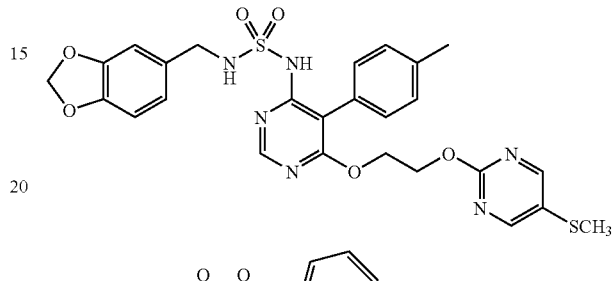
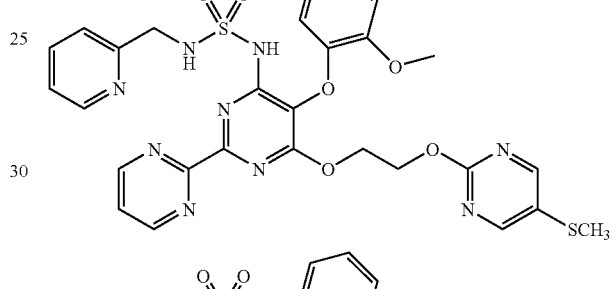
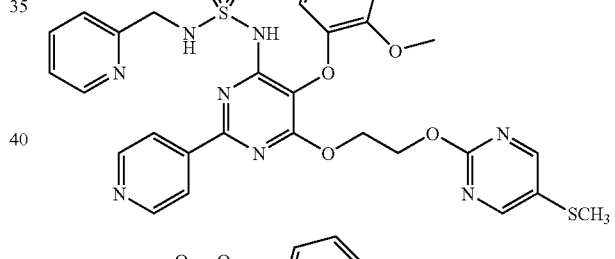
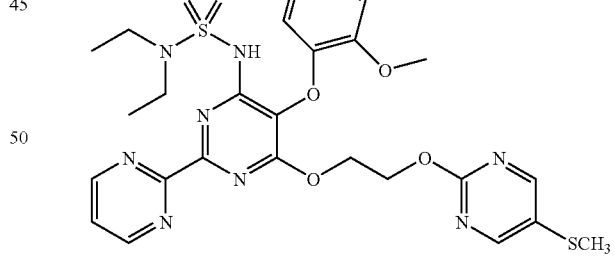
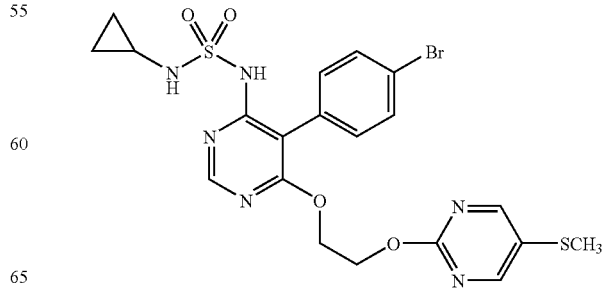

-continued

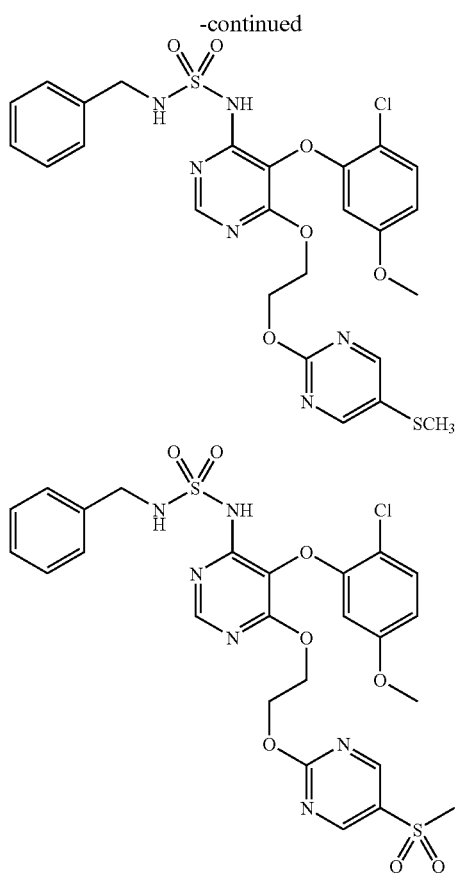

or a salt of such a compound.

2. The compound of claim 1, which has the following structure

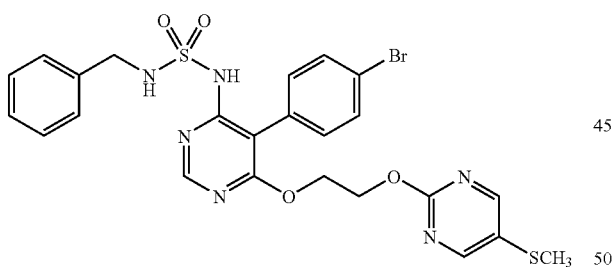

or a salt of this compound.

3. The compound of claim 1, which has the following structure

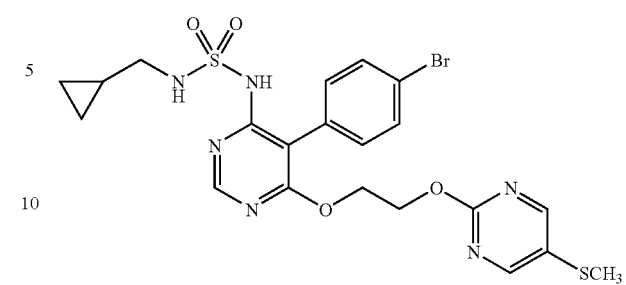

or a salt of this compound.

4. The compound of claim 1, which has the following structure

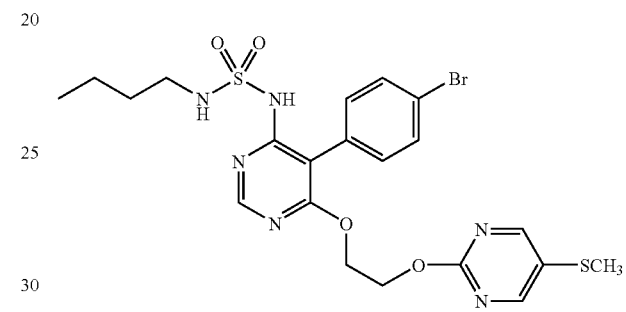

or a salt of this compound.

5. The compound of claim 1, which has the following structure

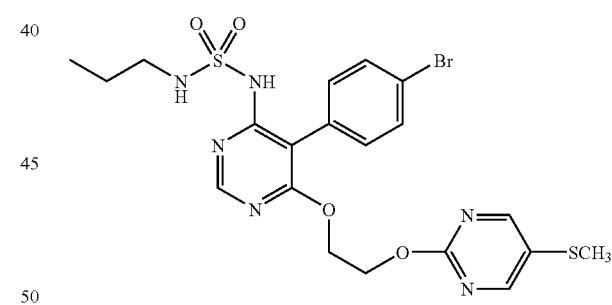

or a salt of this compound.

* * * * *